United States Patent
Ashley et al.

(10) Patent No.: US 9,545,316 B2
(45) Date of Patent: Jan. 17, 2017

(54) ADJUSTABLE DISTRACTION CAGE WITH LINKED LOCKING MECHANISMS

(71) Applicant: CoAlign Innovations, Inc., Brisbane, CA (US)

(72) Inventors: John E. Ashley, Danville, CA (US); Philip J. Simpson, Escondido, CA (US); Walter Dean Gillespie, Carlsbad, CA (US); Damien Shulock, San Francisco, CA (US); Murali Kadaba, Emerald Hills, CA (US); David G. Matsuura, Encinitas, CA (US); George A. Mansfield, III, San Diego, CA (US); Thomas Grotz, Novato, CA (US); Rudy Pretti, Auburn, CA (US); Dennis Crandall, Mesa, AZ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/644,969

(22) Filed: Mar. 11, 2015

(65) Prior Publication Data

US 2015/0289988 A1    Oct. 15, 2015

Related U.S. Application Data

(63) Continuation of application No. 13/843,390, filed on Mar. 15, 2013, now Pat. No. 8,992,620, which is a (Continued)

(51) Int. Cl.
*A61F 2/44*    (2006.01)
*A61F 2/30*    (2006.01)
(Continued)

(52) U.S. Cl.
CPC .............. *A61F 2/4455* (2013.01); *A61F 2/441* (2013.01); *A61F 2/442* (2013.01); *A61F 2/30742* (2013.01);
(Continued)

(58) Field of Classification Search
CPC ........ A61F 2/4455; A61F 2/442; A61F 2/441; A61F 2/4611; A61F 2002/485; A61F 2002/482
(Continued)

(56) References Cited

U.S. PATENT DOCUMENTS 3,875,595 A    4/1975 Froning
4,932,975 A    6/1990 Main et al.
(Continued)

FOREIGN PATENT DOCUMENTS

CN    1756516 A    4/2006
CN    101610741 A    12/2009
(Continued)

OTHER PUBLICATIONS

Japanese Office Action for Application No. 2013-512209 dated Jan. 27, 2015.
(Continued)

*Primary Examiner* — Alvin Stewart
(74) *Attorney, Agent, or Firm* — Lerner, David, Littenber, Krumholz & Mentlik, LLP

(57) ABSTRACT

A spinal implant which is configured to be deployed between adjacent vertebral bodies. The implant has at least one extendable support element with a retracted configuration to facilitate deployment of the implant and an extended configuration so as to expand the implant and effectively distract the disc space, stabilize the motion segments and eliminate pathologic spine motion. The implant has a minimal dimension in its unexpanded state that is smaller than
(Continued)

the dimensions of the neuroforamen through which it typically passes to be deployed within the intervertebral space. The implant is provided with a locking system having a plurality of linked locking elements that work in unison to lock the implant in an extended configuration. Bone engaging anchors also may be provided to ensure secure positioning.

20 Claims, 50 Drawing Sheets

Related U.S. Application Data continuation-in-part of application No. 12/787,281, filed on May 25, 2010, now Pat. No. 8,696,751, which is a continuation-in-part of application No. PCT/US2009/067446, filed on Dec. 10, 2009, which is a continuation of application No. 12/548,260, filed on Aug. 26, 2009, now Pat. No. 8,435,296, which is a continuation-in-part of application No. 12/380,840, filed on Mar. 4, 2009, now abandoned, and a continuation-in-part of application No. 12/072,044, filed on Feb. 22, 2008, now Pat. No. 8,932,355.

(60) Provisional application No. 61/201,518, filed on Dec. 10, 2008.

(51) Int. Cl.
*A61F 2/46* (2006.01)
*A61F 2/48* (2006.01)

(52) U.S. Cl.
CPC ...... *A61F 2/4611* (2013.01); *A61F 2002/3008* (2013.01); *A61F 2002/3055* (2013.01); *A61F 2002/30079* (2013.01); *A61F 2002/30133* (2013.01); *A61F 2002/30365* (2013.01); *A61F 2002/30405* (2013.01); *A61F 2002/30476* (2013.01); *A61F 2002/30484* (2013.01); *A61F 2002/30499* (2013.01); *A61F 2002/30505* (2013.01); *A61F 2002/30514* (2013.01); *A61F 2002/30522* (2013.01); *A61F 2002/30525* (2013.01); *A61F 2002/30551* (2013.01); *A61F 2002/30565* (2013.01); *A61F 2002/30579* (2013.01); *A61F 2002/30581* (2013.01); *A61F 2002/30589* (2013.01); *A61F 2002/30601* (2013.01); *A61F 2002/30841* (2013.01); *A61F 2002/482* (2013.01); *A61F 2002/485* (2013.01); *A61F 2310/00017* (2013.01); *A61F 2310/00023* (2013.01)

(58) Field of Classification Search
USPC .............................. 623/17.11–17.16
See application file for complete search history.

(56) References Cited

U.S. PATENT DOCUMENTS

| | | |
|---|---|---|
| 4,969,888 A | 11/1990 | Scholten et al. |
| 5,236,460 A | 8/1993 | Barber |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Buttermann |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,176,881 B1 | 1/2001 | Schar et al. |
| 6,193,756 B1 | 2/2001 | Studer et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 | 9/2002 | Cohen et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 | 7/2011 | Grotz et al. |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |

(56) References Cited

U.S. PATENT DOCUMENTS

| | | |
|---|---|---|
| 8,105,382 B2 | 1/2012 | Olmos et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,303,663 B2 | 11/2012 | Jimenez et al. |
| 8,353,961 B2 | 1/2013 | McClintock et al. |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,696,751 B2 | 4/2014 | Ashley et al. |
| 2001/0056302 A1 | 12/2001 | Boyer et al. |
| 2002/0128716 A1 | 9/2002 | Cohen et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2004/0030346 A1 | 2/2004 | Frey et al. |
| 2004/0088054 A1 | 5/2004 | Berry |
| 2004/0097928 A1 | 5/2004 | Zdeblick et al. |
| 2004/0133273 A1 | 7/2004 | Cox |
| 2004/0153065 A1 | 8/2004 | Lim |
| 2004/0153156 A1 | 8/2004 | Cohen et al. |
| 2004/0186576 A1 | 9/2004 | Biscup et al. |
| 2005/0033437 A1 | 2/2005 | Bao et al. |
| 2005/0043800 A1 | 2/2005 | Paul et al. |
| 2005/0049590 A1 | 3/2005 | Alleyne et al. |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0149377 A1 | 7/2006 | Navarro et al. |
| 2006/0167547 A1 | 7/2006 | Suddaby |
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1 | 10/2007 | Grotz et al. |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0215153 A1 | 9/2008 | Butterman et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0016970 A1 | 1/2010 | Kapitan et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2010/0249930 A1 | 9/2010 | Myers |
| 2011/0130835 A1 | 6/2011 | Ashley et al. |
| 2011/0137416 A1 | 6/2011 | Myers |
| 2011/0270398 A1 | 11/2011 | Grotz et al. |
| 2011/0288646 A1 | 11/2011 | Moskowitz et al. |
| 2012/0059469 A1 | 3/2012 | Myers et al. |
| 2012/0116518 A1 | 5/2012 | Grotz et al. |
| 2012/0130387 A1 | 5/2012 | Simpson et al. |
| 2012/0245695 A1 | 9/2012 | Simpson et al. |
| 2012/0283830 A1 | 11/2012 | Myers |
| 2013/0096677 A1 | 4/2013 | Myers et al. |
| 2013/0158669 A1 | 6/2013 | Sungarian et al. |
| 2013/0197642 A1 | 8/2013 | Ernst |
| 2013/0197647 A1 | 8/2013 | Wolters et al. |
| 2013/0197648 A1 | 8/2013 | Boehm et al. |
| 2013/0204368 A1 | 8/2013 | Prevost |
| 2013/0204374 A1 | 8/2013 | Milella, Jr. |
| 2013/0253650 A1 | 9/2013 | Ashley et al. |

FOREIGN PATENT DOCUMENTS

| | | |
|---|---|---|
| CN | 101631516 A | 1/2010 |
| CN | 101686860 A | 3/2010 |
| CN | 101686865 A | 3/2010 |
| EP | 1415624 A1 | 5/2004 |
| EP | 1442715 A2 | 8/2004 |
| JP | 2001-518824 A | 10/2001 |
| JP | 2008-502372 A | 1/2008 |
| WO | 03003951 A1 | 1/2003 |
| WO | 2004016205 A2 | 2/2004 |
| WO | 2004016250 A1 | 2/2004 |
| WO | 2006044786 A2 | 4/2006 |
| WO | 2007124078 A2 | 11/2007 |
| WO | 2008011371 A2 | 1/2008 |
| WO | 2008039811 A2 | 4/2008 |
| WO | 2008086276 A2 | 7/2008 |
| WO | 2008112607 A2 | 9/2008 |
| WO | 2008121251 A2 | 10/2008 |
| WO | 2008148210 A1 | 12/2008 |
| WO | 2009033100 A1 | 3/2009 |
| WO | 2009064787 A2 | 5/2009 |
| WO | 2009105182 A1 | 8/2009 |
| WO | 2009114381 A1 | 9/2009 |
| WO | 2010068725 A2 | 6/2010 |
| WO | 2011011609 A2 | 1/2011 |
| WO | 2011150077 A1 | 12/2011 |

OTHER PUBLICATIONS

International Search Report and Written Opinion dated Sep. 22, 2011 in related International Application No. PCT/US2011/037929.
International Search Report and Written Opinion dated Aug. 13,

(56) References Cited

OTHER PUBLICATIONS 2010, in related International Application No. PCT/US2009/067446 filed Dec. 10, 2009.

International Search Report and Written Opinion dated May 6, 2009. In related International Application No. PCT/US2009/000974 filed Feb. 17, 2009.

International Search Report and Written Opinion dated Jun. 30, 2009, in related International Application No. PCT/US2008/003776 filed Mar. 21, 2008.

International Search Report and Written Opinion dated Apr. 10, 2008, in related International Application No. PCT/US2007/079474.

International Search Report and Written Opinion dated Nov. 11, 2010, in International Application No. PCT/US2010/031247 entitled "Insertion Handle for Implant."

International Search Report and Written Opinion dale mailed Jun. 5, 2009 for related PCT/US2009/000974.

International Search Report and Written Opinion dated May 6, 2009, in related International Application No. PCT/US2009/000974 filed Feb. 17, 2009.

International Search Report & Written Opinion for Application No. PCT/US2009/000974 dated Jun. 5, 2009.

Extended European Search Report for Application No. EP14159619 dated Jun. 12, 2014.

Extended European Search Report for Application No. 11787340.6 dated Jun. 25, 2014.

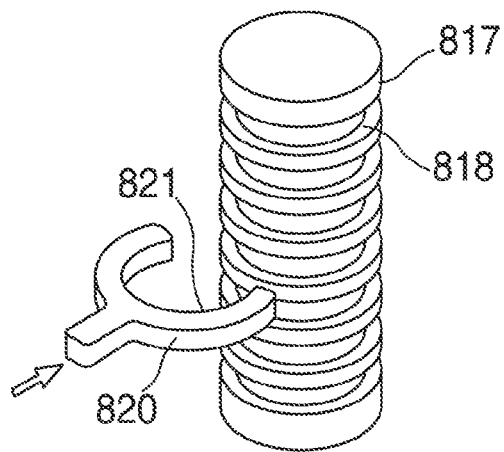
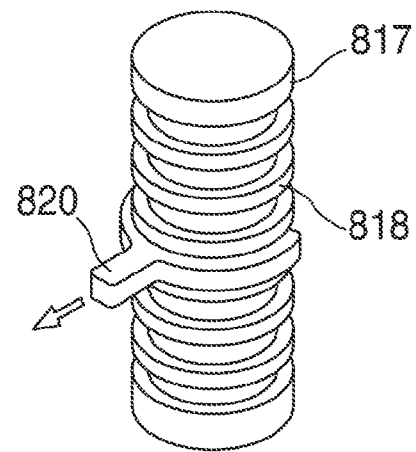
FIG. 20A    FIG. 20B
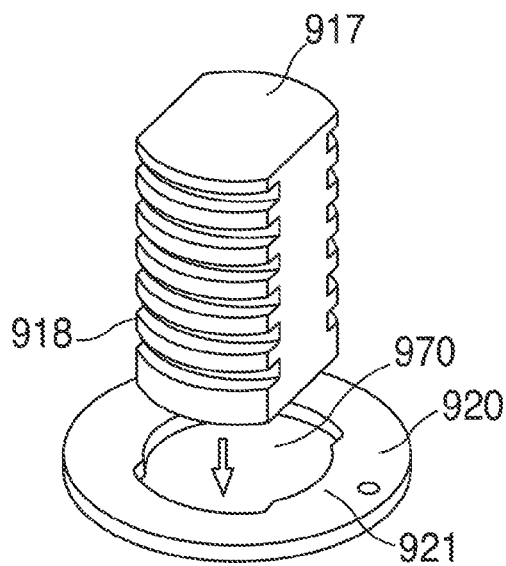
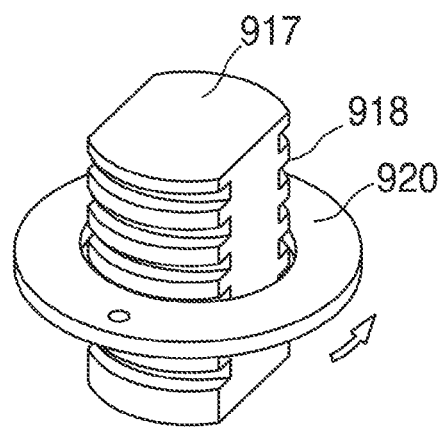
FIG. 21A    FIG. 21B

ADJUSTABLE DISTRACTION CAGE WITH LINKED LOCKING MECHANISMS

CROSS-REFERENCE TO RELATED APPLICATIONS

The present application is a continuation of U.S. patent application Ser. No. 13/843,390, filed on Mar. 15, 2013, which is a continuation-in-part of U.S. patent application Ser. No. 12/787,281, filed on May 25, 2010, which is a continuation-in-part of International Application No. PCT/US2009/67446 filed Dec. 10, 2009, which is a continuation of U.S. patent application Ser. No. 12/548,260, filed on Aug. 26, 2009. U.S. patent application Ser. No. 12/548,260 is a continuation-in-part of U.S. patent application Ser. No. 12/072,044, filed on Feb. 22, 2008, and is a continuation-in-part of U.S. patent application Ser. No. 12/380,840, filed on Mar. 4, 2009, which claims the benefit of the filing date of U.S. Provisional Patent Application No. 61/201,518, filed on Dec. 10, 2008, the disclosures of which are hereby incorporated herein by reference.

FIELD OF THE INVENTION

The invention relates to devices and methods for stabilizing the vertebral motion segment. More specifically, the field of the invention relates to an expandable spinal implant with locking elements configured to lock the implant in an expanded configuration within an intervertebral space to provide controlled spinal correction in three dimensions for improved spinal intervertebral body distraction and fusion.

BACKGROUND

A conventional spine cage or implant is characterized by a kidney bean shaped body which is typically inserted posteriorly through the neuroforamen of the distracted spine after a trial implant creates a pathway. Existing devices for interbody stabilization have important and significant limitations, including inability to expand and distract the end plates or to fix the device in place to prevent relative movement between the device and an adjacent vertebral body. Current devices for interbody stabilization include static spacers composed of titanium, PEEK, and high performance thermoplastic polymer produced by VICTREX, (Victrex USA Inc, 3A Caledon Court; Greenville, S.C. 29615), carbon fiber, or resorbable polymers. Moreover, current interbody spacers do not maintain interbody lordosis and can contribute to the formation of a straight or even kyphotic segment and the clinical problem of "flatback syndrome." Separation of vertebral end plates increases space available for the neural elements, specifically the neural foramen. Existing static cages do not reliably improve space for the neural elements. Therefore, what is needed is a spinal implant that will provide space for the neural elements posteriorly between the vertebral bodies, or at least maintain the natural bone contours to avoid neuropraxia (nerve stretch) or encroachment.

Conventional devices for intervertebral body stabilization include poor interface between bone and the biomaterial of the device. Conventional static interbody spacers form a weak interface between bone and biomaterial. Although the surface of such implants is typically provided with a series of ridges or coated with hydroxyapetite, the ridges may be in parallel with applied horizontal vectors or side-to-side motion. That is, the ridges or coatings on the implant offer little resistance to movement applied to either side of the end plates. Thus, nonunion is common in allograft, titanium and polymer spacers, due to motion between the implant and host bone.

SUMMARY OF THE DISCLOSURE

This invention is generally directed to a spinal implant for insertion between superior and second vertebral end plates after partial or total removal of a spinal disc. The spinal implant embodying features of the invention has a contracted configuration for easy installation between adjacent vertebral bodies and an expanded configuration to support the vertebrae in a desirable position. More specifically, the implant has a plurality of inter-engagable elements which locks the implant in an expanded configuration to hold the vertebral or joint sections in the desired positions.

The invention is particularly directed to a spinal implant suitable for placement between superior and interior vertebral bodies. The spinal implant has a first member or top plate for engaging an end of the superior vertebral body and a second member or base for engaging an end of the inferior vertebral body and has one or more extendable support elements preferably with one or more top end plates that engage vertebral bodies in the expanded configuration. The one or more extendable support elements have a first contracted configuration to facilitate deployment of the implant between the superior and inferior vertebral bodies and safely past sensitive neural elements and a second or an extended configuration to engage the end plates of the vertebral bodies. The implant has a locking system with linked locking elements that mechanically engage or interlock with the extendable support element or the first member to lock the implant between the superior and inferior vertebral bodies in an expanded configuration.

The extendable support element(s) may be extended in a variety of ways such as with fluid pressure, e.g. hydraulic fluid or gas, by mechanical force, such as a threaded connection with a rotating driving member or other suitable means. Fluidic displacement is preferred. The extendable support element(s) are disposed in cylinders which support and guide the extendable support elements when they are extended. However, the locking system is separate from the extendable support member and cylinder receiving the supporter member, although the extending support member may initiate the locking system and the support member and cylinder may have lock support members attached thereto.

In one exemplary system, the spinal implant having features of the invention comprises an inferior pressure applying member or base with a first bone engaging surface, one or more extendable support members cooperating with the base and a superior pressure applying member such as a top end plate with a second bone engaging surface that is coupled to the at least one extendable member. The spinal implant preferably has a plurality of engaging locking elements that are configured to independently lock one or more of the extendable support members or pressure applying members in an extended configuration to thereby provide desired disc height between adjacent vertebrae.

The spinal implant or selectively expanding spine cage (SEC) embodying features of the invention is particularly suitable for posterior or transforaminal insertion between superior and inferior vertebral end plates as described in copending application Ser. No. 11/535,432, filed Sep. 26, 2006, and Ser. No. 11/692,800, filed Mar. 28, 2007. The implant has a contracted or unexpanded configuration which allows easy deployment and is typically about 0.5 to about 1 cm in maximum short transverse dimension so as to enable minimally invasive insertion posteriorly between vertebral pedicles through a working space of approximately 1 cm in diameter.

In one exemplary embodiment, the spinal implant for placement between adjacent vertebral bodies as described above has an upper locking member with stepped supporting surfaces on the underside thereof and a lower locking member with stepped supporting surfaces on the top side thereof which are configured to engage the stepped supporting surface of the upper locking member to lock the implant in an extended configuration. Extension of the expandable members, such as bellows or pistons; or other appropriately sized mechanisms, such as cams or screws, to raise the superior pressure applying member increases longitudinal spacing between the upper and lower locking members. Relative motion, rotational or linear, between the upper and lower locking members causes the stepped supporting surfaces of the lower locking members and the stepped supporting surfaces of the upper locking members to re-engage to fix the locking members in an increased spaced apart relationship and thereby lock the implant in the extended configuration.

Since the vertebral end plates are held together at one end by a ligament much like a clamshell, as the implant expands against the vertebral end plates, the amount of vertical expansion can be adjusted to create the desired anterior/posterior correction angle.

A minimally invasive downsized insertion tool, such as described in the above referenced applications, both inserts the unexpanded implant posteriorly and provides the hydraulic or mechanical lines communicating with the interior of the implant. The insertion tool may also provide a line for communicating the liquid or slurry bone graft material into the intervertebral space for subsequent fusion. Advantageously, hydraulic lines are small size tubing to allow for high hydraulic pressure without danger of the lines bursting.

Due to the mechanical advantage provided by a hydraulic system or a proximally operated mechanical system, the implant has minimized size and diameter in its unexpanded state that is smaller than the diameter of a prepared neuroforamen. The implant thus can be inserted transforaminally and engaged between the end plates of the adjacent vertebra to effectively distract the intervertebral area, restore space for neural elements, stabilize the motion segment and eliminate pathologic segmental motion. The implant enhances spine arthrodesis by creating a rigid spine segment.

The implant is preferably provided with a hollow interior to enable a comparatively large quantity of bone growth conductive or inductive agents to be contained therein that through openings communicate directly to adjacent bone. Importantly, this results in fixation forces greater than adjacent bone and soft tissue failure forces. The implant can be used to promote fusion, and/or to correct deformities such as scoliosis, kyphosis, and spondylolisthesis.

The clinical goals of the implant and the method for its insertion provide a minimally invasive risk of trauma to nerve roots, reduce pain, improve function, and permit early mobilization of the patient after fusion surgery. The fixation elements maintain the implant in a desired position until healing (fusion or arthrodesis) occurs. At this point, the implant is incorporated inside bone and its role becomes quiescent.

Thus, a feature of the invention is that an implant can be inserted posteriorly between vertebral pedicles in only a working space of about ½ cm and then be expanded from about 100% to about 200%, typically about 160%, of its original insertion size and locked in that position to provide a closely controlled full range of permanent spinal correction in three dimensions. These and other advantages of the invention will become more apparent from the following detailed description and the accompanying exemplary drawings.

In other embodiments of the invention, extendable, locking, bone engaging anchors are provided to ensure that the implant is positively engaged with the bone after insertion.

In one implementation, the present disclosure is directed to a lockable, extendable spinal implant for placement between first and second vertebral bodies. The implant includes: first and second bone engaging members each having a surface configured to respectively engage opposed first and second vertebral bodies; extension means acting between the first and second bone engaging members to control extension of the bone engaging members between contracted and extended configurations; first and second fixed lock members fixed to one of the first and second bone engaging members and extending towards the opposite bone engaging member, the fixed lock members being spaced apart and each having a fixed locking surface; first and second moveable lock members captured between the first and second bone engaging members for cooperation with the fixed lock members, each moveable lock member having a moveable locking surface configured to engage an opposed fixed locking surface on one the fixed lock member to prevent contraction of the extension means; a locking actuator configured to engage the moveable locking surfaces with the fixed locking surfaces; and a link member operatively connected between the first and second moveable lock members to coordinate movement therebetween.

In another implementation, the present disclosure is directed to a lockable, extendable spinal implant for placement between first and second vertebral bodies. The implant includes: first and second bone engaging members each having a surface configured to respectively engage opposed first and second vertebral bodies; first and second pistons disposed on one the bone engaging member and cooperating with mating cylinders disposed on the opposite bone engaging member, the pistons moveable between a contracted configuration within the cylinders and an extended configuration extending from the cylinders; first and second arcuate, fixed lock members, each having a fixed locking surface, mounted to one of the bone engaging members, each disposed around one the piston, the fixed lock members extending towards the opposite bone engaging member; first and second moveable lock members, each formed around one the cylinder for cooperation with the fixed lock members, each moveable lock member having a moveable locking surface configured to engage an opposed fixed locking surface on one the fixed lock member to prevent contraction of the extension means; at least one biasing element acting on at least one the moveable lock member to bias the member into engagement with its associated fixed lock member; and a link member operatively connected between the first and second moveable lock members to coordinate movement therebetween and force the other moveable lock member into engagement with its associated fixed lock.

In still another implementation, the present disclosure is directed to a lockable, extendable spinal implant for placement between first and second vertebral bodies. The implant includes: first and second bone engaging members each having a surface configured to respectively engage opposed first and second vertebral bodies; first and second pistons disposed on one the bone engaging member and cooperating with mating cylinders disposed on the opposite bone engaging member, the pistons moveable between a contracted configuration within the cylinders and an extended configuration extending from the cylinders; first and second arcuate, fixed lock members, each having a fixed locking surface, mounted to one of the bone engaging members, each disposed inside one the piston, the fixed lock members extending towards the opposite bone engaging member; first and second moveable lock members, each formed inside one the cylinder for cooperation with the fixed lock members, each moveable lock member having a moveable locking surface configured to engage an opposed fixed locking surface on one the fixed lock member to prevent contraction of the extension means; at least one biasing element acting on at least one the moveable lock member to bias the member into engagement with its associated fixed lock member; and a link member operatively connected between the first and second moveable lock members to coordinate movement therebetween and force the other moveable lock member into engagement with its associated fixed lock.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 20A-20B, 21A-21B, 22-26, 27A-27B, and 28-29 schematically illustrate various means for locking an expanding member of implants in extended configurations embodying features of the invention.

DETAILED DESCRIPTION

Figure 1:
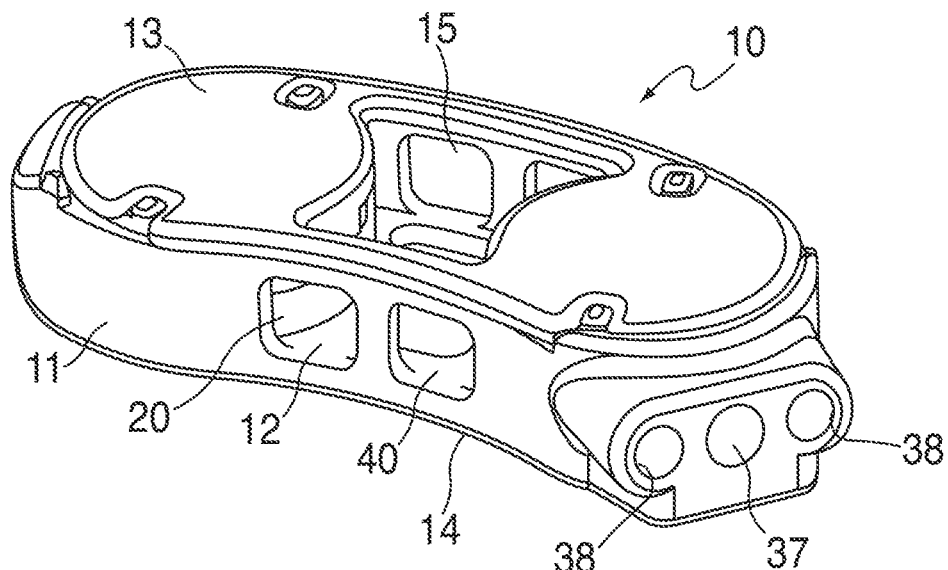
FIG. 1 is a perspective view of an intervertebral implant in a contracted configuration embodying features of the invention.

FIGS. 1-10B illustrate an example of an intervertebral implant 10, a Selectively Expandable Cage (SEC), having features of the invention. The implant 10 generally includes a housing 11, a housing base 12, an interlocking top end plate 13, a bottom end plate 14, an interior cavity 15 within the housing 11 and a pair of cylinders 16. The top and bottom end plates are the bone engaging members of the implant, providing surfaces for engaging vertebrae above and below the implant when placed in the patient. Upper lock supports 17 are attached to the underside of the top end plate 13 thus forming fixed lock members and have multi-stepped lower support surfaces 18 much like an inverted staircase. Lower lock supports 20, having multi-stepped upper support surfaces 21 surround cylinders 16 much like an upright staircase. The multi-stepped support surfaces form the locking surfaces of the lock supports. Pistons 22 are secured to the under surface of top end plate 13. Seal members 23 are slidably disposed within the cylinders 16 and are mounted on pistons 22. The upper surface 24 of bottom end plate 14 is provided with locking actuator channels 25 which partially receive spring locking actuators 26. The base 12 of the housing 11 has arcuate slots 27 which are configured to slidably receive the depending elements 28 or locking actuator transfer element of the lower lock supports 20 and partially receive the spring locking actuators 26. Depending elements 28 engage the forward end 30 of spring locking actuators 26. The spring locking actuators 26 are initially in a compressed configuration so that upon the extension of the top end plate 13 and the attached upper lock supports 17, the lower lock supports 20 rotate about the cylinders 16 due to the force applied by the biased spring locking actuator 26 thus forming moveable lock members. This causes the lock support surfaces 21 of the lower lock supports 20 to engage support surfaces 18 of the upper lock supports so as to lock the top end plate 13 in an extended configuration. The support surfaces 18 of the upper lock supports 17 and the support surfaces 21 of the lower lock supports 20 are tiered with multiple steps so that the implant 10 can be locked at several different expanded heights. The underside stepped support surfaces 18 of the upper lock support 17 may be provided with increasing riser height (alignment faces 46) in the upward direction to provide smaller incremental expansion near the end of the piston expansion. In addition or alternatively, the stepped support surfaces 21 of the lower lock support 20 may be provided with decreasing riser height in the upward direction for the same reason. A variety of riser heights of the upper lock support 17 or lower lock support 20 can be provided. The lowermost stepped support surface 18 of the upper lock support 17 and the uppermost stepped support surface 21 of the lower lock support 20 may be provided with various lengths and widths to ensure better support.

Figure 2:
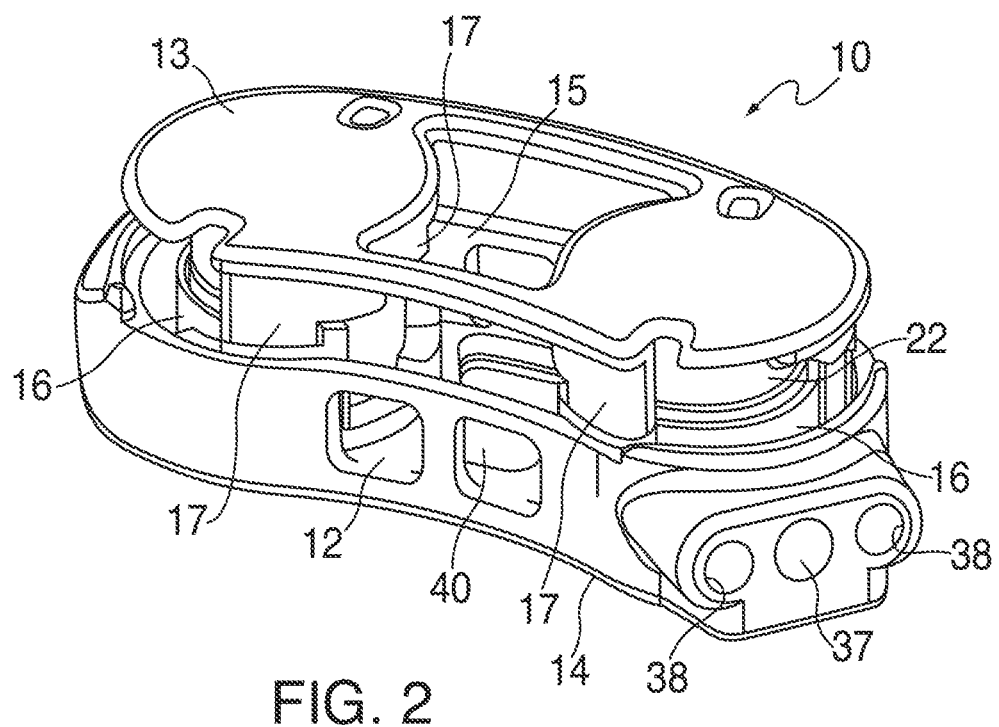
FIG. 2 is a perspective view of the implant shown in FIG. 1 in an expanded configuration.

As can be seen in FIG. 2 there are two sets of upper lock supports 17 attached to the top end plate 13 and there are two sets of lower lock supports 20 in this embodiment, but a single set or more than two sets of upper and lower lock supports can also be used to lock the implant 10 in the expanded state. Also shown, for example, in FIG. 2 are cylinders 16 and pistons 22, which provide one example of extension means in embodiments of the present invention. Other examples of extension means are described herein below in connection with alternative embodiments of the invention.

The implant 10 is configured to be implanted between opposing vertebral bodies in the spine to facilitate bony fusion between those vertebral bodies. The implant 10 is shown in its collapsed or contracted configuration in FIG. 1 and in one example of its expanded configuration in FIG. 2. In the collapsed state, the implant 10 can be inserted easily into the intervertebral body space through a minimal incision and with minimal tissue removal. Once in that space, the implant 10 can be expanded against the two opposing vertebral bodies to distract them and thereby restore height to the intervertebral space. This provides stable opposition of the implant 10 to both vertebral bodies and optimizes the bony fusion process. The fusion process can also be enhanced by filling the interior cavity 15 with autologous bone graft, a bone growth enabling matrix, and/or bone growth stimulating substances prior to and/or after insertion into the body.

Figure 3:
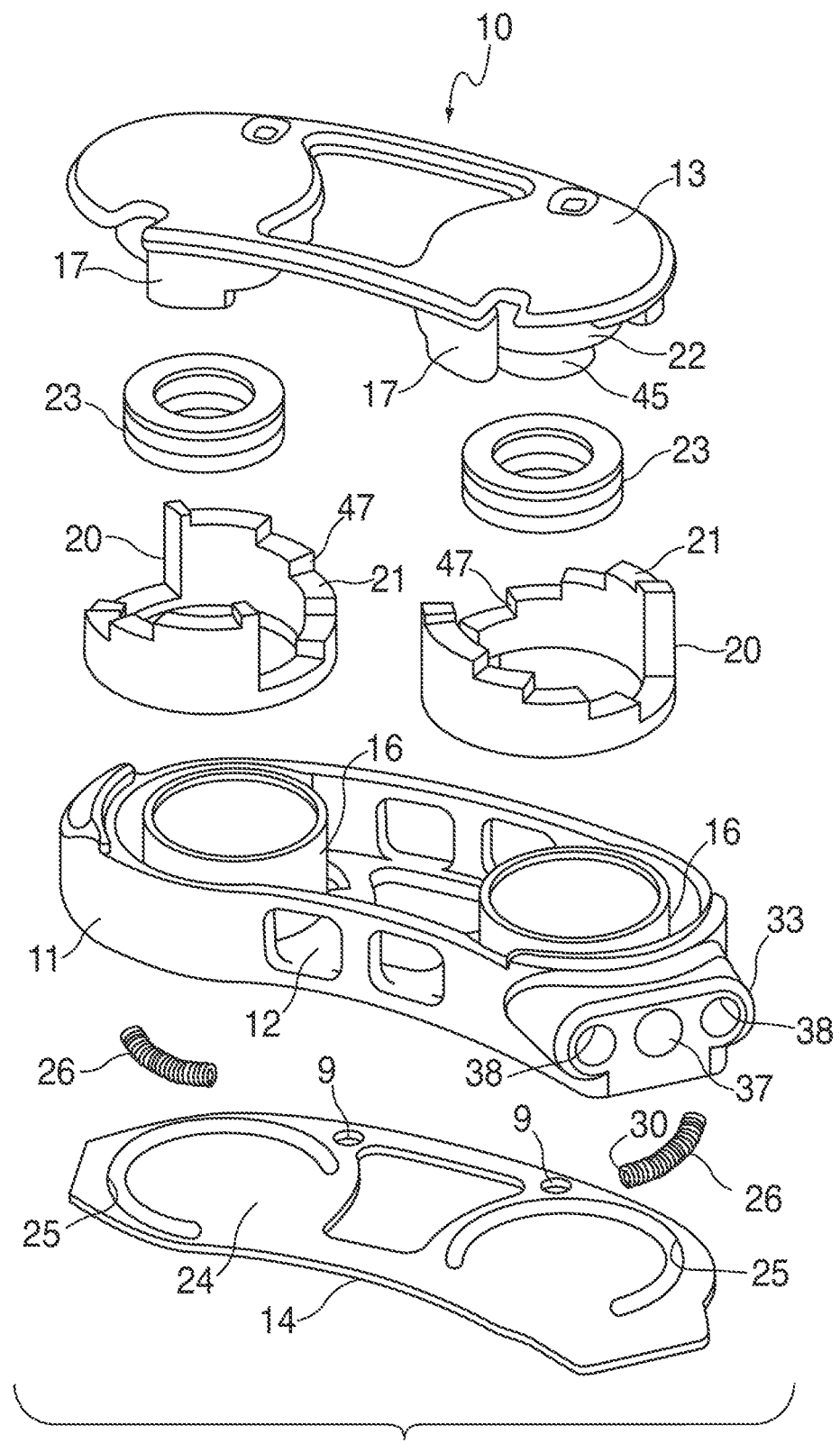
FIG. 3 is an exploded perspective view of the implant shown in FIG. 1.
Figure 4A:
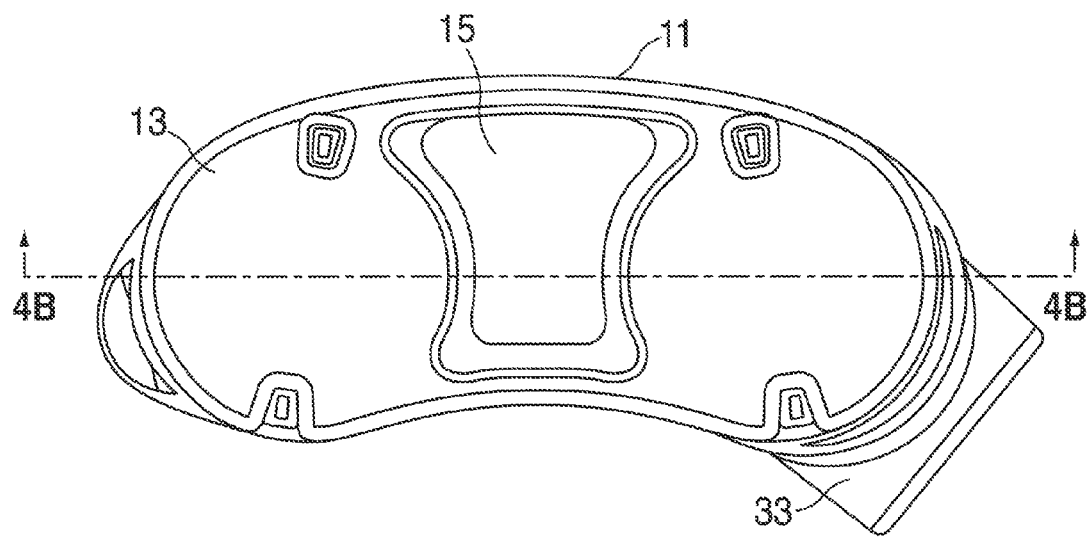
FIG. 4A is a top view of the implant shown in FIG. 1.
Figure 4B:
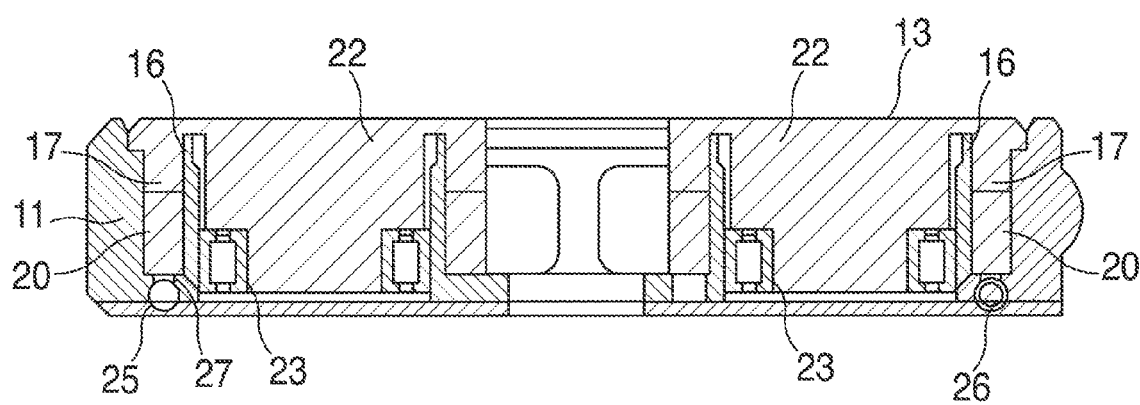
FIG. 4B is a side cross-sectional view through line 4B-4B of the implant shown in FIG. 4A.

Further details of individual parts of the implant are depicted in FIGS. 3, 4A and 4B. Pistons 22 are attached to the underside of the top end plate 13 which are configured to support seal members 23 which run inside of cylinders 16 located in the housing 11. When the cylinders 16 are pressurized as will be described in more detail below, the seals 23 running inside the cylinders 16 and pistons 22 slidably disposed within the seals are vertically displaced, translating the top end plate 13 vertically above the housing 11. Lower lock supports 20 are located around the outer wall of the cylinders 16. When the top end plate 13 is vertically displaced, which in turn displaces the attached upper lock supports 17, the lower lock supports are rotated by the biased locking actuators 26 to a locking position. Arcuate locking actuator channels 25 in the top surface of bottom plate 14 and the arcuate slots 27 in the housing base 12 confines the locking actuators 26 to the housing 11.

Figure 5A:
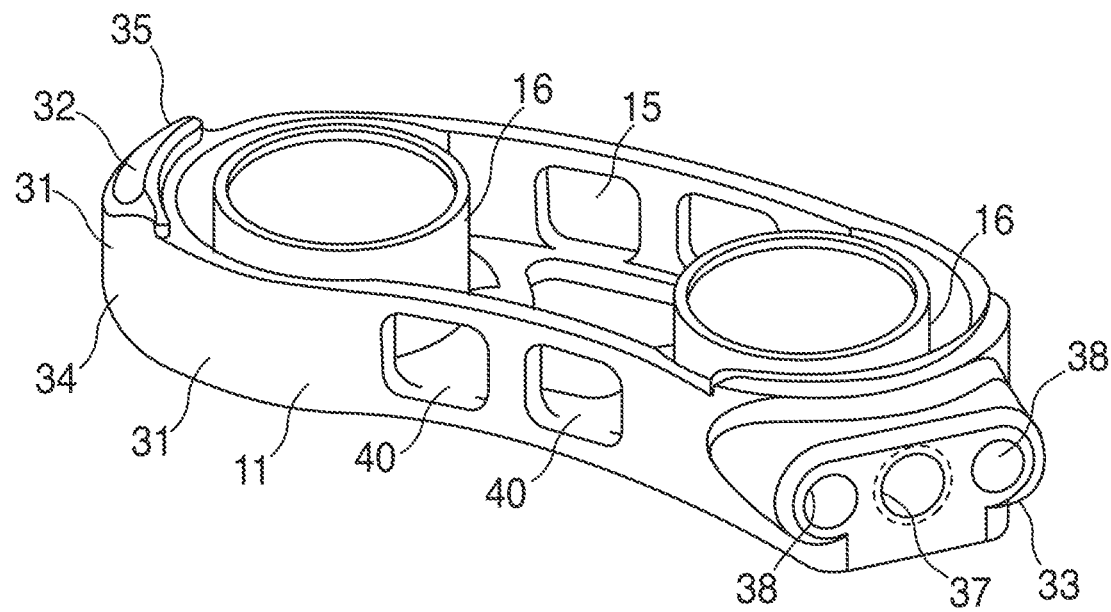
FIG. 5A is a perspective view of a lower part of the implant shown in FIG. 1 with upper portions and bottom face removed.
Figure 5B:
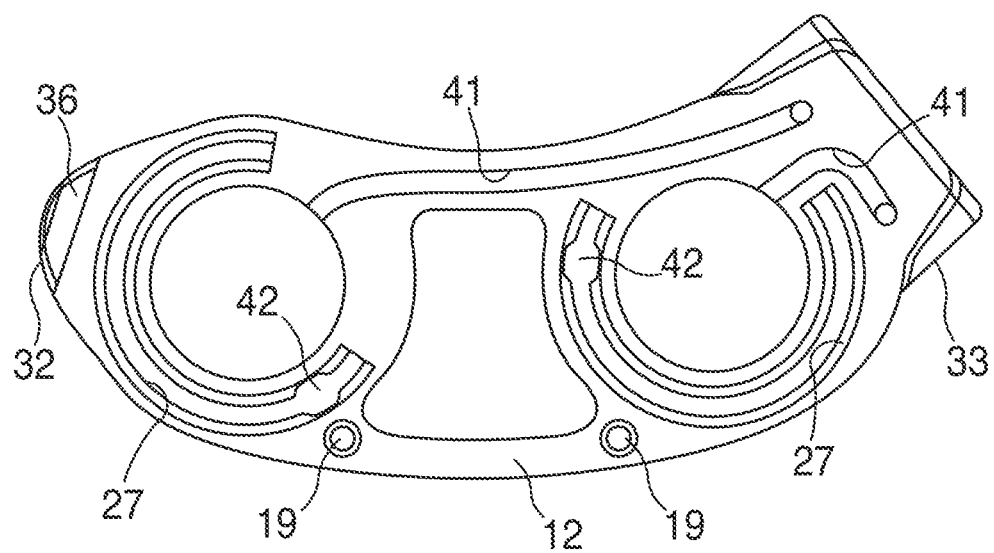
FIG. 5B is a bottom view of the lower portion shown in FIG. 5A.

Additional details of the housing 11 are depicted in FIGS. 5A and 5B. The housing 11 comprises an outer wall 31 and cylinders 16 which are secured to housing base 12. The outer wall 31 supports a leading nose 32 on the distal end and a delivery boss 33 on the proximal end. The leading nose 32 has inwardly directed side tapered faces 34 and top tapered face 35 and bottom tapered face 36. These tapered faces 34, 35 and 36 enable non-traumatic insertion of the implant 10 past neural elements and between the vertebral bodies. The delivery boss 33 contains a delivery tool anchor 37 which allows secure attachment of the implant 10 to a delivery tool (not shown), which is illustrated in co-pending application Ser. No. 11/535,432, filed Sep. 26, 2006, and Ser. No. 11/692,800, filed Mar. 28, 2007 for insertion into a vertebral space. The delivery boss 33 also contains pressure input ports 38 which are used to deliver a pressurized fluid to the interiors of cylinders 16. The outer wall 31 of the housing 11 also provides side openings 40 which provide space for bony in-growth into central cavity 15 in the housing 11 and provide radiolucent openings for the radiographic imaging of the process of bony in-growth. The housing base 12 also contains pressure channels 41 which deliver pressurized fluid from the pressure input ports 38 to the interior of cylinders 16. Although the housing base 12 of implant 10 is depicted with independent pressure channel 41 for each cylinder 16, other embodiments can contain one or more branching pressure channels for delivering pressurized fluid to two or more cylinders 16. As previously mentioned, the housing base 12 also has locking actuator slots 27 which hold and guide the locking actuators 26. The locking actuator slots 27 contain a wider portion, locking actuator opening 42, to enable insertion of the locking actuator 26 into the channels defined by the locking actuator slots 27 in housing base 12 and the locking actuator channels 25 in the bottom end plate 14. The housing base 12 also has optional alignment bosses 19 which align the bottom end plate 14 to the housing 11 via optional alignment holes 9.

Figure 6A:
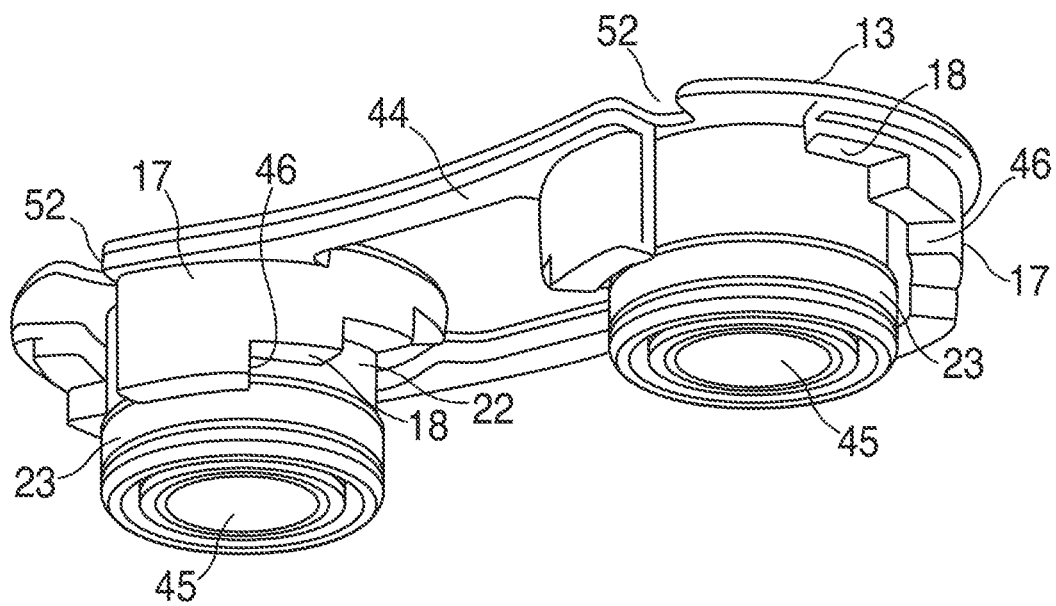
FIG. 6A is a perspective view of the upper portion of the implant shown in FIG. 1 with the lower portion removed.
Figure 6B:
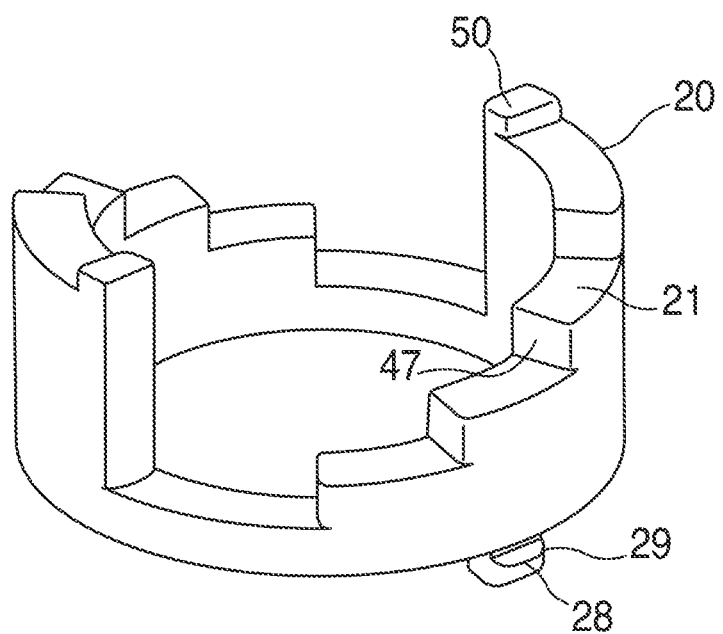
FIG. 6B is an enlarged perspective view of the staircase-like lower lock support shown in FIG. 3.

FIGS. 6A and 6B illustrate further details of the top end plate 13 and the lower lock support 20. The two sets of pistons 22 and upper lock supports 17 are joined by connecting members or struts 44. The pistons 22 have seal bosses 45 on which the seals 23 are mounted. The upper lock supports 17 have tiered lower support surfaces 18 and risers or alignment faces 46. The tiered or stepped support surfaces 18 of the upper lock supports 17 engage the stepped or tiered support surfaces 21 of the lower lock supports 20. The alignment faces 46 of the upper lock support are configured to engage the alignment faces 47 of the lower lock supports 20. The uppermost support surface of the lower lock support 20 has a lock support stop 50 which engages with the lower most alignment faces 46 of the upper lock support to prevent the lower lock support 20 from over rotating as it engages the upper lock support 17. The bottom of the lower lock support also has the locking actuator transfer element 28 which engages the forward end 30 of the spring locking actuator 26 to transfer the actuation force from the locking actuator 26 to the lower lock support 20.

Figure 7:
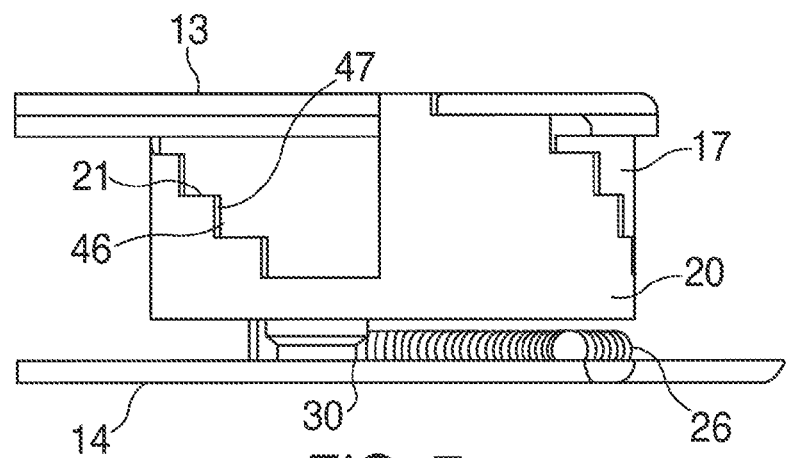
FIG. 7 is a partial side view of one of the locking mechanisms of the implant shown in FIG. 2.
Figure 8A:
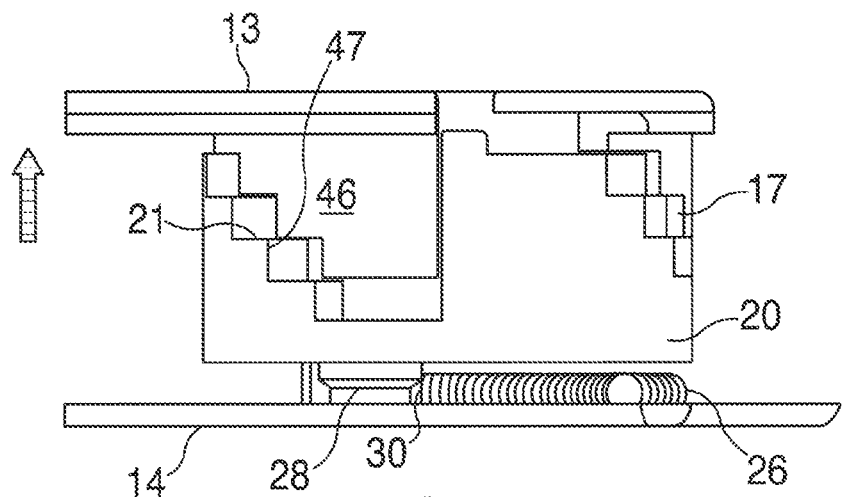
FIGS. 8A-9B are partial side views of the locking mechanism in FIG. 7 shown in different expanded and locked configurations.
Figure 8B:
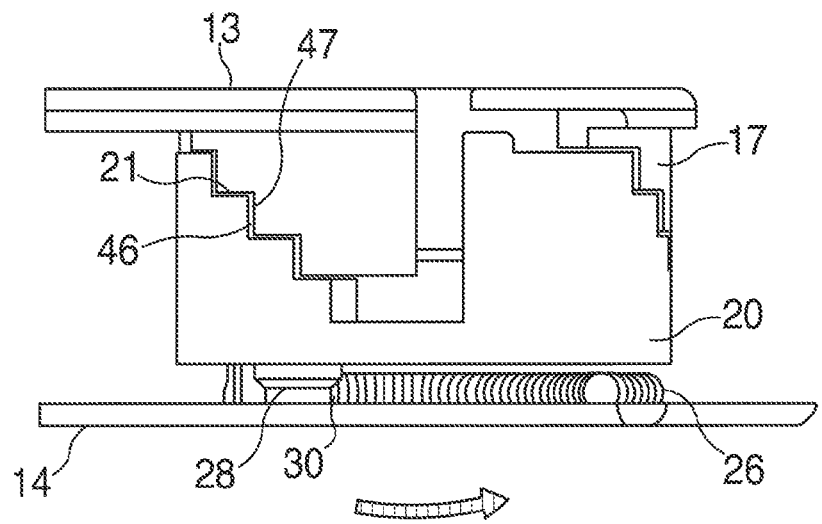
Figure 9A:
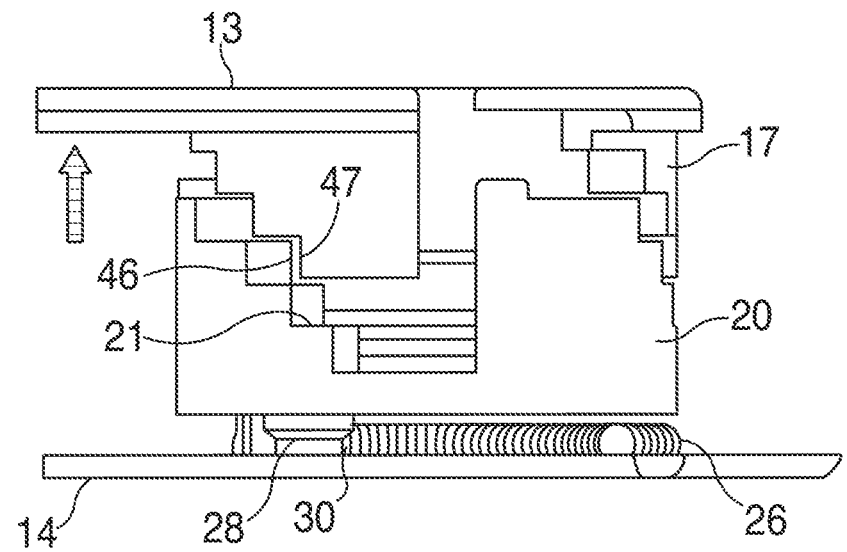
Figure 9B:
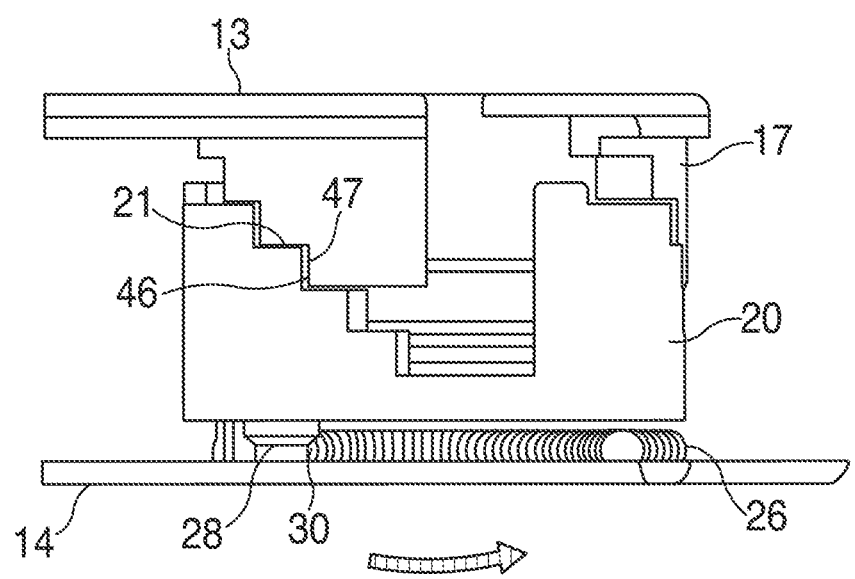
Figure 10A:
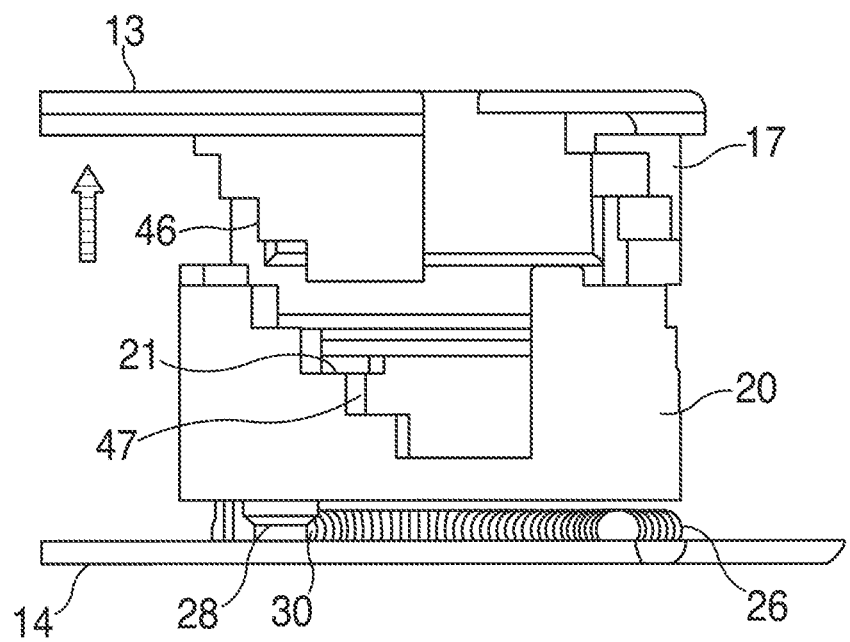
FIGS. 10A and 10B of the locking mechanism illustrate the expanded but unlocked configuration in FIG. 10A and the expanded and locked configuration in FIG. 10B.
Figure 10B:
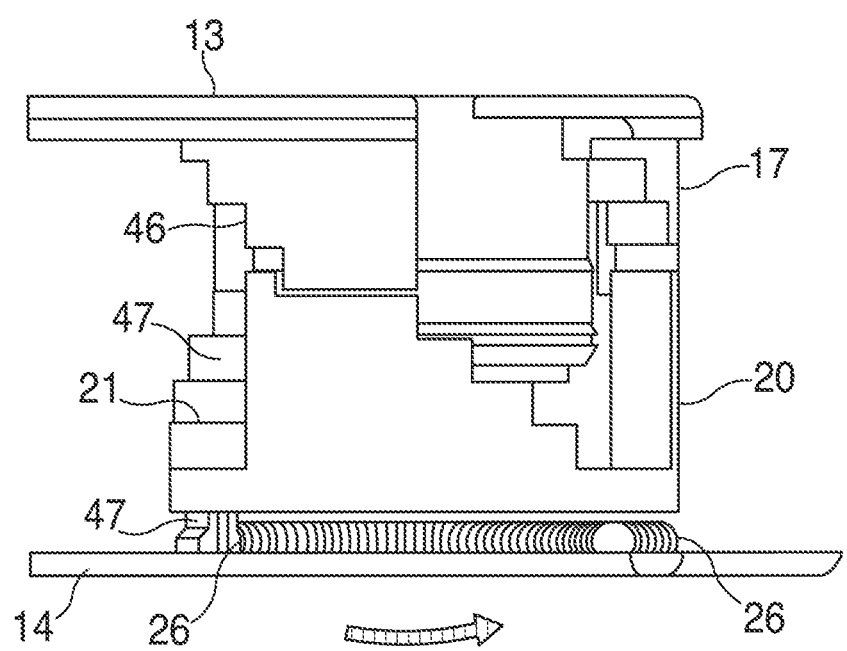

FIGS. 7 through 10B show details of the selectively expanding locking sequence of implant 10 with the housing 11 removed. The collapsed configuration is shown in FIG. 7 with the support surfaces 18 of the upper lock support 17 resting on the support surfaces 21 of the lower lock support 20. The locking actuator 26 is a biasing element, such as a spring, that engages the depending element or locking actuator transfer element 28 to urge the alignment faces of the lock supports in a direction where they contact. Thus, in one exemplary embodiment, the alignment faces 47 of the lower lock supports 20 are forced against the alignment faces 46 of the upper lock support 17. The lock support stops 50 fit within the lower lock stop relief 52 (shown best in FIG. 6A) on the top end plate 13. When the cylinders 16 are pressurized, the pistons 22 raise the top end plate 13 and attached upper lock supports 17 (straight arrow) moving the support surfaces 18 of the upper lock support 17 off of the support surfaces 21 and moving the lower alignment faces 46 past the upper alignment faces 47. When the alignment faces 46 of the upper lock support 17 have cleared the alignment faces 47 of the lower lock support 20, the locking actuators (in this embodiment a compressed coiled spring) engaging the locking actuator transfer element 28 force the lower lock supports 20 to rotate (curved arrow in FIGS. 8B and 9B). The support surfaces 21 of the rotating lower lock supports 20 move to the next lower level of the support surfaces 18 of the raised upper lock supports 17 until the alignment faces 47 of the lower lock supports 20 engage the next level of the alignment faces 46 of the upper lock supports 17. The lower lock support 20 and upper lock support 17 then lock the top end plate 13 at this expanded level. This process repeats itself at each locking level (FIGS. 8A, 8B, 9A, 9B and 10A) until the top level (or somewhere between) is reached as shown in FIG. 10B. At this top level, the locking actuators 26 engage the locking actuator transfer elements 28 and the lower lock supports 20 are rotated so the lowermost alignment surface 46 of the upper lock support 17 engages lock support stop 50 of the uppermost support surface 21 of the lower lock support 20. At this highest locked level only the lowest support surfaces 18 of the upper lock supports 17 and the highest support surfaces 21 are engaged providing all of the locking support. As can be seen from FIGS. 10A and 10B the lowest support surfaces 18 of the upper lock supports 17 and the highest support surfaces 21 of the lower lock supports 20 can be wider than the other support faces to provide sufficient support material when only these two faces are engaged.

Figure 11A:
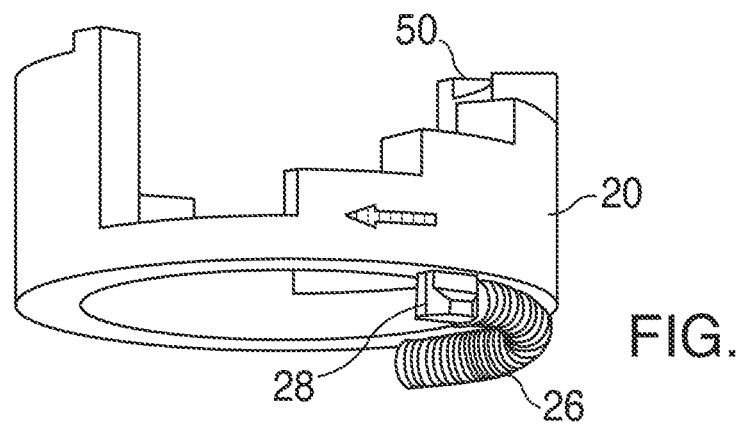
FIGS. 11A and 11B are perspective views of the lower lock support and spring locking actuator illustrating the operation thereof.
Figure 11B:
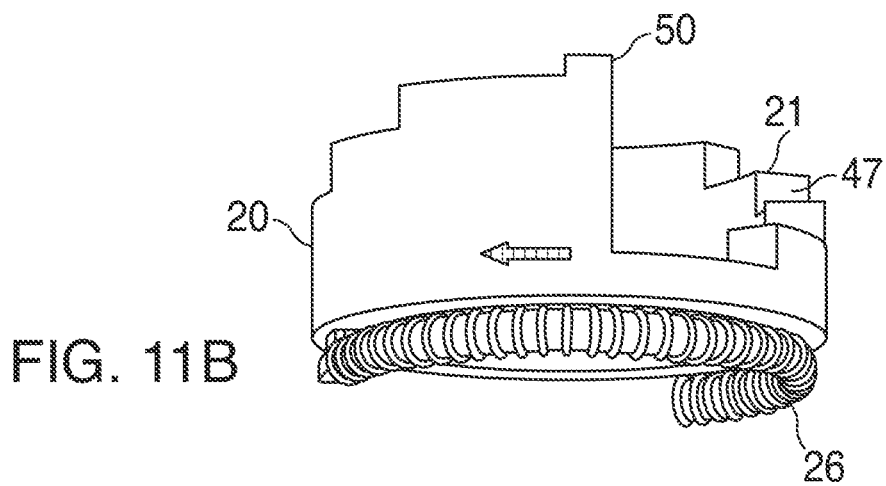

FIGS. 11A and 11B illustrate the operation of locking actuator 26. In this embodiment the spring locking actuator 26 is compressed into an arc beneath the lower lock support 20. One end of the spring locking actuator 26 is constrained by the housing 11 (not shown) and the other is engaged with the locking actuator transfer element 28. When the lower alignment faces 46 of the upper lock support 17 are raised above the upper alignment faces 47 of the lower lock support 20 by the extension of piston 22, the locking actuator 26 pushes against the locking actuator transfer element 28 and rotates the lower lock support 20 in a clockwise direction (arrow) as viewed from above. It should be noted that in the embodiment of the current implant as described thus far, the angular orientation of the tiered upper and lower support surfaces 18 and 21 can vary when there is more than one set of supports. As shown in FIG. 3 the proximal lower support surfaces 21 are oriented clockwise as viewed from above and the distal lower support surfaces 21 are oriented counter-clockwise. This opposite orientation provides enhanced locking support for rotational forces applied to the implant.

Figure 11C:
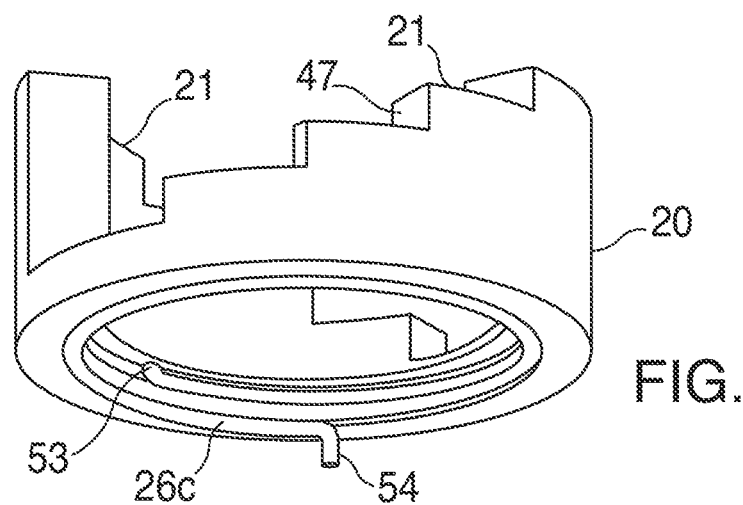
FIG. 11C is a perspective view of an alternative locking mechanism and locking actuator embodying features of the invention.

An alternative locking actuator 26a is shown in FIG. 11C as a torsion spring. This locking actuator 26a has constraining tab 53 secured to the lower lock support 20 and constraining tab 54 secured to the housing 11. Just as the compression spring shown in FIGS. 11A and 11B applies a force to the lower lock support 20 to rotate it, the torsion spring in FIG. 11C does the same. An extension spring would work equally as well as a locking actuator 26a. Spring actuators can be made of an appropriate biocompatible material such as stainless steel, NITINOL, titanium or a suitable polymer. Locking actuators are not limited to springs. A wide variety of mechanisms can be used to actuate the lower lock supports 20, including but not limited to, a linear drive, an externally actuated tensile member, a worm gear, an inflated member such as a balloon or bellows, a magnet, a rotational drive such as a micro motor, a super elastic shape memory element, and the like.

Figure 12A:
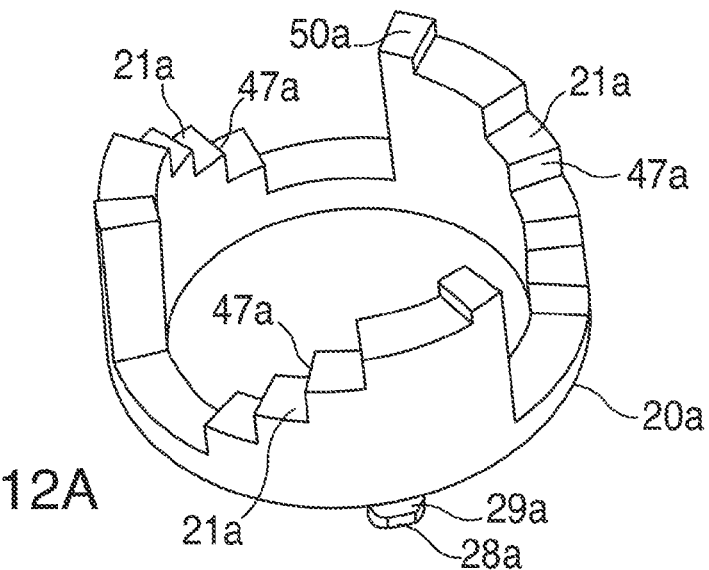
FIGS. 12A-12C are perspective views of alternative lower lock support designs embodying features of the invention.
Figure 12B:
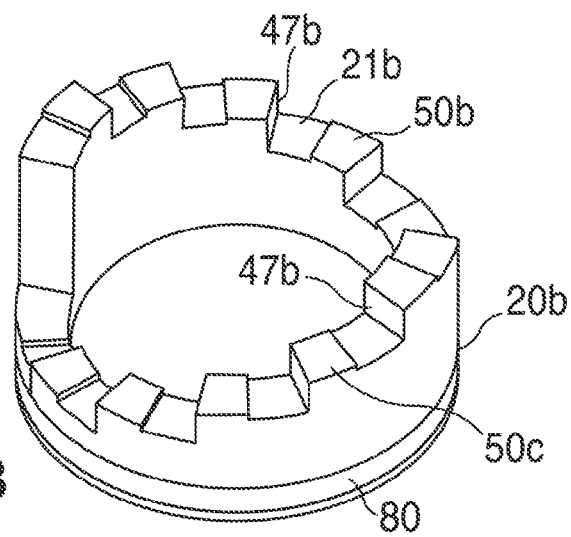
Figure 12C:
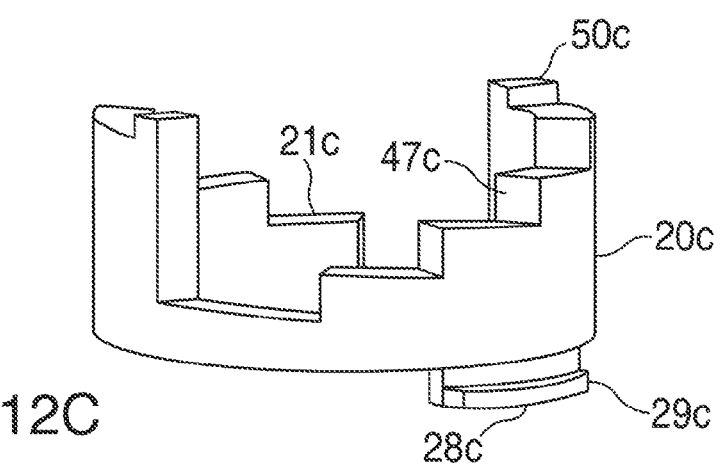

FIG. 12A through 12C show variations of the lower lock support 20 described above. In FIG. 12A a tri-set lock support 20a is shown whereby there are three sets of upper support surfaces 21a, upper alignment surfaces 47a and lock support stops 50a rather than the two sets described above. This tri-set lower lock support 20a has two advantages over the two sets design, 1) there are three support columns rather than two locking the implant 10 in an expanded state thereby creating a more stable lock and 2) the tri-set lower lock support 20a has to move or rotate much less for each locking level. This last advantage is significant when the locking actuator is a spring such as spring locking actuator 26 as this places less strain on the spring to achieve the required locking force at each step. Each lower lock support column will have a corresponding upper lock support column (not shown). The upper support surfaces 21 and lower support surfaces 18 are not limited to two or three sets of surfaces. Any number of sets of support surfaces including a single set may be employed.

FIG. 12B shows an inter-digitating lower lock support 20b. Each of the inter-digitating upper support surfaces 21b on the inter-digitating lock support 20b is paired with an inter-digitating stop 50b which when paired with matching inter-digitating support surfaces and stops of an upper lock support (not shown) prevents the inter-digitating support surfaces 21b from moving relative to the inter-digitating support surfaces of an upper lock support to unlock the implant without the inter-digitating lower support faces first lifting above the inter-digitating stop 50b. This design provides an enhanced locking feature. Upper alignment surfaces 47b are again provided.

Generally the lower support surfaces 18 and the upper support surfaces 21 are horizontal to maximize vertical support in the locked implant. However, the locking support 20c shown in FIG. 12C provides an enhanced locking feature by providing inclined support surfaces 21c which have a slope relative to the horizontal which requires matching inclined lower support surfaces on the upper lock supports (not shown) to be lifted above the inclined upper support surfaces 21c before the upper lock support can be rotated to unlock the implant.

FIGS. 12A and 12C show various lengths of locking actuator transfer elements or depending elements 28. The locking actuator transfer element 28 can vary in length depending on how much engagement is desired between the locking actuator transfer element 28 and the locking actuator slots 27. The locking actuator transfer element 28 includes one or more transfer element tabs 29a and 29c which vertically constrain the lower lock support 20 to the locking actuator slots 27 in the housing 11. The wider locking actuator opening 42 described above (see FIG. 5B) enables insertion of the locking actuator transfer element 28 with transfer element tabs 29a and 29c into the locking actuator slots 27 in housing base 12 at the rotational position where the locking actuator transfer element 28 is aligned with the locking actuator opening 42. In other rotational positions the transfer element tabs are constrained by lateral extensions on the sides of the narrower locking actuator slots 27. In this manner the locking actuator transfer element 28 provides both the function of transferring force from the locking actuator 26 to the lower lock support 20 as well as constraining the lower lock support 20 to the housing 11. This later function prevents the frictional forces between the lower alignment faces 46 and the upper alignment faces 47 created by the biased spring locking actuator 26 from lifting the lower lock support 20 along with the upper lock support 17 when the upper lock support 17 is lifted by the piston 22.

As an alternative to the locking actuator transfer element 28, the embodiment shown in FIG. 12B depicts a locking actuator guide channel 80. This locking actuator guide channel 80 engages a tensile member (not shown) which transfers actuation force from the locking actuator 26 to the lower lock support 20. Tensile members can be any of a number of known elements such as sutures made of polymers or natural materials, metal cable, plastic or metal rod and the like.

Figure 13A:
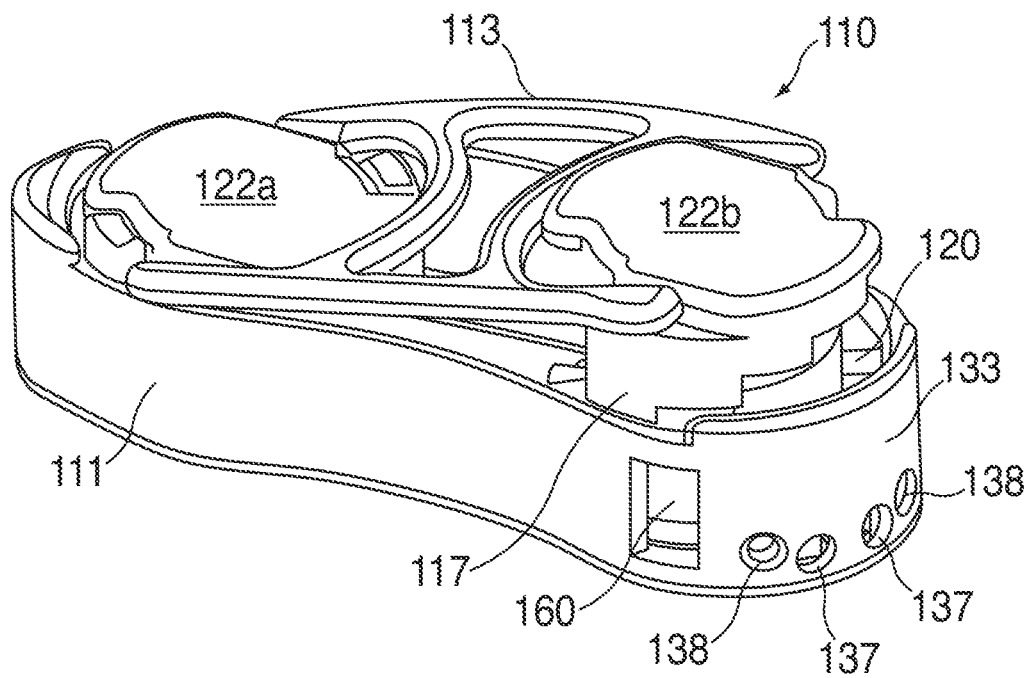
FIGS. 13A-13B are perspective and side views respectively of an alternative implant embodying features of the invention which has an articulating top end plate.
Figure 13B:
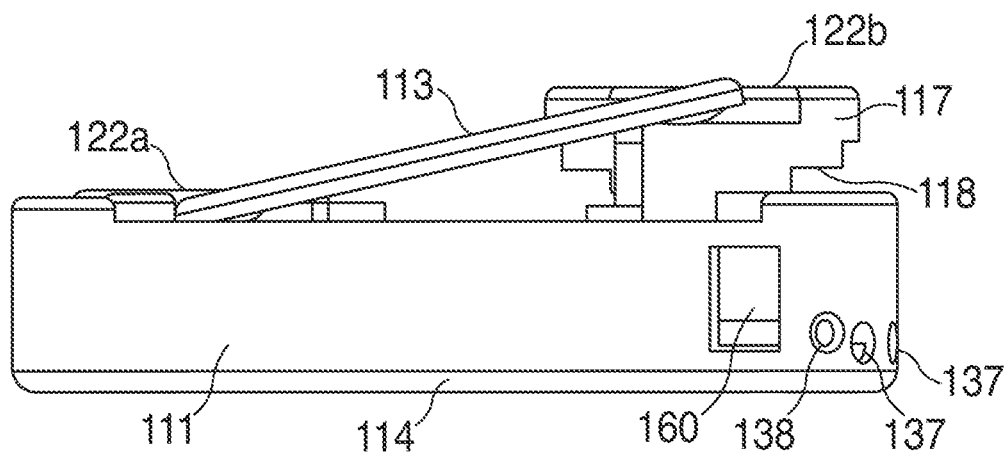

FIGS. 13A and 13B illustrate an alternative design of an implant 110 embodying features of the invention. The implant 110 has independent actuation of the distal piston 122a and proximal piston 122b. The two pistons 122a and 122b are interconnected by an articulating top end plate 113 which allows independent lift and locking of each side of the implant 110. This independent lift and locking of both ends of the implant 110 enables the implant to conform to intervertebralend plates that have uneven lateral heights between them. Further, this independent lift and locking allows the implant 110 to be used to create varying lateral heights between vertebralend plates which can be useful to compensate for a scoliosis in the spine.

Implant 110 has a housing 111 which has an alternative delivery tool anchor 160 located in it as well as alternative pressure input ports 137. A variety of anchor designs or pressure ports can be used with any of the embodiments of the current device without departing from the scope of this invention. Lock and unlock access ports 138 are also located on this housing 111. These ports are used to guide lock and unlock mechanisms (not shown) which can be manipulated externally to the implant 110 to actuate the lower lock support 120 to not only move it under the upper lock support 117 to hold the piston 122b and articulating end plate 113 in an expanded position, but also to move the lower lock support 120 away from the upper lock support 117 to allow the piston 122b and articulating end plate 113 to collapse back into the housing 111. This later action may be desirable to remove the implant 110 from or reposition the implant within the intervertebral space. A variety of lock/unlock mechanisms can be used with the current invention such as but not limited by, a tensile member including suture thread and metallic cable, a compressive member such as a metallic or polymer rod, pressurized fluid, a rotating drive, a super elastic shape memory element, and the like.

Figure 14A:
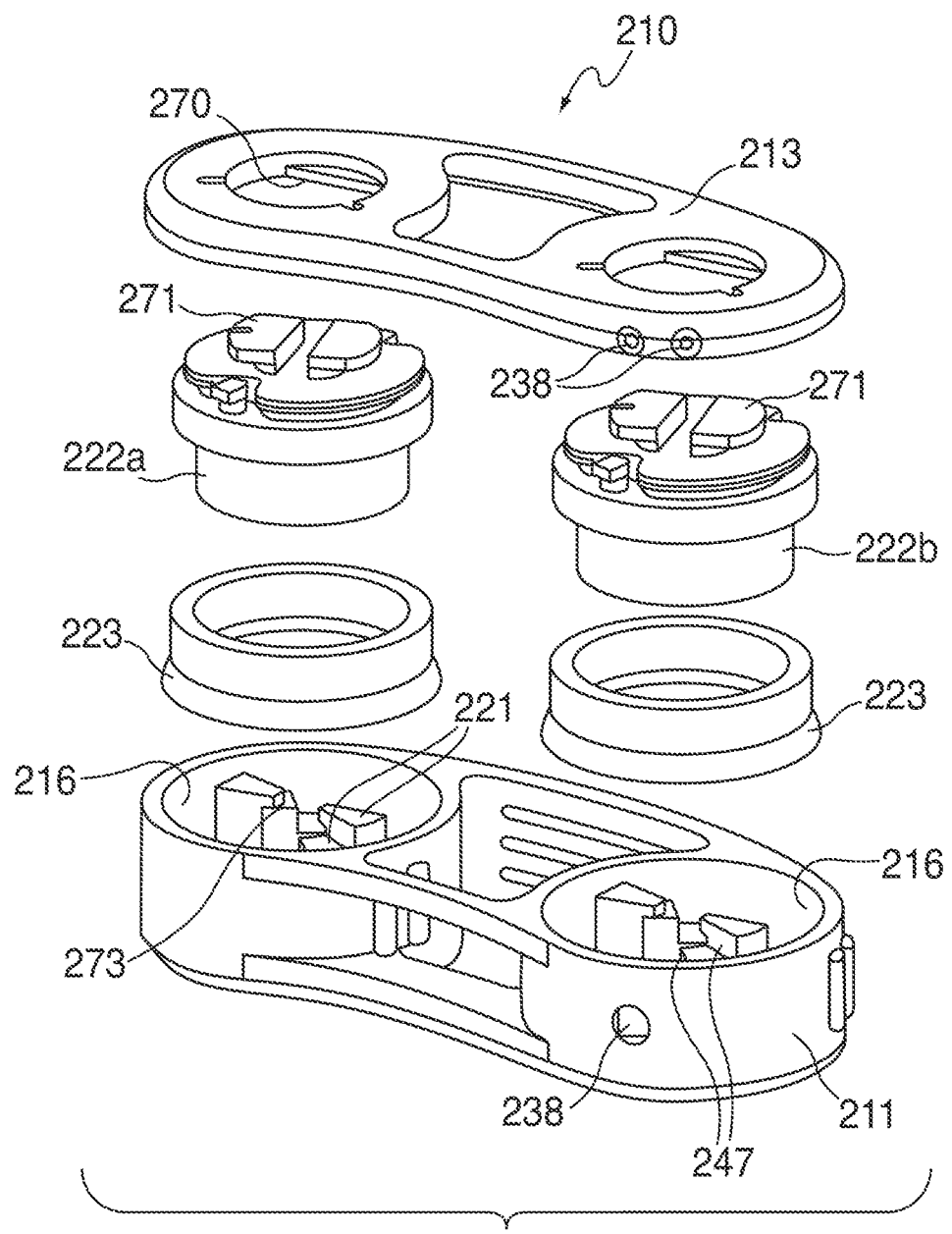
FIG. 14A is an exploded perspective view of yet another alternative implant embodying features of the invention which has the lower lock supports within the extendable pistons.
Figure 14B:
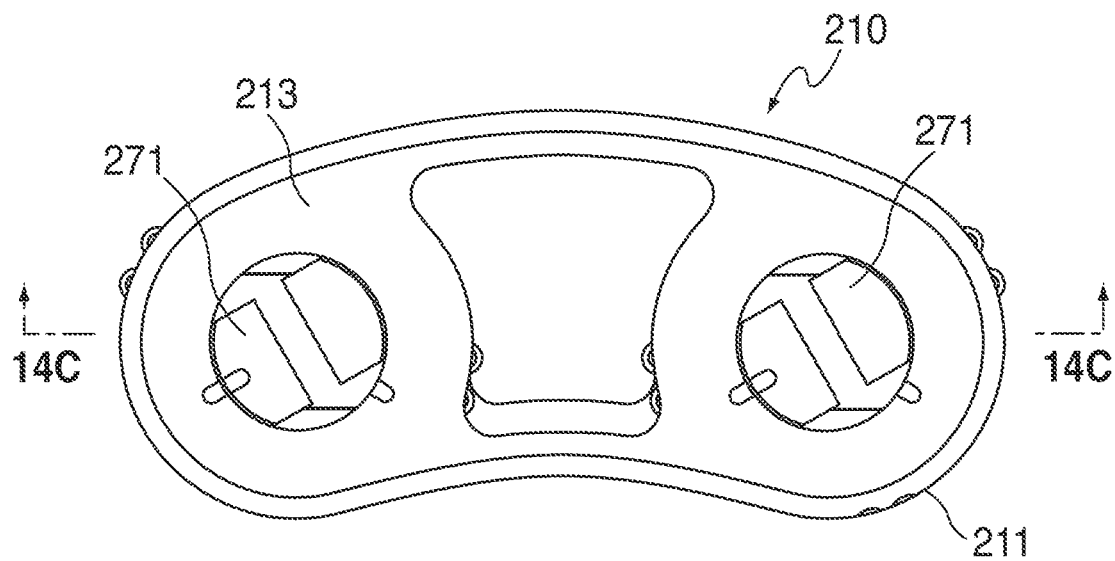
FIG. 14B is a top view of the implant shown in FIG. 14A.
Figure 14C:
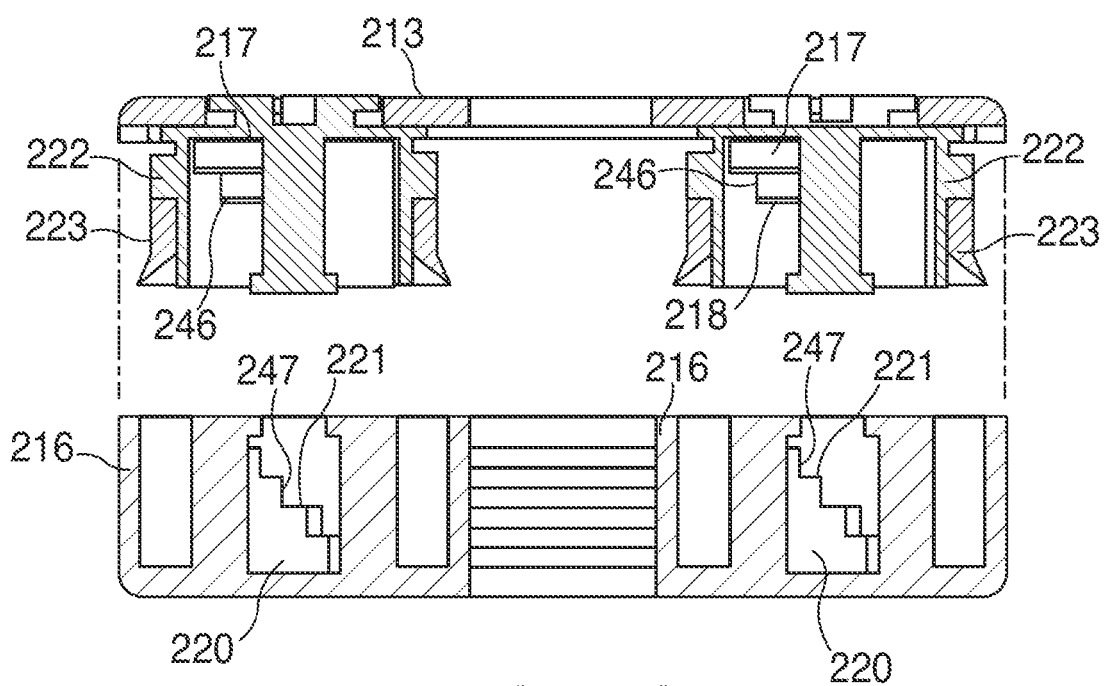
FIG. 14C is a side cross-sectional view through line 14C-14C of the implant shown in FIG. 14B.

FIGS. 14A-14C depict yet another alternative implant 210 that embodies features of the invention. Implant 210 has an interfacing top plate 213 which connects to separate and freely rotating pistons 222 via the piston capture plate 270 on the interfacing top plate 213 and the piston heads 271 on the rotating pistons 222ab. The rotating pistons 222ab also interiorly contain upper lock supports 217 with support faces 218 and alignment faces 246. Seals 223 are mounted on the rotating pistons 222ab and the seals 223 and rotating pistons 222ab fit into internal cylinders 216 that are located on the housing 211. The internal cylinders 216 have lower lock supports 220 with support surfaces 221 and alignment faces 247 as well as lower retaining features 273. The housing 211 also contains one or more pressure input ports 238.

In use, the implant 210 is inserted into the intervertebral body space in a collapsed state and fluid pressure is delivered through the pressure input port(s) 238 to the internal cylinder(s) 216 to raise the seal(s) 223 and rotating piston(s) 222ab out of the internal cylinder(s) thereby raising the interfacing top plate 213 and expanding the implant 210. Once the rotating pistons 222ab have been raised such that the lower alignment faces 246 of the upper lock supports 217 have cleared the upper alignment surfaces 247 of lower lock supports 220, an actuator (not shown) rotates the rotating pistons 222ab such that the lower support surfaces 218 of the upper lock supports 217 are moved above the upper support surfaces 221 of the lower lock supports 220, to thereby lock the implant 210 in the expanded configuration. The actuator can be one or more tensile members such as suture threads or cables that extend from the user into the implant 210 through the lock and unlock access ports 238 on the interfacing top plate 213 to the piston head 271. Applying tension to one or more tensile members when the piston is in an extended configuration will rotate the piston heads 271 such that the support surfaces 218 of upper lock supports 217 are moved above the support surfaces 221 of the lower lock supports 220 thereby locking the implant 210. Alternatively or in addition to applying tension to lock the implant 210 in an expanded configuration, applying tension to one or more tensile members will rotate the piston heads 271 such that the lower support surfaces 218 are moved away from the upper support surfaces 221 thereby unlocking the implant 210 and allowing the rotating pistons 222ab to seat back into the internal cylinders 216 such that the implant 210 is once again in a collapsed configuration.

Figure 15:
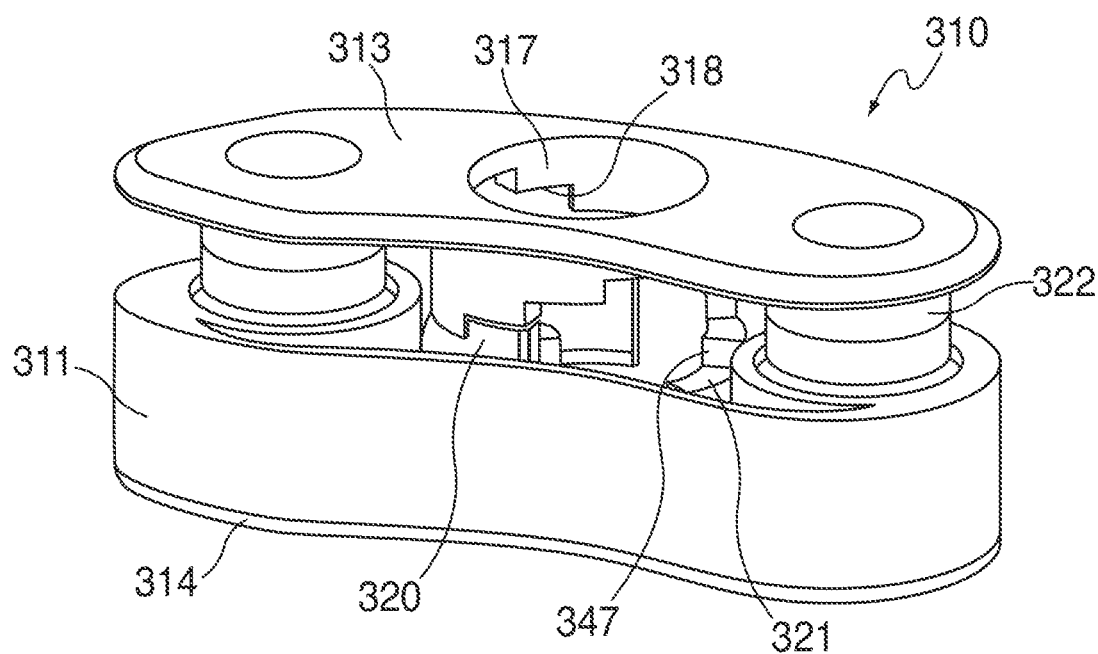
FIG. 15 is a perspective view of an alternative implant design having features of the invention wherein the locking mechanism surrounds a central opening in the top end plate.

FIG. 15 illustrates an alternative implant design 310 embodying features of the invention which has a housing 311, top end plate 313 and pistons 322 similar to the prior embodiments. This implant 310 has upper lock supports 317 and lower lock supports 320 within a central portion of the implant. The upper lock supports 317 are secured to the top end plate 313 and the lower lock supports 320 are secured to the base 314 with depending elements (not shown) as was described above and are moved as in the prior embodiments.

Figure 16:
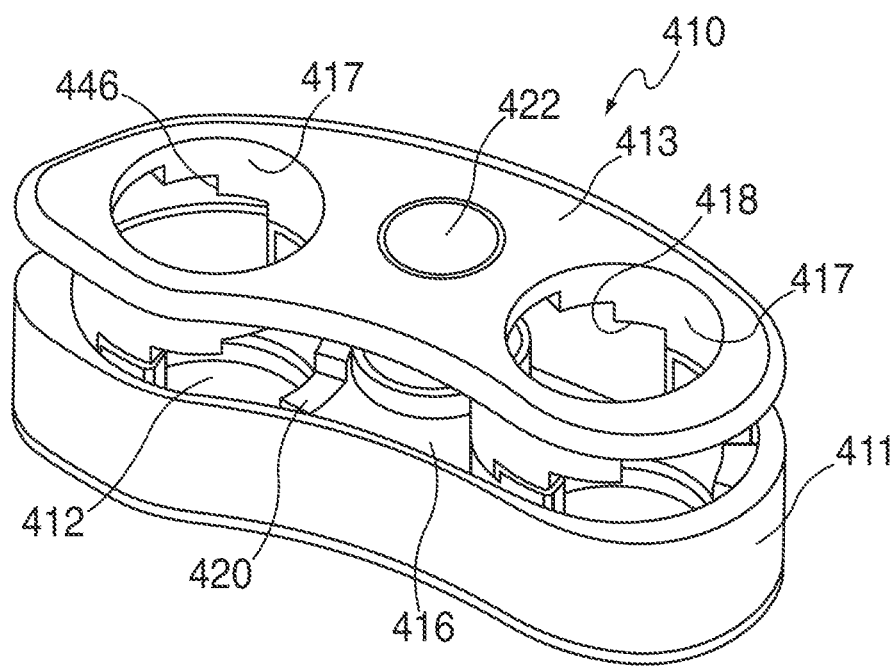
FIG. 16 is a perspective view of an alternative implant design having features of the invention wherein the expanding piston is centrally located and locking mechanisms are provided on both sides of the expanding piston.

FIG. 16 illustrates an alternative implant design 410 embodying features of the invention which has a housing 411, top end plate 413 and a centrally located piston 422 similar to the prior embodiments. This implant 410 has upper lock supports 417 and lower lock supports 420 distal and proximal to the centrally located cylinder 416 and piston 422. The upper lock supports 417 are secured to the top end plate 413 and the lower lock supports 420 are secured to the base 412 and are moved as in the prior embodiments via depending elements (not shown) as was described above.

Figure 17:
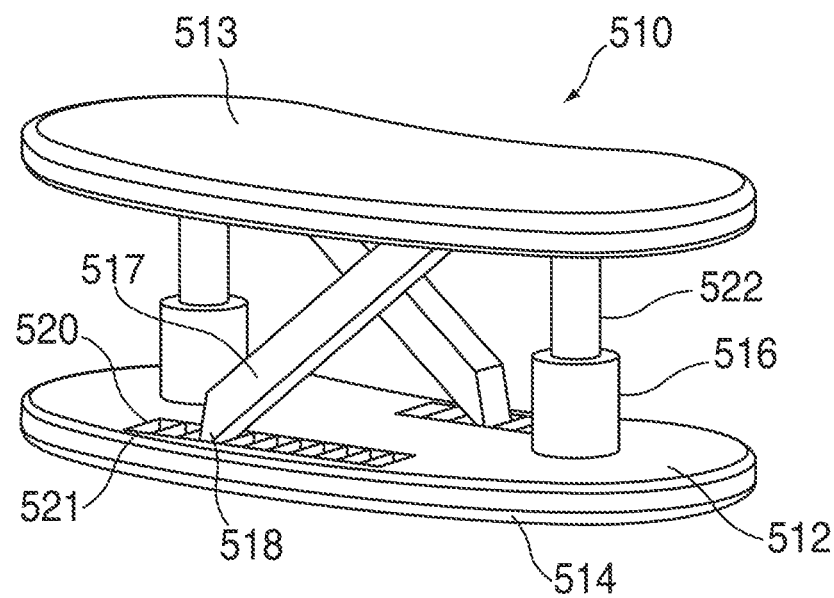
FIG. 17 is a simplified schematic illustration of an alternative implant design having ratchet and pawl locking members between the top and bottom plates of the implant.

FIG. 17 shows another alternative implant 510 which has a pair of pistons 522 and which has a locking support system which includes ratchets 521 on the base 512 and pawls 517 pivotally mounted to and depending from the top end plate 513. Expansion of the pistons 522 causes the free ends 518 of pawls 517 to engage recesses 520 in the ratchets 521 so as to lock the top end plate 513 in an extended configuration.

Figure 18:
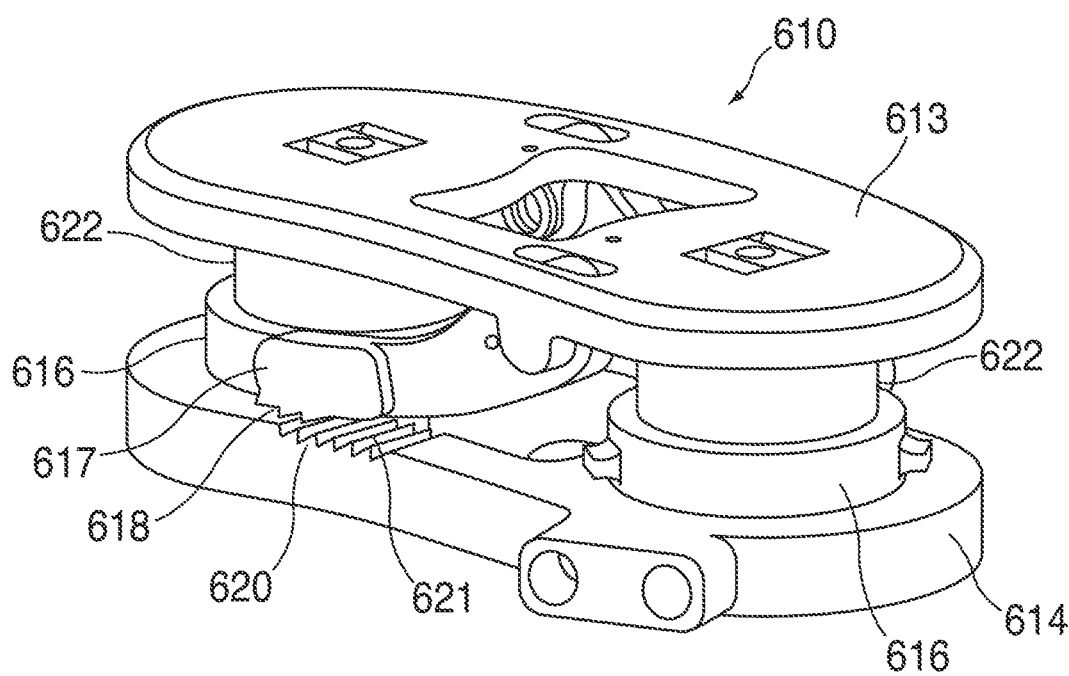
FIG. 18 is a perspective view of an alternative implant design with ratchet and pawl locking members between the top and bottom plates of the implant.

FIG. 18 illustrates another alternative implant design 610 which is similar to that shown in FIG. 17. In this embodiment the free end of the pawl 617 has a plurality of teeth 618 to provide greater effective contact between the pawl 617 and the ratchet 621 for locking of the implant 610.

Figure 19:
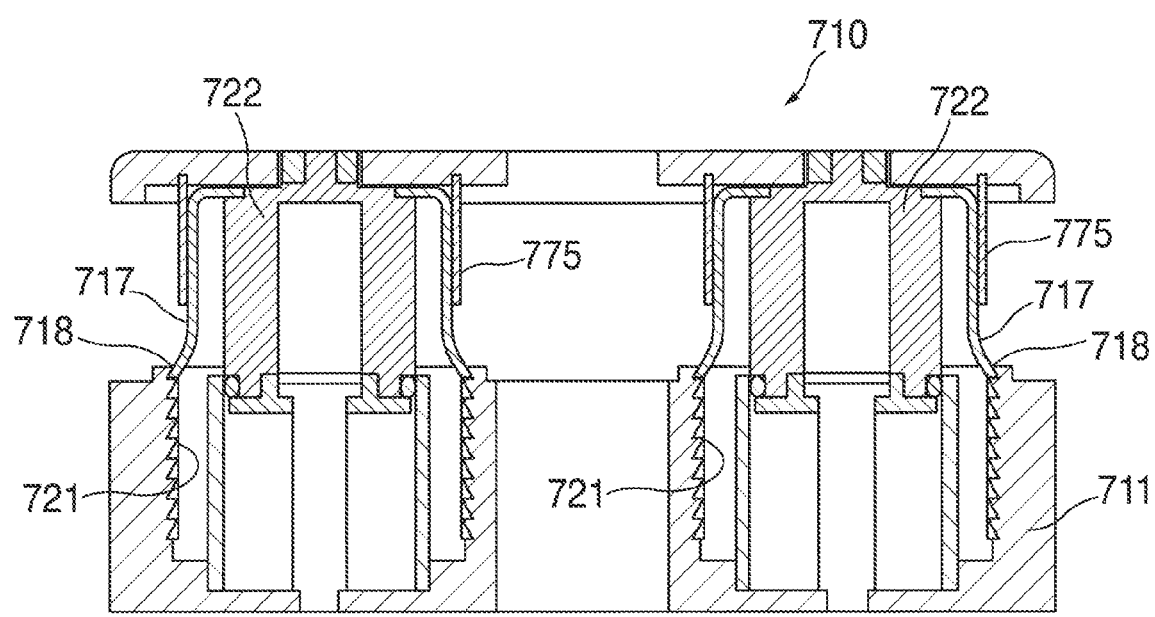
FIG. 19 is a cross-sectional perspective view of an implant design with ratchet and cantilevered spring members between the top and bottom plates of the implant.

FIG. 19 is a cross section embodiment, showing implant 710 embodying features of the invention. In this embodiment the pistons 722 are surrounded by upper lock support 717 which has at least one cantilever extension ending at the support surface 718. The support surfaces 718 are captured by the recessed support surfaces 721 which are located on the inner wall of the housing 711. Once the pistons 722 are expanded in an upward direction, the support surfaces 718 of the upper lock support 717 engages the recessed support surfaces 721 locking the implant 710 in place. The upper lock support 717 can be rotated relative to the piston 722 and housing 711 to disengage the support surfaces 718 from the support surfaces 721 to unlock the implant 710 and lower the pistons 722 as needed. Alternatively the implant 710 can be unlocked by rotating the upper lock support constraints 775 relative to the upper lock support 717 to press on the cantilever extensions and disengage the support surfaces 718 from the support surfaces 721.

FIGS. 20A-31 illustrate a variety of suitable means for locking extendable members such as pistons in extended configurations. FIGS. 20A, 20B, 21A, 21B, and 22-31 show variations of lower lock supports and upper lock supports. In each of these variations there are support surfaces on the lower lock supports which engage support surfaces on the upper lock supports.

In FIGS. 20A and 20B support surfaces 818 comprise grooves set into the upper lock support 817. The lower lock support 820 is a U-shaped tong which is configured to advance (as indicated by the arrow in FIG. 20A) towards the upper lock support 817 and to engage one of the grooves with its upper support surface 821 for locking an implant not shown in these drawings. Lower lock support 820 is withdrawn (as indicated by the arrow in FIG. 20B) from the groove to disengage the lower lock support and unlock the implant.

In the variation shown in FIG. 21A, the lower lock support 920 is a plate with an upper lock clearance opening 970 that is shaped to allow passage of the cylindrical flat-sided upper lock support 917 through the lower lock support 920 (arrow). As shown in FIG. 21B, once the lower lock support 920 is positioned at the desired location it can be rotated approximately 90° (arrow) to engage the support surfaces of the lower lock support 920 with the support surfaces 918 of the upper lock support 917. The shape of the upper lock support 917 and mating upper lock clearance opening 970 on the lower lock support 920 are not restricted to the profile shown in FIGS. 21A and 21B nor is the locking actuation restricted to 90° rotation of one of the elements but can vary to any number of shapes that allow passage in one configuration but constraint when one of the elements is moved to another configuration.

Figure 22:
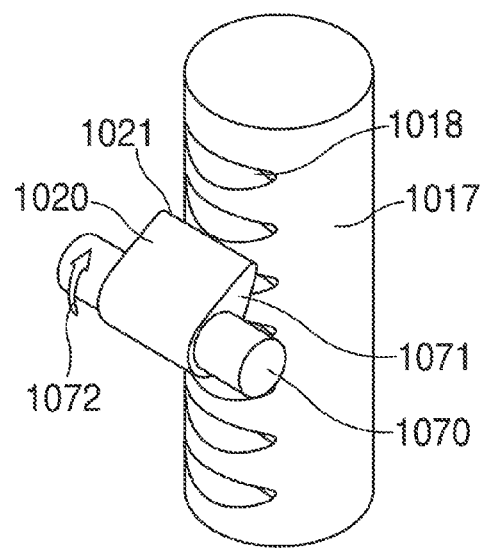

In FIG. 22, the upper lock support 1017 is a cylinder with notches cut to create support surfaces 1018. The lower lock support 1020 is a pivoting pin 1070 with a pawl 1071 for the lower support surface 1021. In the configuration shown, the support surface is biased as indicated by the arrow 1072 to allow the upper lock support 1017 to rise with an expandable member of an implant and to prevent the upper lock support from dropping. This allows the device to lock at each level when the subsequent support surface 1018 of the upper lock support 1017 engages the support surface 1021 of the lower lock support 1020. In this variation having features of the present invention, the upper lock support 1017 can also be lowered by moving the pivoting pin 1070 of the lower lock support 1020 away from the upper lock support 1017 to disengage the support surface 1021 from the support surface 1018.

Figure 23:
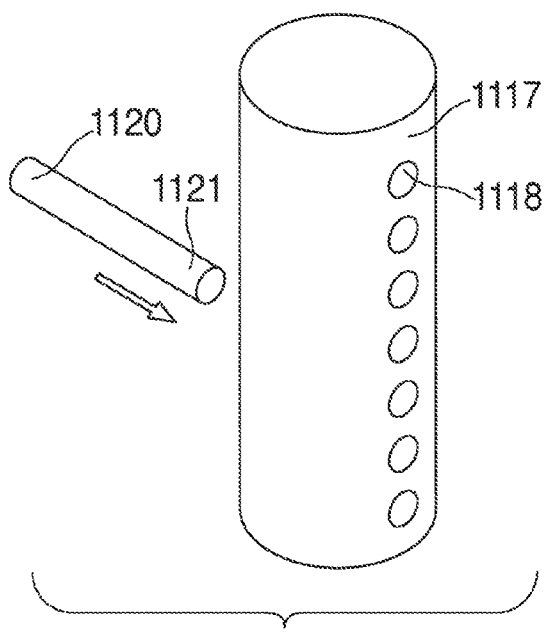

FIG. 23 shows yet another embodiment having features of the invention where the lower lock support 1120 is a pin configured to engage (arrow) support surfaces 1118 located in the upper lock support 1117. The lower lock support 1120 does not have to engage the full thickness of the upper lock support 1117 as shown in this figure, nor does the support surface 1118 have to extend through the entire thickness of the upper lock support 1117 but rather can engage any portion of the upper lock support 1117 that is sufficient to lock an implant in position. This embodiment also allows a variety of shapes of pins 1120 and matching support surfaces 1118.

Figure 24:
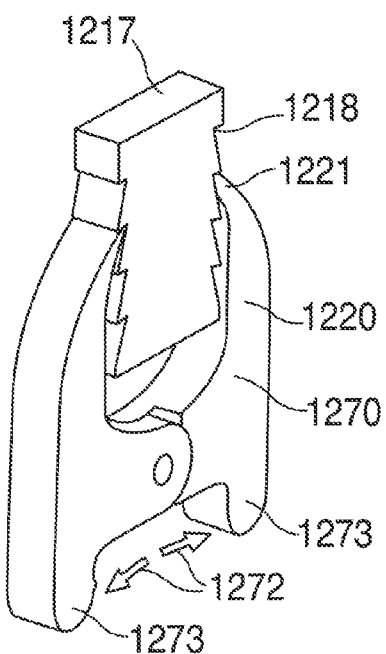

In FIG. 24 the lower lock support 1220 is a grip with two pivoting jaws 1270, the ends of which have support surfaces 1221. The upper lock support 1217 has a series of notches which have the support surfaces 1218. A lock actuator such as a compressive spring (not shown) can apply force (as shown by the arrows 1272) to the grip base extensions 1273 to lock the device. This variation having features of the invention allows the upper lock support 1217 to move upwards but prevents downward motion thereof. Downward motion of the upper lock support 1217 can be allowed by reversing the force on grip base extensions 1273.

Not all locking systems embodying features of the invention require the engagement of support surfaces of the upper lock supports directly on top of the support surfaces of the lower lock supports. A frictional support can be created to lock the device as shown in FIGS. 25 through 32.

Figure 25:
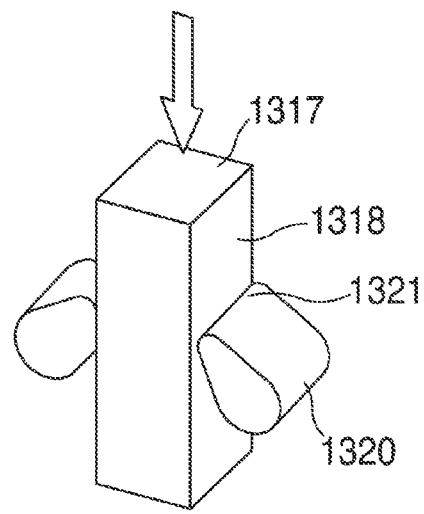

In FIG. 25 the upper lock support 1317 has one or more flat surfaces as the support surfaces 1318. The lower lock support 1320 has one or more pivoting pawls that have a support surface 1321 that engage the support surface 1318 and supports a load (arrow).

Figure 26:
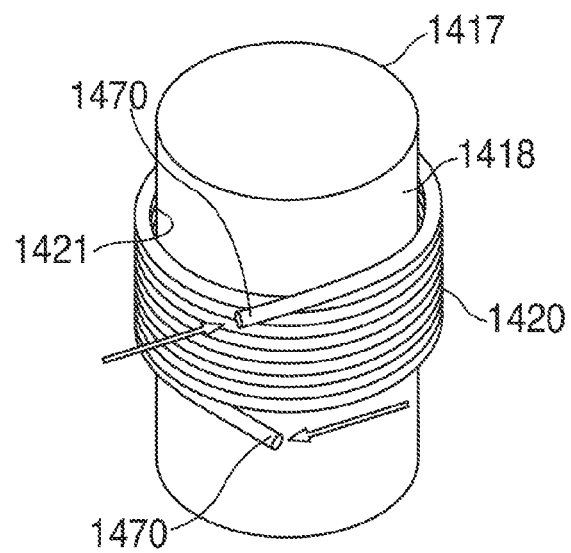

In FIG. 26 the upper lock support 1417 has an exterior support face 1418 which is gripped by the support face 1421 on the inner diameter of the wrapped lower lock support 1420. This lower lock support 1420 can be a torsion spring that in its free state grips the upper lock support 1417 and releases the upper lock support when a force (arrows) is applied to one or more of its ends 1470 as shown to increase the spring's inner diameter. The reverse is possible where in its free state the lower lock support 1420 allows movement of the upper lock support 1417 inside the inner diameter. When a tensile force is applied to the ends 1470 to reduce the inner diameter, the lower lock support grips the support surface 1418 of the upper lock support 1417 to lock the implant.

Figure 27A:
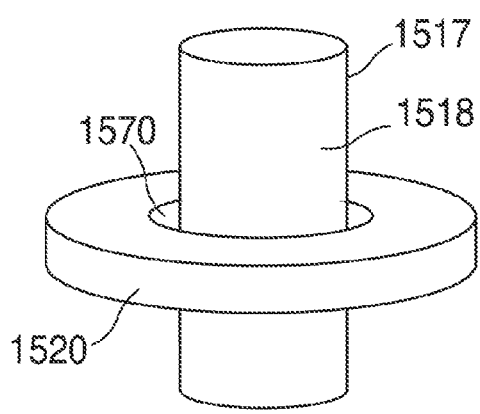
Figure 27B:
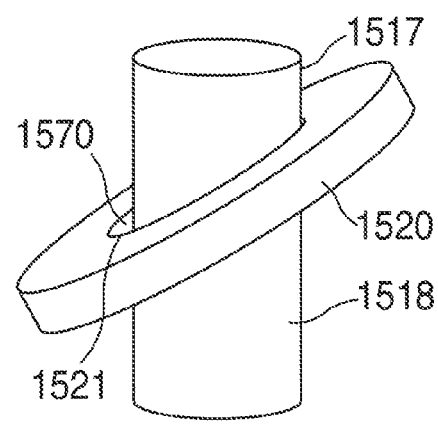

FIGS. 27A and 27B show another variation which can be described as a canted washer type device. The lower lock support 1520 is a plate with an upper lock clearance opening 1570 which allows relative movement of the upper lock support 1517 as shown in FIG. 27A. When the lower lock support 1520 is canted as shown in FIG. 28B, the edge of the upper lock clearance opening 1570 comprises a lower support surface 1521 which engages the upper support surface 1518 which is the outer surface of the upper lock support 1517 locking it relative to the lower lock support 1520.

Figure 28:
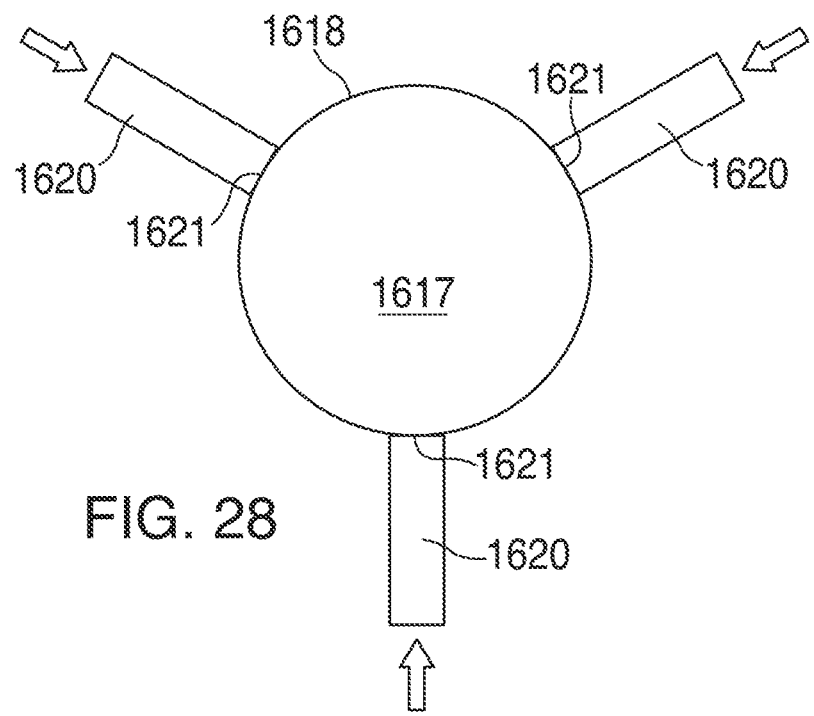

Yet another variation of the gripping lock of the current invention is shown in FIG. 28. In this variation the lower lock support 1620 comprises one or more jaws which have support surfaces 1621 that are configured to be forced against the support surface 1618 of the upper lock support 1617 to produce friction to lock the device in place.

Figure 29:
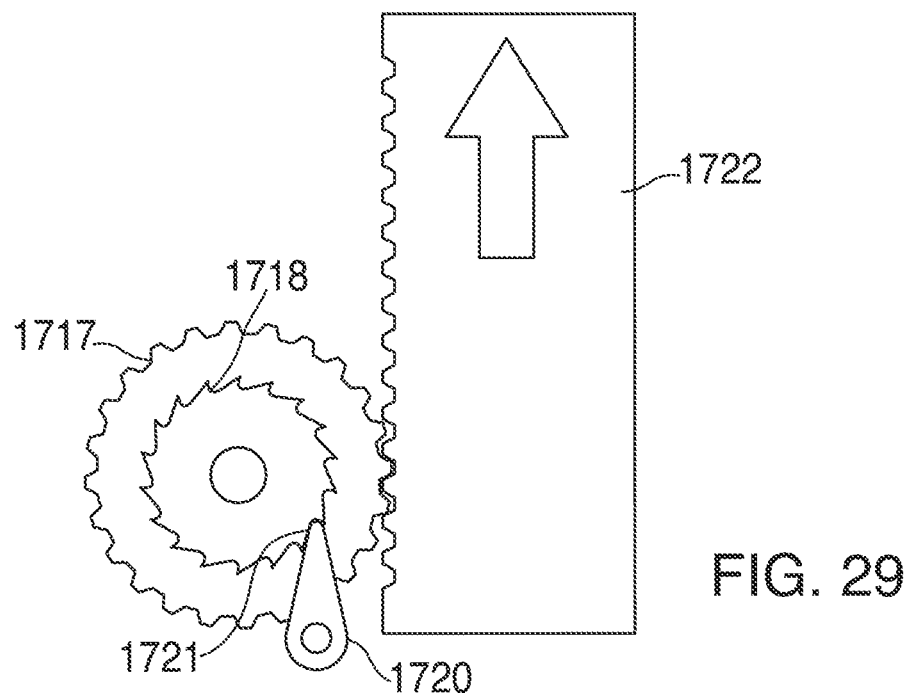

FIG. 29 illustrates a lower lock support 1720 which comprises a pivot and pawl as has been detailed above. The end of the pawl comprises a lower support surface 1721 which engages an upper support surface 1718 on the upper lock support 1717. In this embodiment the upper lock support 1717 is rotated counter clockwise by an expanding element (not shown). This rotation in turn raises the piston 1722 which expands the implant. In this manner the upper lock support 1717 is integrated into the lifting mechanism to engage the lower lock support 1720 and lock the implant as it expands.

Figure 30:
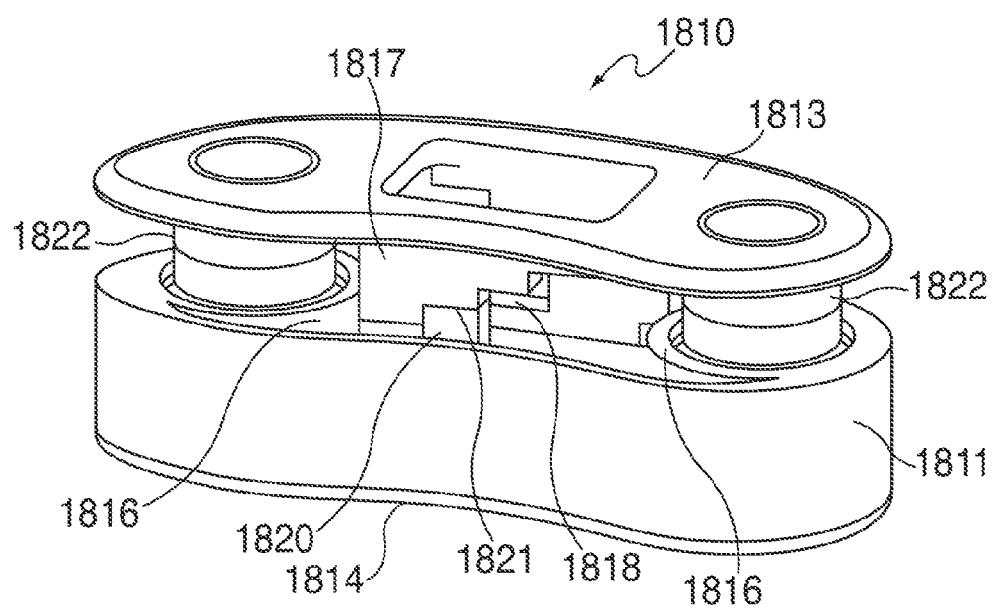
FIG. 30 is a perspective view of yet another alternative implant design having features of the invention wherein the locking mechanism has straight upper and lower interfitting lock supports.

FIG. 30 illustrates yet another alternative implant 1810, similar to that shown in FIG. 1 except that the upper locking member 1817 and lower locking member 1818 have a linear shape rather than the arcuate shape of the prior embodiments. The implant 1810 generally has a housing 1811, a top plate 1813, a bottom plate 1814, pistons 1822 and cylinders 1816. The upper locking member 1817 has support surfaces 1818 and the lower locking member 1820 has support surfaces 1821. The implant 1810 has a locking actuator (not shown).

FIGS. 31A-31G illustrate another implant 1910 embodying features of the invention which have upper locking members 1917 with grooves 1970 having support surfaces 1918 and lower locking member 1920 with locking surfaces 1921. The lower locking member 1920 is a wire-form which encircles the exterior of both upper locking members 1917 and is configured to seat within the grooves 1970. Expansion of the lower locking member 1920 (arrows in FIG. 31B) by the locking actuator (not shown) causes the lower locking member 1920 to be pulled out of the groove 1970 and allows the upper locking member 1917 to rise with the expansion of the implant. Release of this expansion of the lower locking member 1920 (arrows in FIG. 31A) allows the lower locking member 1920 to seat back into the groove 1970 locking the implant 1910.

Figure 31A:
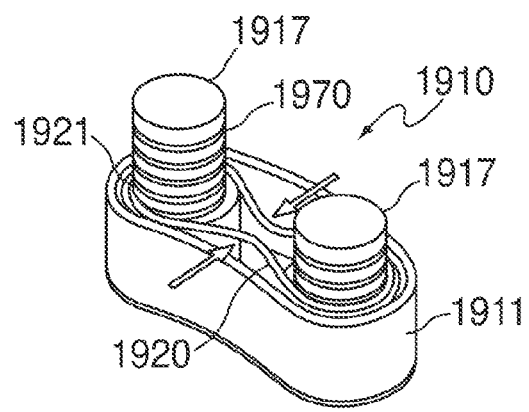
FIG. 31A-31G illustrate an alternative implant locking mechanism in which a wire-form surrounds a pair of upper support members with grooves configured to receive the wire-form.
Figure 31B:
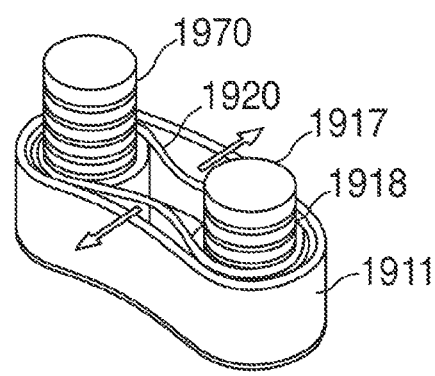
Figure 31C:
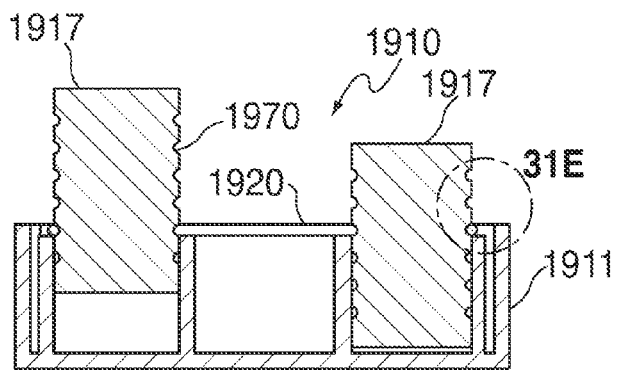
Figure 31E:
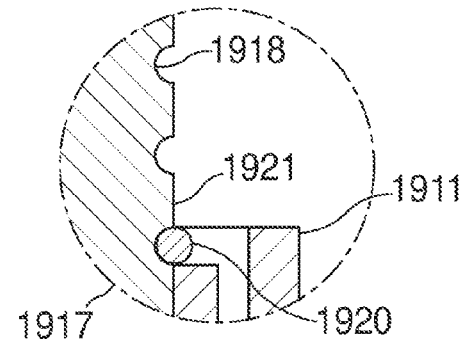
Figure 31D:
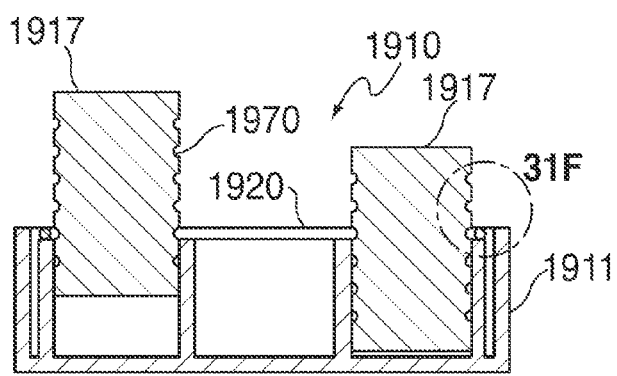
Figure 31F:
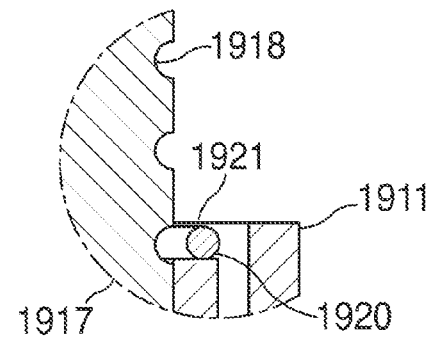
Figure 31G:
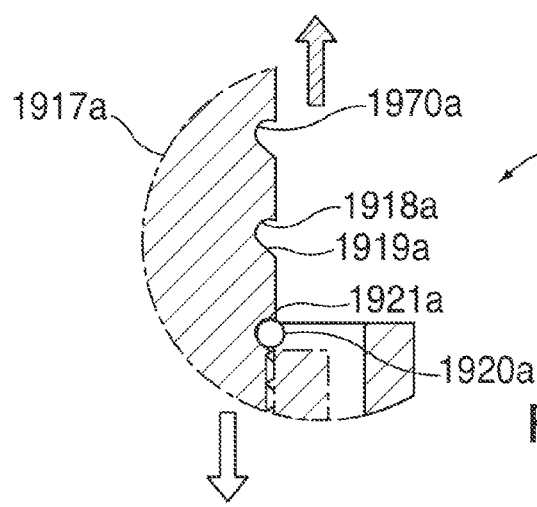

FIG. 31G illustrates a detail of an alternative implant 1910a embodying features of the invention which have upper locking members 1917a with grooves 1970a having support surfaces 1918a and lower locking member 1920a with locking surfaces 1921a. The lower locking member 1920a is a wire-form which encircles the exterior of both upper locking members 1917a and is configured to seat within the grooves 1970a. The support surface 1918a locks on the support surface 1921a when there is a compressive or downward force (hollow arrow) on the upper locking member 1917a locking the implant 1910a. Upward force or extension (solid arrow) of the upper locking member 1917a causes the lower locking member 1920a to ride on the disengaging surface 1919a and out of the groove 1970a allowing the upper locking member 1917a to rise with the expansion of the implant 1910a.

Figure 32A:
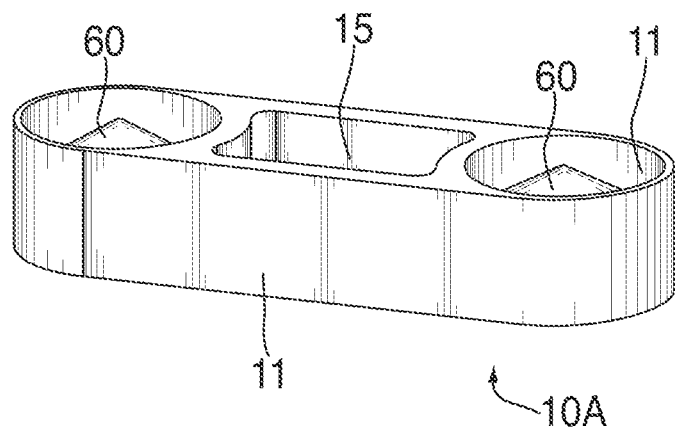
FIGS. 32A and 32B are perspective views of a further alternative embodiment of the present invention including locking, conical bone engaging anchors.
Figure 32B:
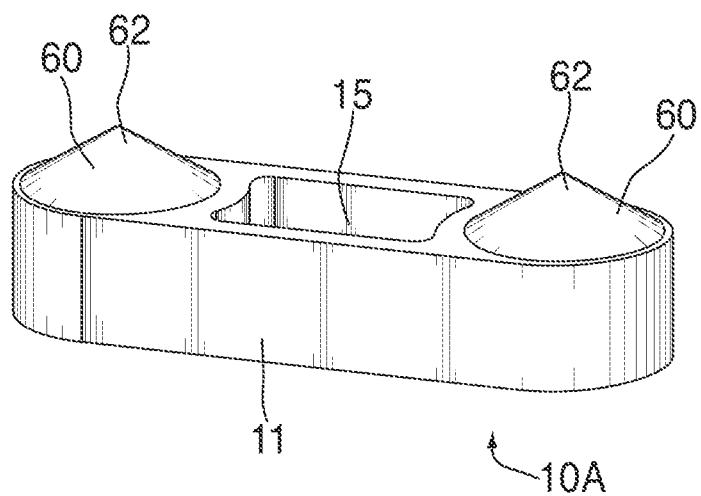

In a further aspect of the present invention, a piston/cylinder and locking arrangement as described above may be used to deploy extendable bone anchors. For example, implant 10A with conical bone engaging anchors 60 as shown in FIGS. 32A and 32B may be constructed with pistons 22 and cylinders 16 as described above in connection with implant 10 and shown, for example, in FIGS. 2, 3 and 4B. Implant 10A has a housing 11 as previously described and may include other previously described features such as interior cavity 15 for bone growth stimulating substances. However, in this embodiment, instead of upper interlocking end plate 13, the two pistons 22 individually terminate with conical bone engaging anchors 60. The bone engaging anchors, including sharp leading tip 62, form surface for engaging the vertebral body.

As shown in FIG. 32A, bone engaging anchors 60 are in a contracted configuration, within housing 11, to facilitate insertion of implant 10A. Using hydraulic actuation as previously described, bone engaging anchors 60 are moved to an extended configuration as shown in FIG. 32B, wherein at least leading tip 62 extends beyond housing 11 to engage and anchor in the bone. In order to ensure that the bone engaging anchors remain firmly engaged in the bone, locking mechanisms including multi-stepped upper and lower lock supports 17, 20 as previously described in connection with implant 10 and shown, e.g. in FIGS. 6A-12C, are provided to support each anchor 60 in the extended configuration. With this arrangement, the extended and locked anchor 60 helps to retain the implant in place.

Figure 33A:
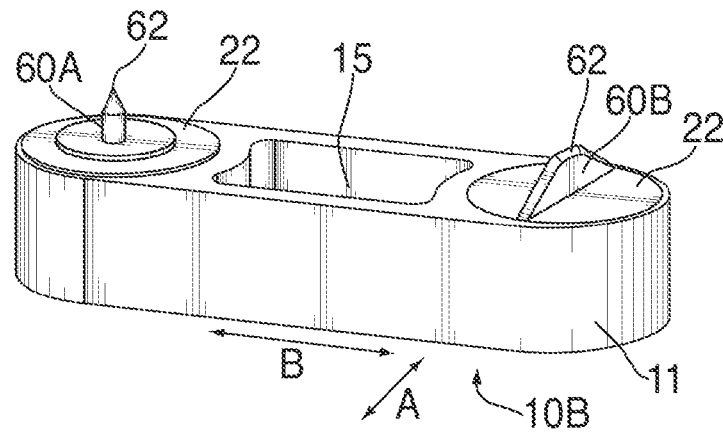
FIGS. 33A-C are perspective views showing alternative bone engaging anchors.
Figure 33B:
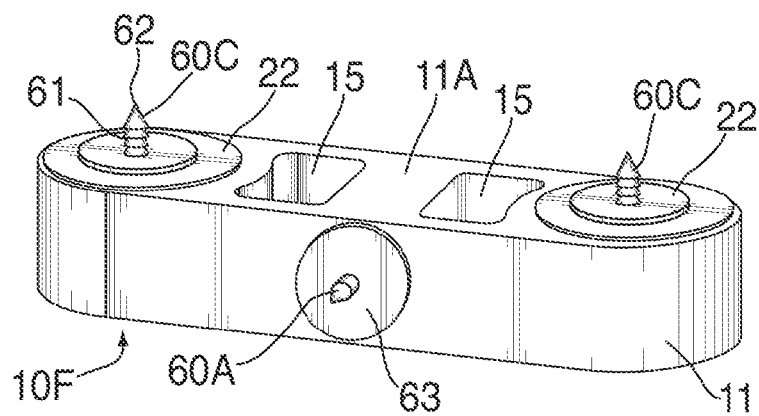
Figure 33C:
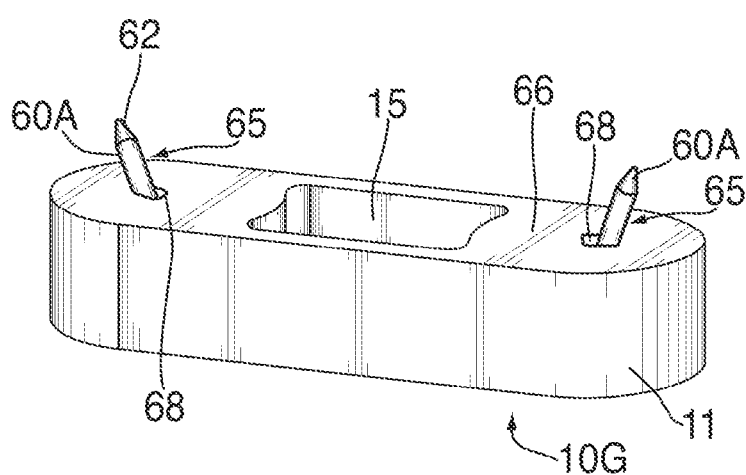

A variety of alternatives are possible for the bone engaging anchor according to the invention as illustrated in FIGS. 33A-C. For example, implant 10B in FIG. 33A includes bone engaging anchors formed as spike 60A and blade 60B. Blade 60B can be particularly effective in preventing motion along the insertion path after deployment. In this case, the length of the blade 60B is aligned in the direction shown by arrow A. This is substantially orthogonal to the direction of implantation (arrow B) and would resist movement in that direction. Implant 10F, shown in FIG. 33B includes further possible variations. In this embodiment, the bone engaging anchors are formed as barbed spikes 60C. Barbs 61 along the shaft of the spikes resist forces that tend to move the tissue away from the implant along the axis of the anchor (much as the screw threaded anchor described below would also resist this force). Also included in implant 10F is a lateral bone engaging anchor 63 for anchoring in laterally oriented tissue. In the illustrated embodiment, lateral anchor 63 includes a plain spike 60A. Lateral anchor 63 is formed in the same manner and with the same components, i.e. piston, cylinder, locking mechanism, etc. as elsewhere described in this application, except that the components are oriented laterally as shown. To provide support for the bone anchor components in this lateral embodiment, housing 11 includes a central member 11A that divides interior cavity 15 into two portions. In the configurations of implants 10B and 10F, the top of piston 22 can also become a bone engaging surface when the anchor member is fully received within the bone. FIG. 33C shows a further alternative implant 10G, including anchors 65 extending obliquely from housing 11, rather than orthogonally. This oblique arrangement is helpful in resisting side to side rotational forces (for example when the patient/spine bends towards the side) and expansion forces. Once again, obliquely extending anchors 65 are essentially identical to other bone engaging anchors described herein except for the oblique orientation. Here, holes 68 are provided in top end plate 66 for the spikes to pass through. In general, bone engaging anchors according to embodiments of the invention should have a relatively small termination (e.g. tip 62) relative to the size of the piston diameter so that the force on the piston created by the hydraulic fluid is proportionally a much greater force at the small anchor termination to enhance its ability to extend into hard bony tissues. It will also be appreciated by persons skilled in the art that the various features of the bone engaging elements, e.g. spike, blade, barbs, etc., described herein may be combined in any desired combination, in addition to the exemplary combinations shown in the figures of the present application.

Figure 34A:
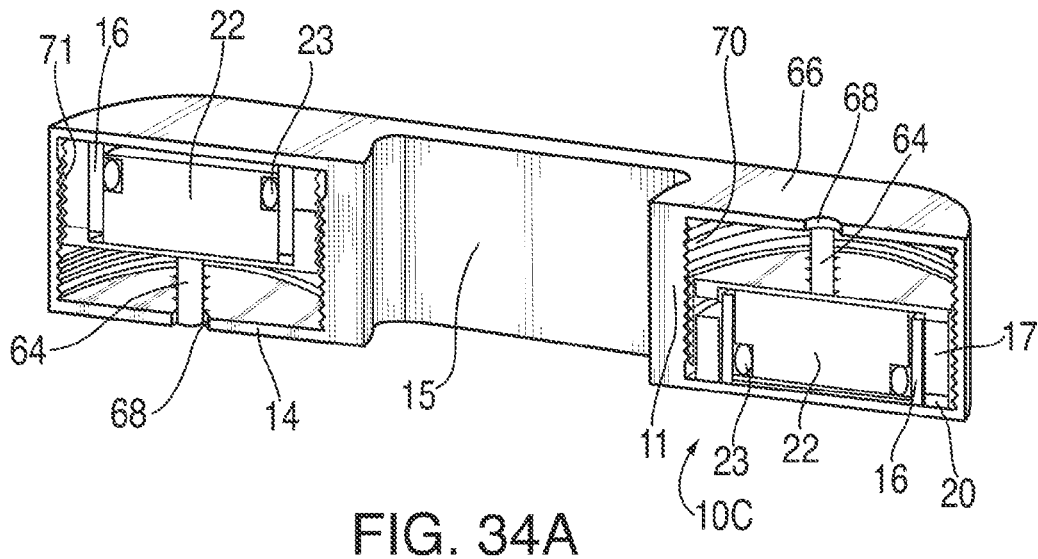
FIGS. 34A and 34B are perspective cross-sectional views of another alternative embodiment of the present invention including locking, screw-threaded bone engaging anchors.
Figure 34B:
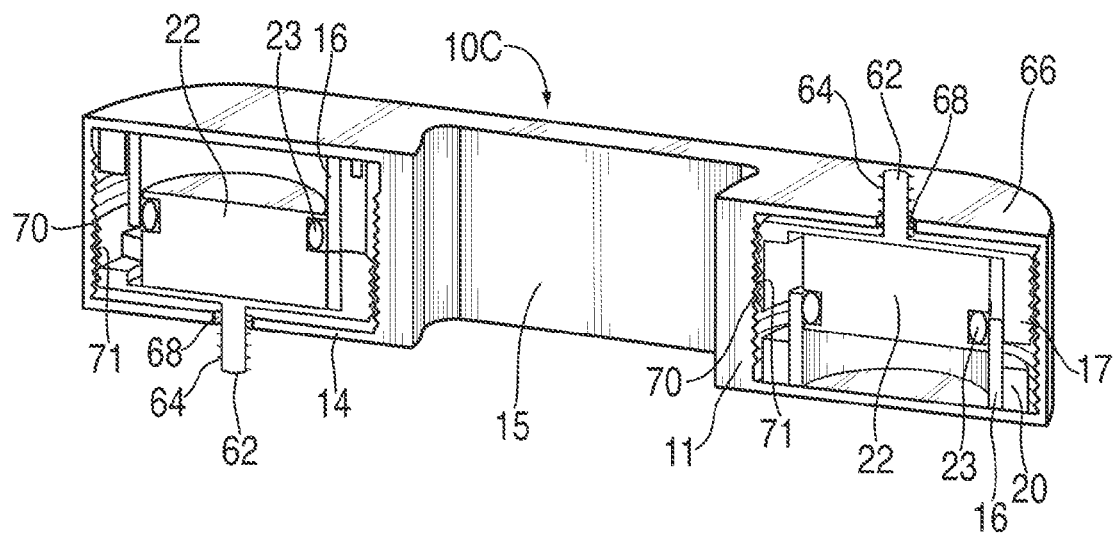

In another alternative embodiment, illustrated in FIGS. 34A and 34B, implant 10C includes screw-threaded members 64 as bone engaging anchors. Implant 10C also illustrates a further alternative wherein the bone engaging surfaces, such as the anchors, extend from opposite sides of the implant. In this exemplary embodiment, interlocking end plate 13 is replaced with an integrated top end plate 66. Holes 68 are provided for threaded member 64 to pass through. Persons of ordinary skill in the art will appreciate that holes 68 will be located as needed; in the illustrated embodiment one is in top end plate 66 and the other in bottom end plate 14.

Threaded members 64, as bone engaging anchors extend outwardly from pistons 22. In order to rotate the threaded anchors into the bone when the pistons are extended, the inner wall of housing 11 is provided with a screw-threaded surface 70 that mates with corresponding threads 71 cooperating with pistons 22. As previously described, seals 23 act between the pistons 22 and cylinders 16 to prevent leakage of hydraulic fluid. When fluid is pressurized within the cylinders as described for prior embodiments, the piston is extended, but also driven in a circular motion by the engagement between threaded surfaces 70 and 71. The screw-threaded member 64 is thus driven into adjacent bone as it is extended to anchor the implant.

Once again, locking mechanisms as previously described and shown, for example, in FIGS. 6A-12C, may be employed to prevent the bone engaging anchors from becoming unengaged from the bone. In the cross-sectional views of FIGS. 34A and 34B, upper and lower lock supports 17, 20 are visible around the outside of the piston and cylinders. Alternatively, depending on the depth and pitch of the threaded portions, use of a separate locking mechanism may not be required. As persons of ordinary skill will appreciate, the configuration of the threads alone may be sufficient to prevent the anchors from backing out.

Figure 35A:
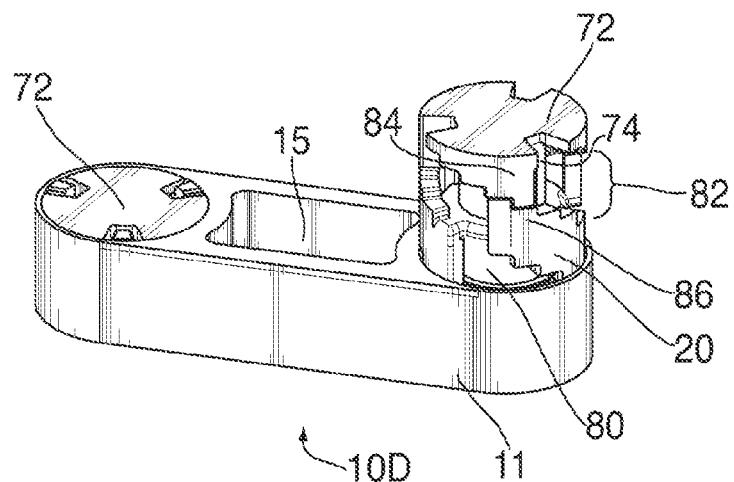
FIGS. 35A and 35B are perspective views of yet another embodiment of the present invention including locking, telescoping bone engaging surfaces.
Figure 35B:
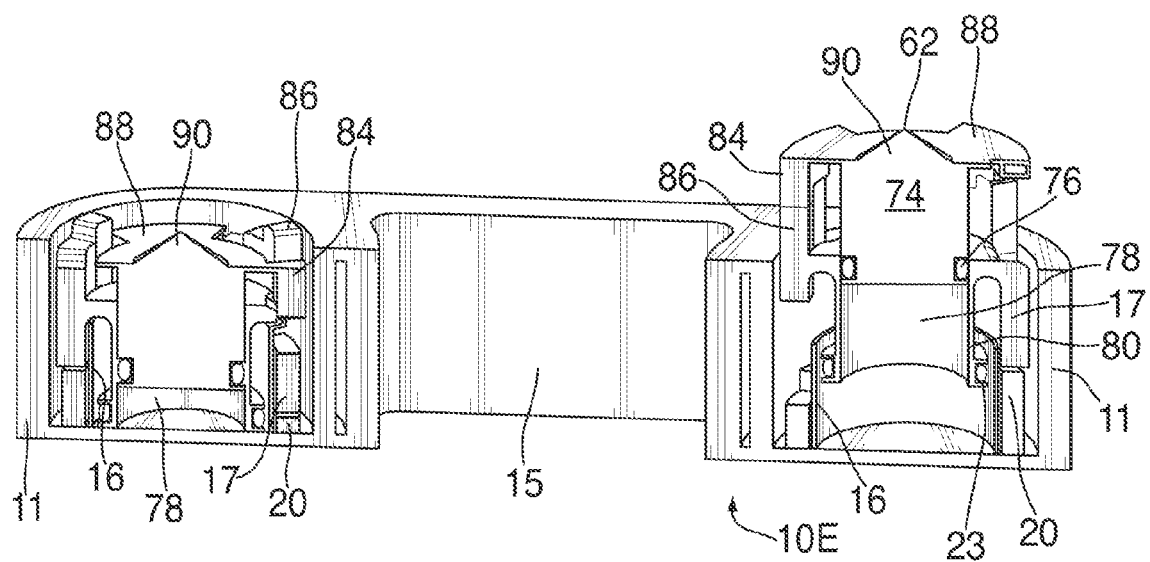

FIGS. 35A and 35B illustrate a further aspect of the present invention wherein locking mechanisms as described are utilized to secure telescoping bone engaging surfaces in place. As used herein, telescoping refers to nested, extendable members including at least one intermediate member between a base and bone engaging member.

Referring first to FIG. 35A, implant 10D has substantially planar bone engaging members 72. Bone engaging members 72 are thus similar to the bone engaging members of implant 10, but instead individually actuated without interlocking end plate 13. The piston/cylinder arrangement is also similar to that previously described except that here upper piston 74 is received in intermediate piston 80. Intermediate piston is in turn received in cylinder 16 as was previously described for piston 22. Upper piston 74 is sealed against intermediate cylinder 78 of intermediate piston by upper piston seals 76 (see FIG. 35B).

The telescoping bone engaging members 72 are secured by locking mechanisms in a similar manner to the earlier described embodiments, with the addition of an upper lock support 82 for the upper piston. Intermediate piston 80 is supported by upper lock support 17 and lower lock support 20 as previously described. Upper lock support 82 includes upper and lower lock supports 84, 86. Thus, upper piston 74 is secured to upper lock support 84 of the upper lock set. Lower lock support 86 of the upper lock set is mounted on top of upper lock support 20 of the lower lock set. One difference from the earlier described embodiments is that separate spring actuators 26 are not required for the upper lock set as they may be rotated along with the lower lock set by actuators 26.

Implant 10E, as shown in FIG. 35B includes a further variation in which the planar portion of upper bone engaging surface 88 is effectively annular with a conical anchor 90 at the center. Advantages of embodiments of the present invention including bone engaging anchors include the ability of the anchors to be extended lateral from the long axis of the implant (i.e., the insertion axis) with a relatively high force using the relatively small connection to the implant of the hydraulic line. This is an advantage over other methods that require larger access or larger connections to the implant for lager tools or non-hydraulic extension forces to extend the anchors into the hard, bony tissue.

Figure 36A:
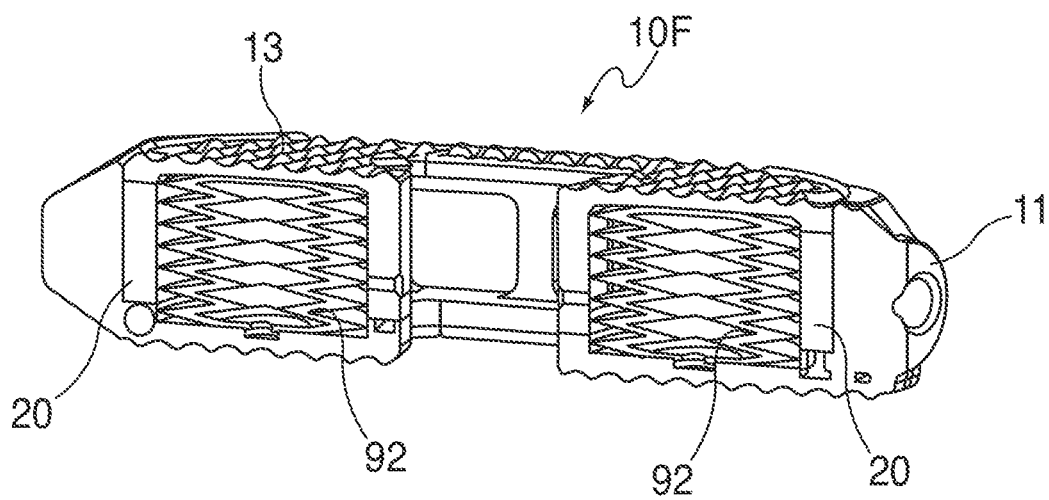
FIGS. 36A and 36B are cross-sectional views of another exemplary embodiment of the present invention shown in a collapsed and an expanded configuration respectively.
Figure 36B:
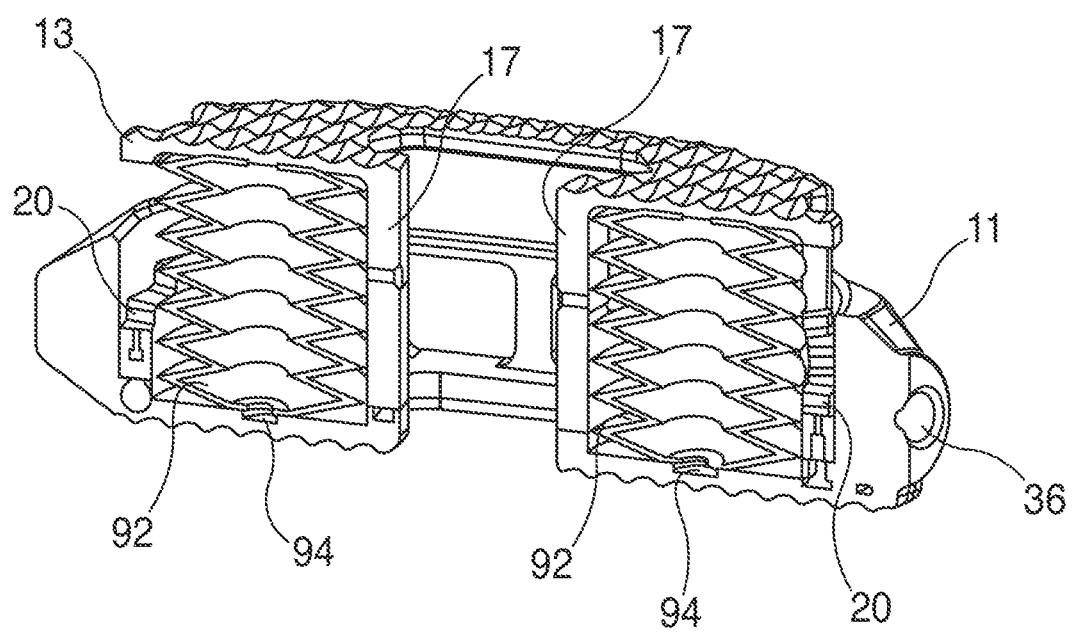
Figure 36C:
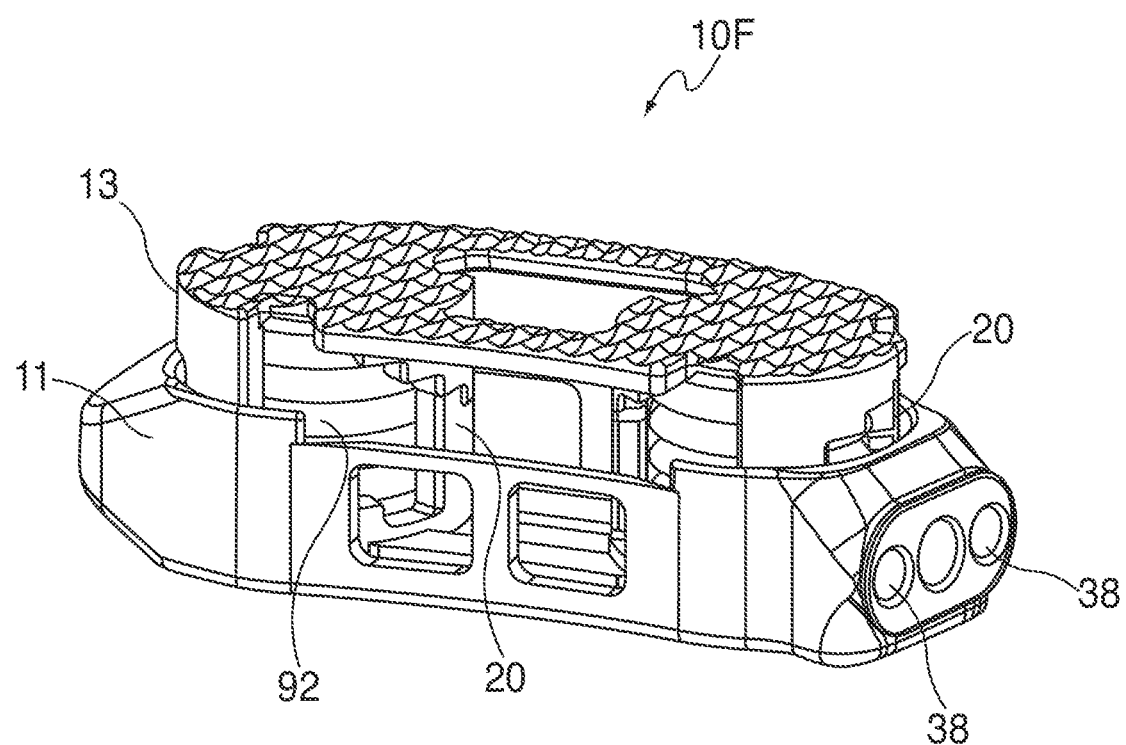
FIG. 36C is a posterior perspective view of the embodiment in FIG. 36B, shown in an expanded state.

Although the previously described embodiments of the invention included cylinders 16 and pistons 22 expanded with a pressurized fluid as the mechanism used to lift the top end plate away from the bottom end plate, embodiments of the present invention are not limited to only such lift mechanisms. In FIGS. 36A-C an alternative embodiment of the present invention comprising implant 10F is shown wherein a pair of bellows 92 replaces the piston and cylinder pairs previously described. One end of bellows 92 is attached to housing 11 and the other end to top end plate 13. A pressurized fluid added via pressure input ports 38 is directed through bellows orifice 94 into the inside of bellows causing the bellows to expand. The expanding bellows forces top end plate 13 away from housing 11 and lower lock supports 20 are rotated to lock the device in the expanded configuration as was previously described. Bellows 92 can be made of any biocompatible material such as the 316 series of stainless steels, titanium or a titanium alloy, a cobalt chromium alloy, or an implantable polymeric material. The bellows can be of an accordion-like folding configuration as shown in FIGS. 36A-C or any other regular or irregular configuration which can fit inside of the housing and lock supports in the collapsed configuration and expand sufficiently when pressurized to lift top end plate 13 the desired amount away from housing 11. Lower lock supports 20 and upper lock supports 17 provide a confining geometry for bellows 92, which allows use of an irregular bellows configuration. With a bellows arrangement as shown in FIGS. 36A and 36B, the amount of lift is not limited as is the case in a cylinder and piston to the amount that the collapsed cylinder and piston overlap.

Figure 37A:
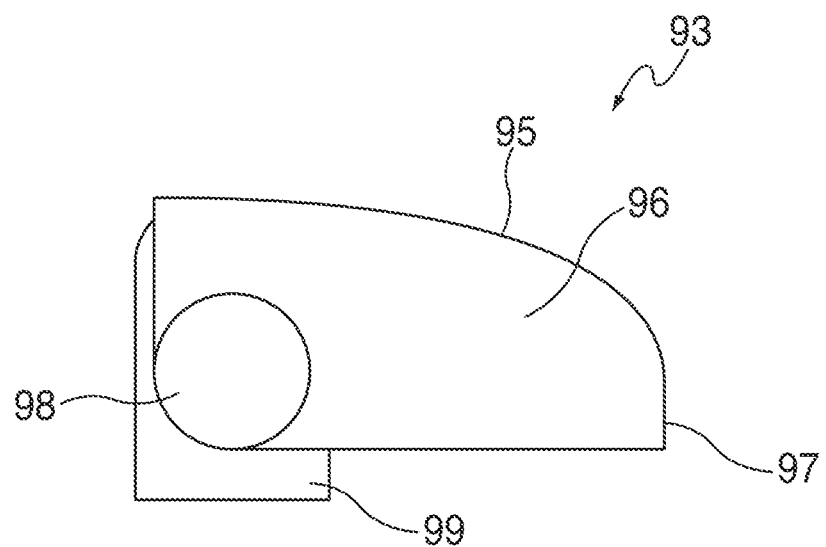
FIGS. 37A and 37B are end views of a lift mechanism according to a further exemplary embodiment of the present invention, shown in a collapsed and an expanded configuration respectively.
Figure 37B:
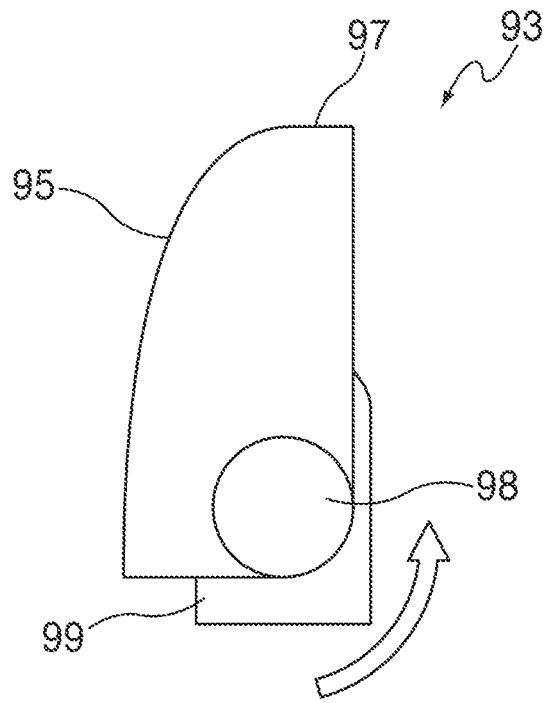
Figure 38A:
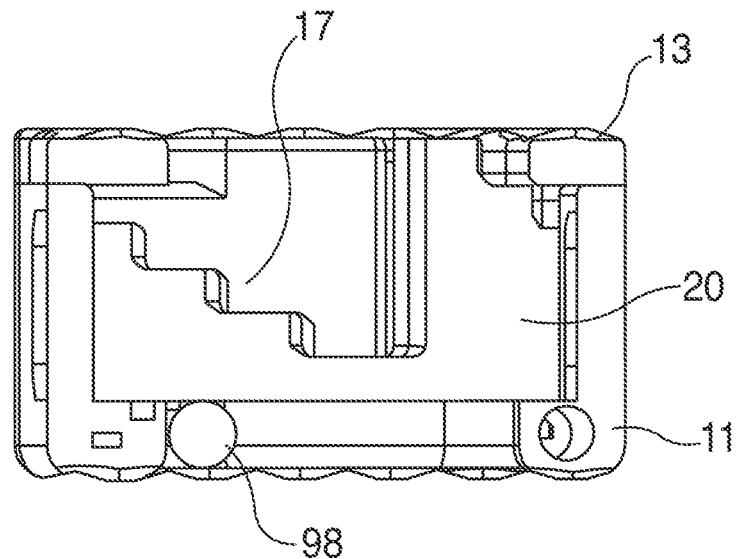
FIGS. 38A and 38B are end views of a cross section of another embodiment of the present invention utilizing the lift mechanism shown in FIGS. 37A and 37B, shown in a collapsed and an expanded configuration, respectively.
Figure 38B:
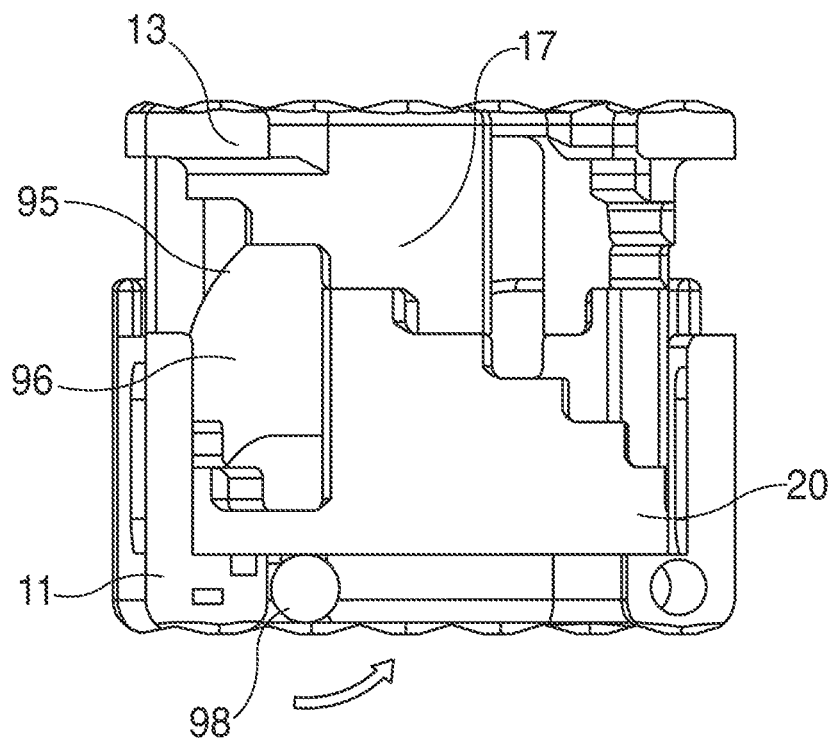
Figure 39A:
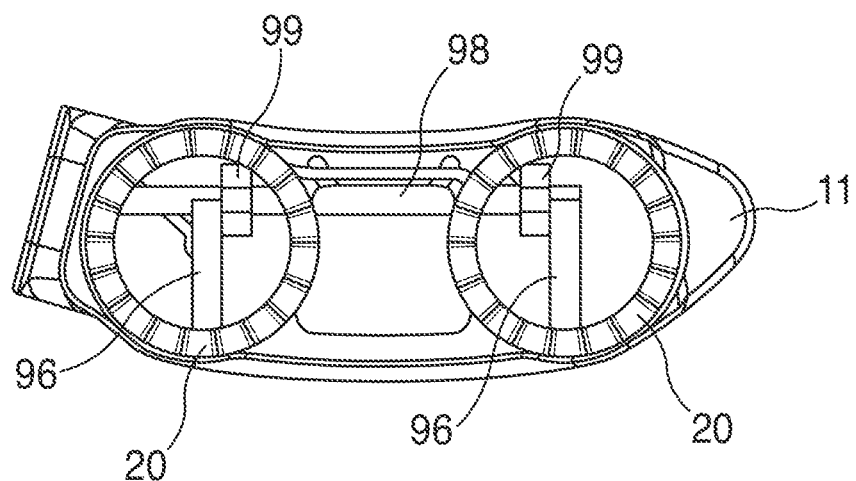
FIGS. 39A and 39B are top views of the respective embodiments shown in FIGS. 38A and 38B with the top plate removed.
Figure 39B:
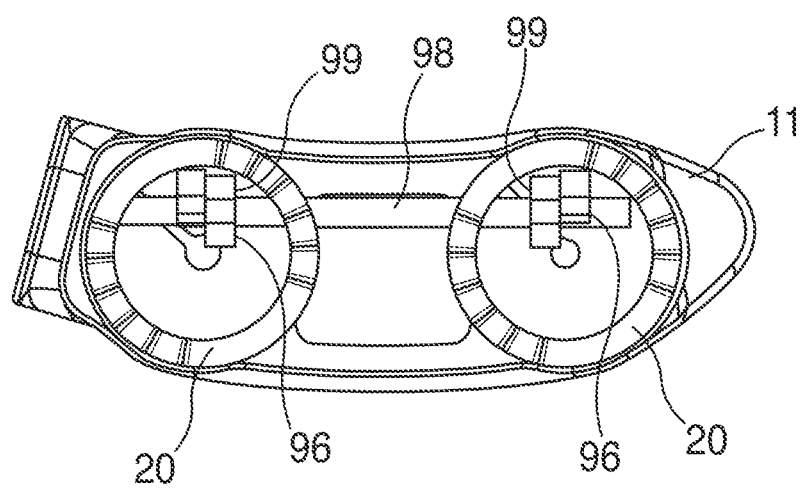
Figure 40:
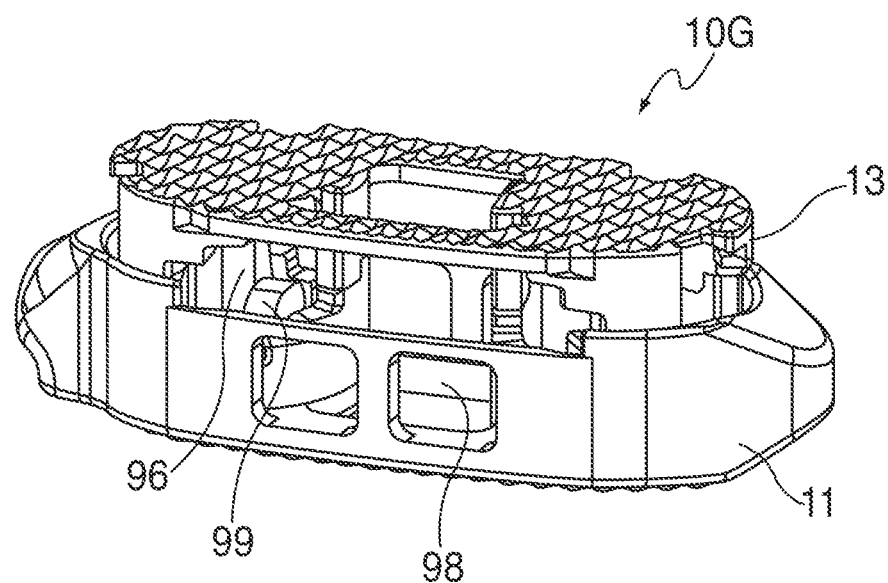
FIG. 40 is an anterior perspective view of the embodiment shown in FIG. 38B.

Other exemplary embodiments do not rely on the use of a pressurized fluid for expansion. For example, FIGS. 37A and 37B show an alternative rotating cam lift mechanism 93. Cam lift mechanism 93 includes cam 96 with a substantially curved cam surface 95 and a substantially flat top surface 97, rotating shaft 98, and shaft supports 99. Cam 96 is attached to rotating shaft 98, and shaft 98 is supported by and rotates within shaft supports 99. In an implant 10G (FIG. 40) using this mechanism, the shaft supports 99 are anchored to the inside of housing 11 and rotation of shaft 98 (depicted by curved arrows) rotates the curved cam surface 95 against the bottom of top end plate 13 and moves top end plate 13 away from housing 11 as shown in FIGS. 38A-38B, 39A-39B and 40. The shape of cam 96 determines both the amount of lift that is possible and the relative amount of lift to the amount of rotation of the cam. The cam is not limited by 90 degrees of rotation depicted in the figures. Any shape of a cam that is rotated by any amount from as little as 10 degrees to as much as 355 degrees is possible without departing from the scope of the present invention. Shaft rotation can be accomplished by several means as will be discussed in more detail below. Use of cam lift mechanism 93 as the lifting mechanism along with lower and upper locking supports 20 and 17 for implant 10G allows the lift mechanism to support only the initial lifting loads and not have to support the repetitive long-term supporting loads on implant 10G which are borne by the locking supports. Cam 96 does not require a substantially flat top surface 97 as shown in the exemplary embodiment to support top end plate 13, but such a surface provides a rotational endpoint for the surgeon rotating shaft 98.

Figure 41:
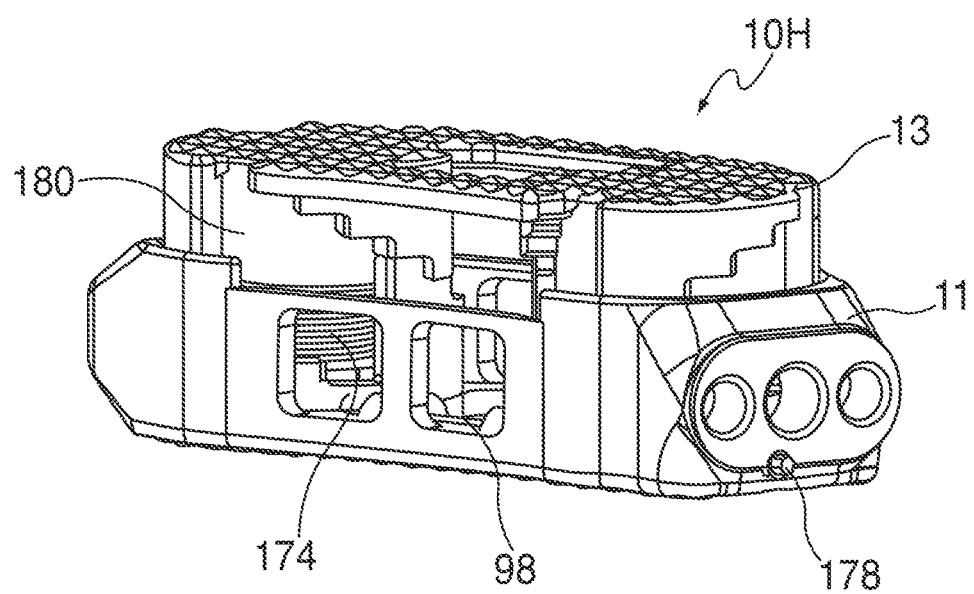
FIG. 41 is a posterior perspective view of still another exemplary embodiment of the present invention, shown in an expanded configuration.
Figure 42:
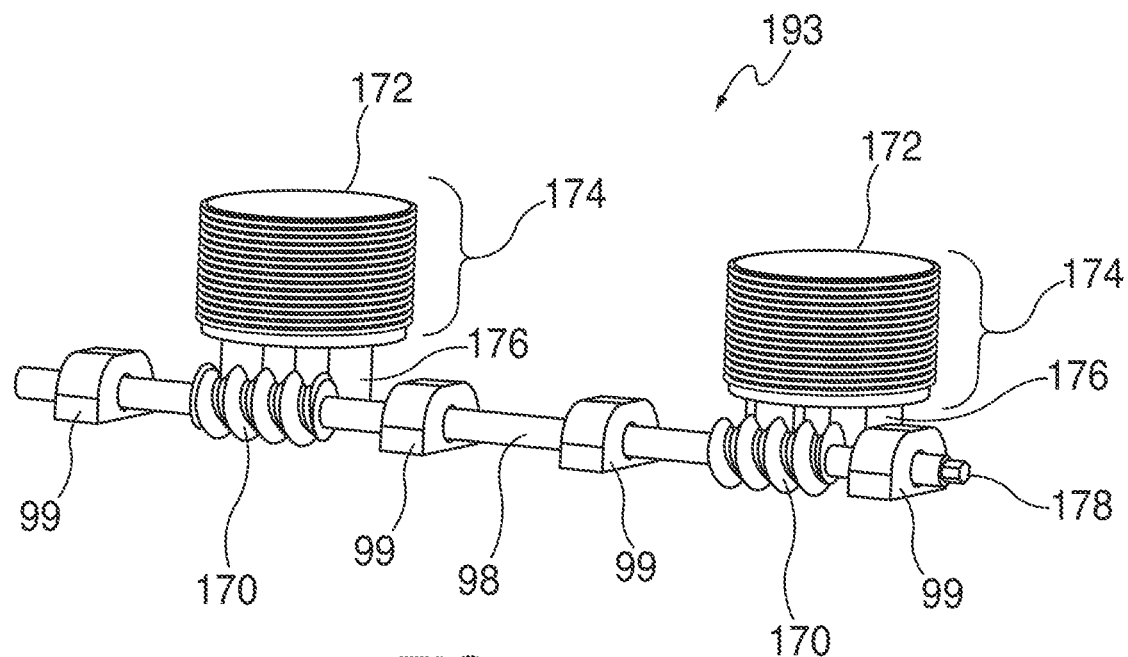
FIG. 42 is a perspective view of a lift mechanism of the embodiment of FIG. 41.
Figure 43A:
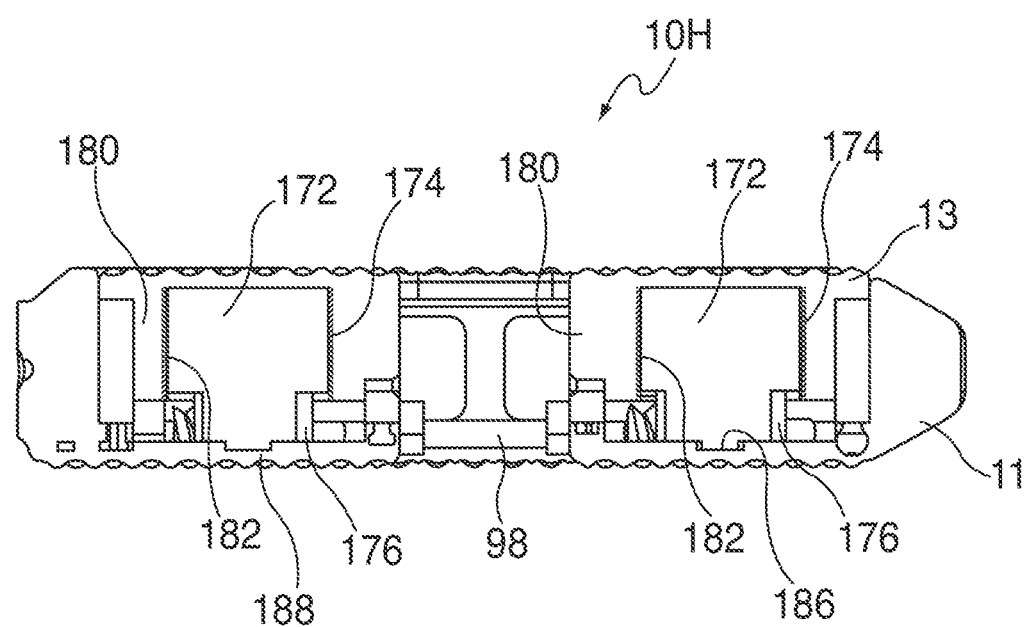
FIGS. 43A and 43B are cross-sectional views of the embodiment of FIG. 41 shown in a collapsed and an expanded configuration, respectively.
Figure 43B:
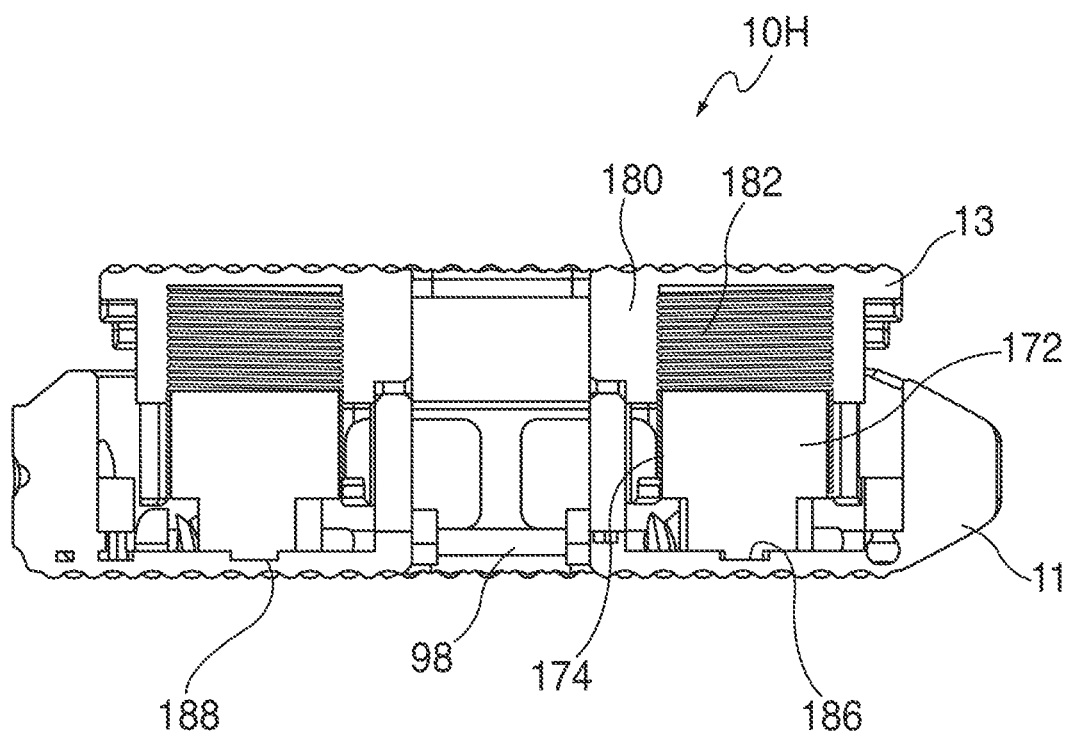

Another alternative embodiment is implant 10H shown in FIGS. 41, 43A and 43B. Implant 10H uses a rotating screw lift mechanism 193 as shown in FIG. 42. This mechanism includes shaft 98, shaft supports 99, worm gears 170 attached to shaft 98 and a shaft input end 178 at one end of shaft 98. The mechanism also includes lift screws 172, which have lower lift threads 174 and transfer gear 176 and supporting boss 186. Applying a torque via shaft input end 178 turns shaft 98, which turns the attached worm gears 170. Worm gears 170 turn transfer gear 176 on lift screw 172. Lift screw 172 is contained within housing 11 by way of its supporting boss 186, which is seated in housing bearing 188. Rotation of lift screw 172 transfers force from lower lift threads 174 to upper lift threads 182 on upper lift nut 180. Upper lift nut 180 is attached to top end plate 13 so that rotation of shaft input end 178 lifts upper end plate 13 away from housing 11. The relative pitch of worm gears 170 and matching transfer gears 176 and the lower lift threads 174 and matching upper lift threads 182 can be varied to achieve the desired amount of lift relative to the amount of rotation and torque. The torque can be applied by any means well known by those skilled in the art including but not limited to electric motor, pneumatic or hydraulic turbine, or manual rotation of an actuator. Shaft input end 178 is shown as a hexagonal post, but any alternative input end can be used without departing from the scope of the present invention, such as, but not limited to, a square or star-shaped post, a square, star or hexagonal-shaped socket, or a keyed shaft.

Figure 44:
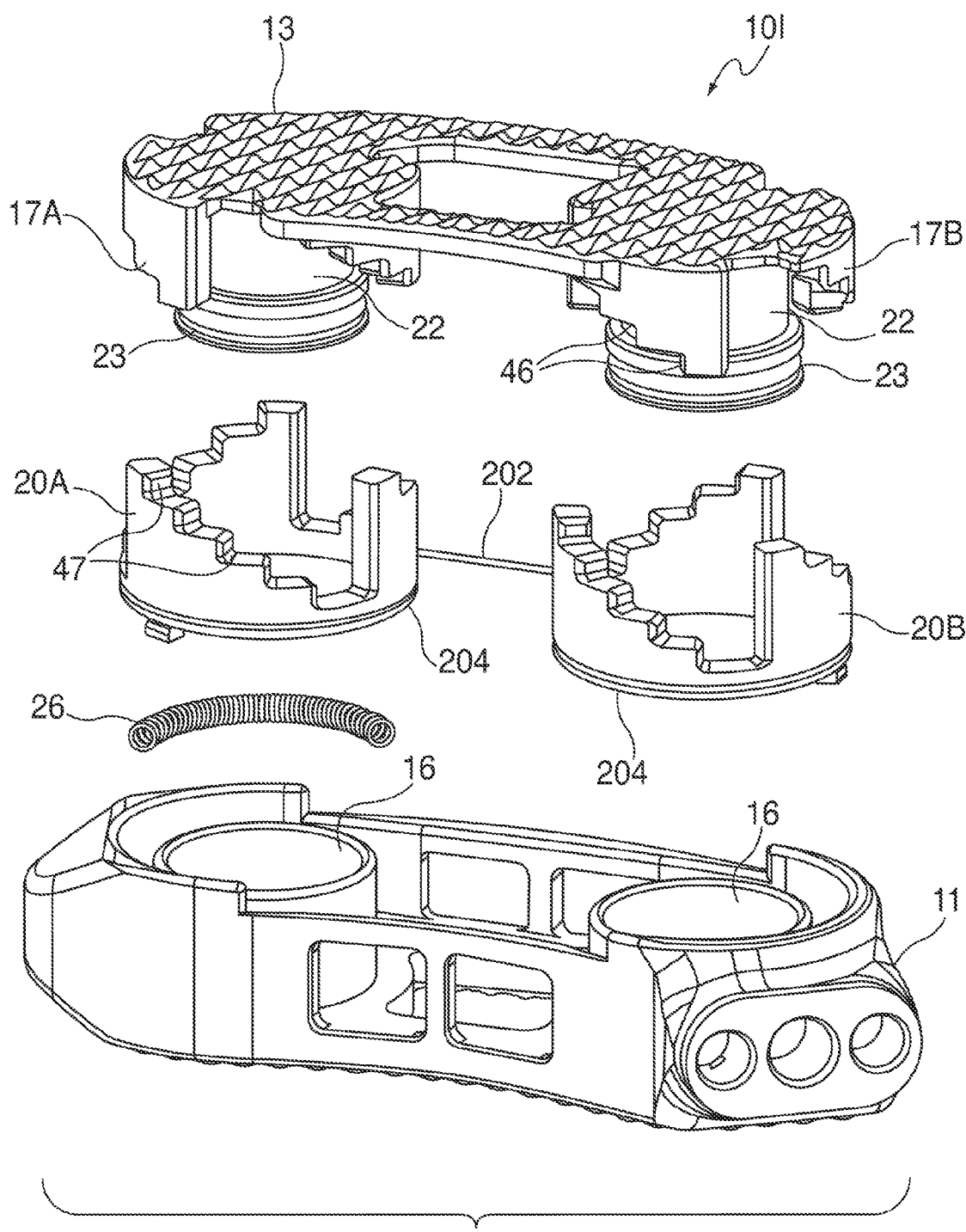
FIG. 44 is an exploded perspective view of another embodiment of the current invention.

As shown in FIG. 44, an alternative embodiment of the implant 10I includes a linking element 202 that connects the lower lock supports 20A and 20B. The linking element 202 coordinates the action of the lower lock supports 20A and 20B. When the locking actuator 26 actuates the leading lower lock support 20A, the linking element 202 in turn actuates the following lower lock support 20B. In this embodiment the implant 10I may require only a single locking actuator 26, however plural locking actuators as described above (see, for example, FIG. 3) may be employed for greater actuation force as needed. In addition to actuating the following lower lock support 20B, the linking element 202 prevents the leading lower lock support 20A from actuating until the alignment faces 46 of both the leading upper lock supports 17A and the following upper lock supports 17B each clear the alignment faces 47 of both the leading lower lock support 20A and the following lock support 20B. In this manner the linking element 202 ensures the coordinated actuation of the lower lock supports 20A and 20B to ensure that the implant 10I will always lock at the same height on both sides. This can be advantageous for certain implants placed in the spine where an even expansion of the implant is desired.

Linking plural lower lock supports, such as supports 20A and 20B, with a linking element 202 for even expansion in the manner described may be advantageous over an implant with a similarly sized single lock support 20, and single cylinder 16 and piston 22 due to the increase in the number of support elements, the broader support base, and the increase in expansion force due to the increased number of cylinder and piston pairs. Increasing the size of a single lock support would still have disadvantages of a larger width that would limit the ability for implantation in minimally invasive surgery. Embodiments of the invention are not limited to just the pair of lower locking supports 20A and 20 B as shown in, for example, FIG. 33. Rather, any number of sets of cylinders 16, pistons 22, upper lock supports 17, and lower lock supports 20, with a locking actuator 26 and the appropriate number of linking elements 202 are possible.

Figure 45A:
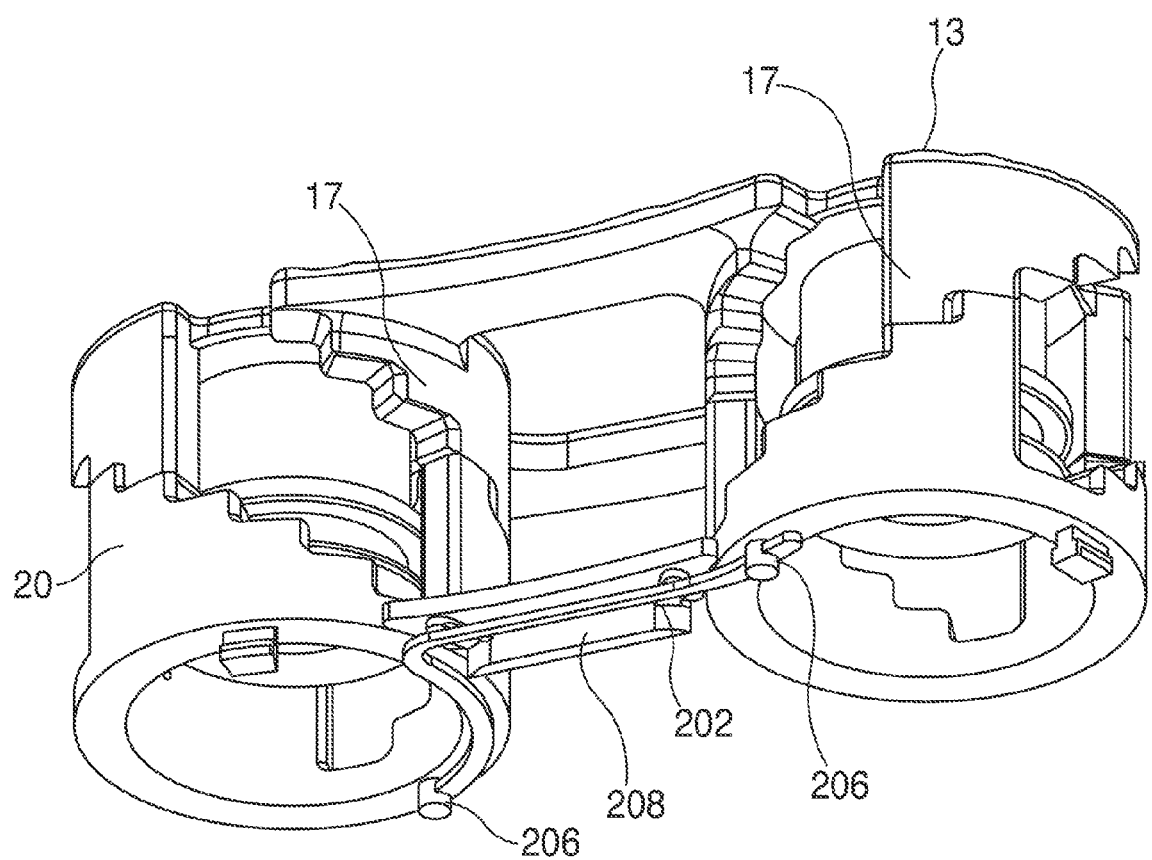
FIG. 45A is a partial inferior perspective of another embodiment of the present invention.
Figure 45B:
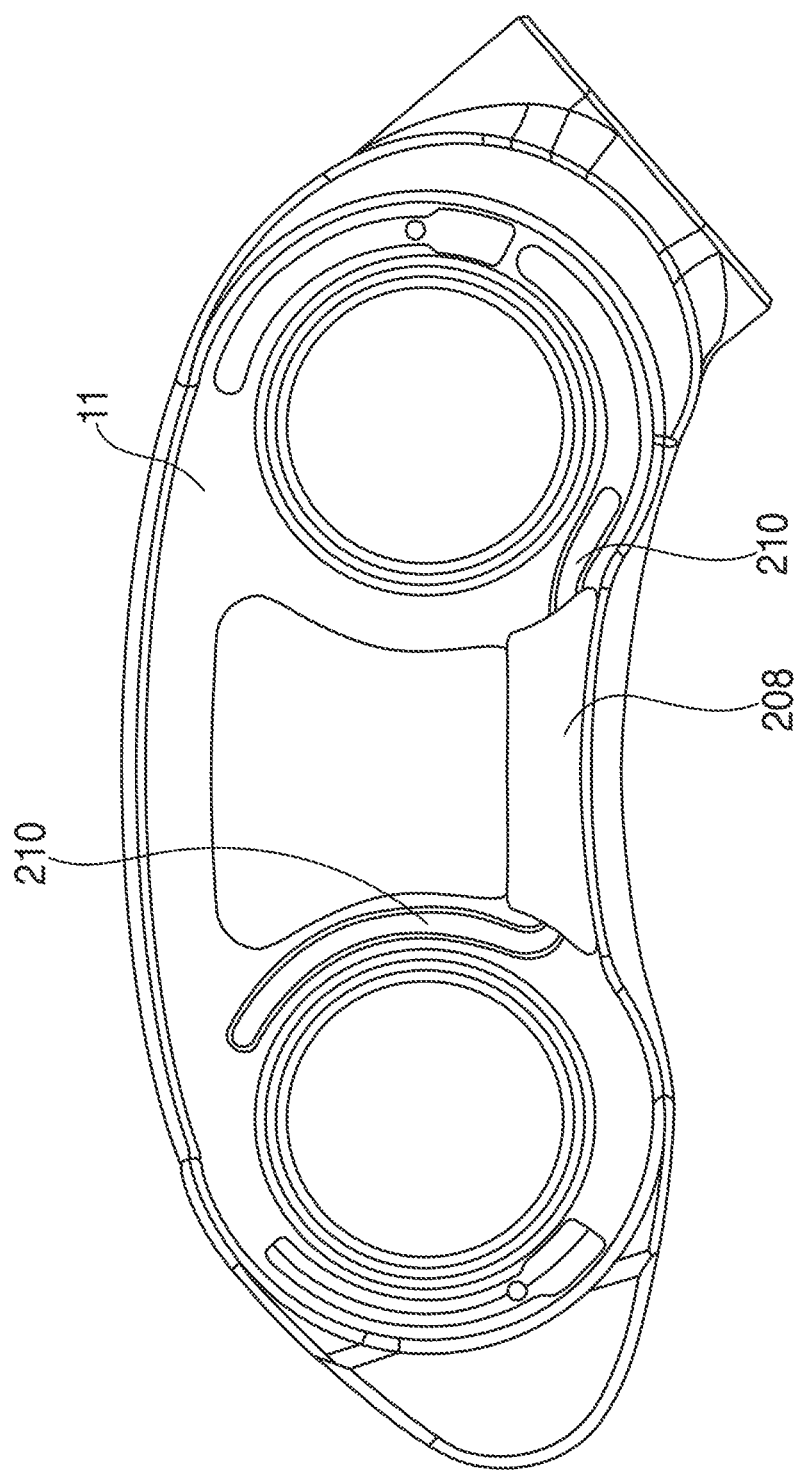
FIG. 45B is a partial top view of the embodiment shown in FIG. 45A.

For the embodiment illustrated in FIG. 44, linking element 202 is configured to fit inside attachment grooves 204 on the lower lock support 20A, B. Alternatively, linking element 202 may be configured to rest on the outside diameter of the lower lock support 20A, B. The linking element 202 can also be configured to run underneath the lower lock supports 20A, B as shown in FIGS. 45A-D. For implant 10I in FIG. 44 both of the lower lock supports 20A and 20B rotate in the same direction when actuated. Elements of an alternative implant shown in FIGS. 45A-B include lower lock supports 20 that actuate with rotation in opposite directions. The linking element 202 is guided between the lower lock supports 20 through a link channel 210 in housing 11 (FIG. 45B). The linking element 202 is constrained in the link channel 210 by a channel cover 208. The linking element 202 is connected to the lower lock supports 20 by means of link pins 206.

The linking element can be made from any of a variety of implantable materials including: a titanium wire, a titanium cable, a stainless steel wire or cable, a nitinol wire, a braided or mono-filament suture from any manner of suture material such as silk, polyester, polypropolyene, ePTFE, or UHWPE. An implantable material that has a tensile strength sufficient to transfer the actuation force from the leading lower lock support 20A to the following lower lock support 20B as well as flexibility sufficient to follow the link channel 210 and/or rotate around the lock supports 20 may be used. Linking element 202 can be attached to the lower lock supports 20 in a number of ways known to those practiced in the art, the selection of which depends on factors such as the linking element material and the lower lock support material. Suitable techniques include laser welding, resistance welding, adhesive bonding, crimping, attaching with clamps, pins, or screws, or being threaded through an opening and securing with a knot.

Figure 46A:
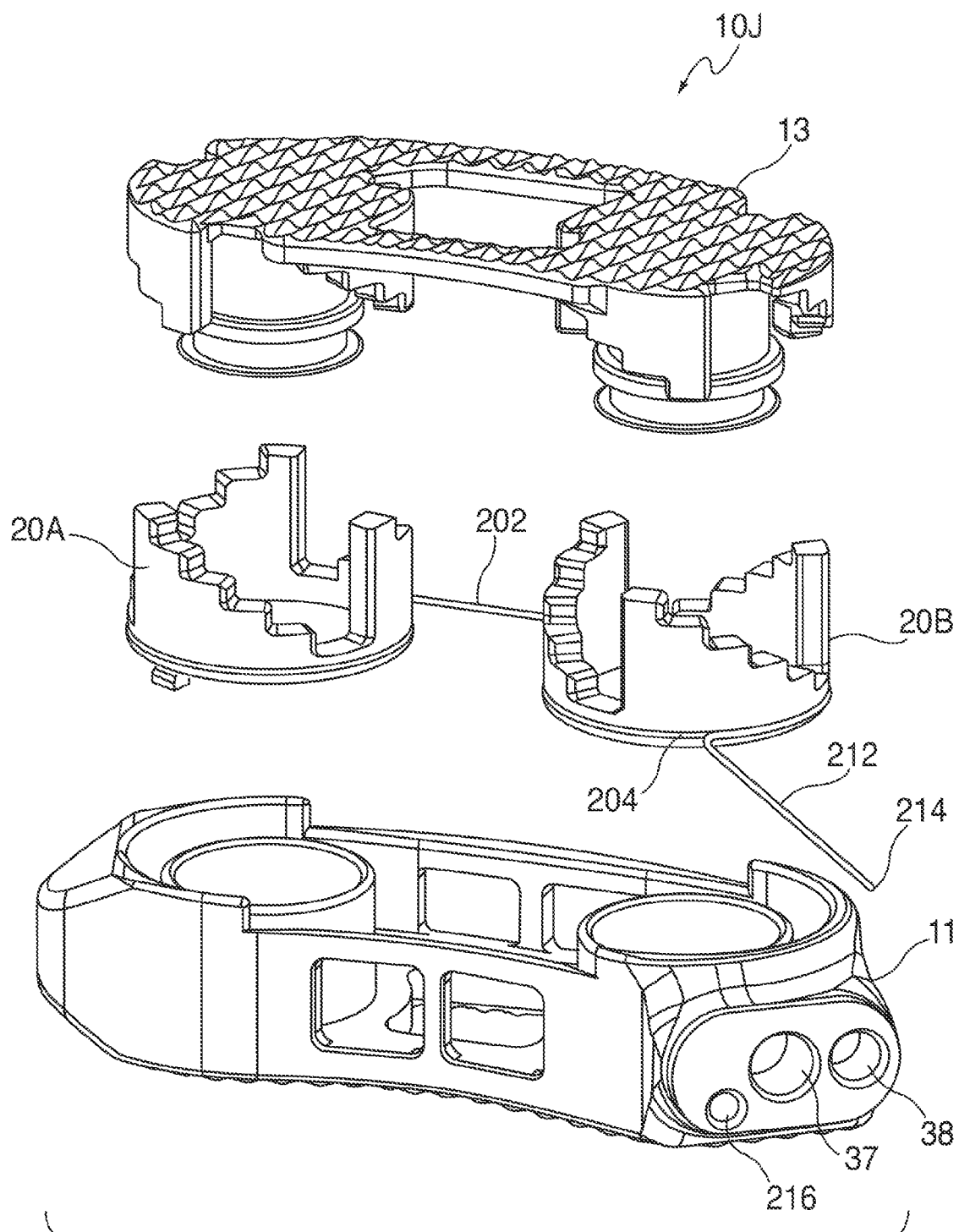
FIG. 46A is an exploded perspective view of another embodiment of the current invention.
Figure 46B:
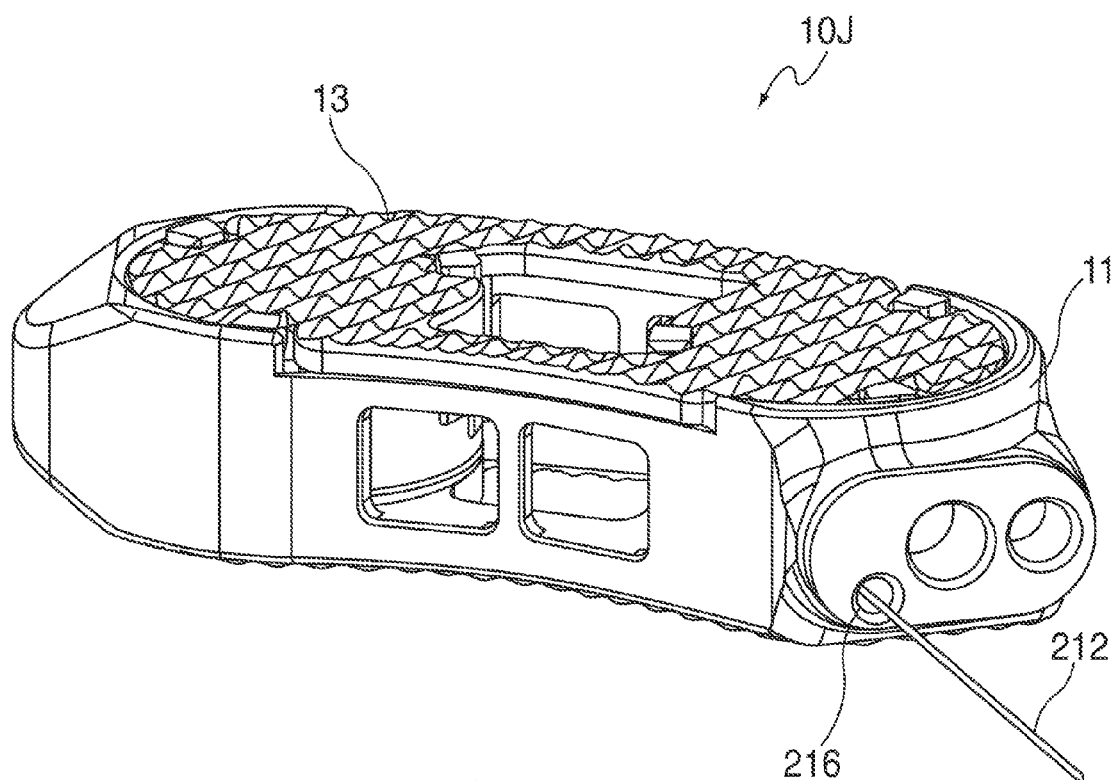
FIGS. 46B and 46C are superior perspective views of the embodiment shown in FIG. 46A in the collapsed and expanded configurations respectively.
Figure 46C:
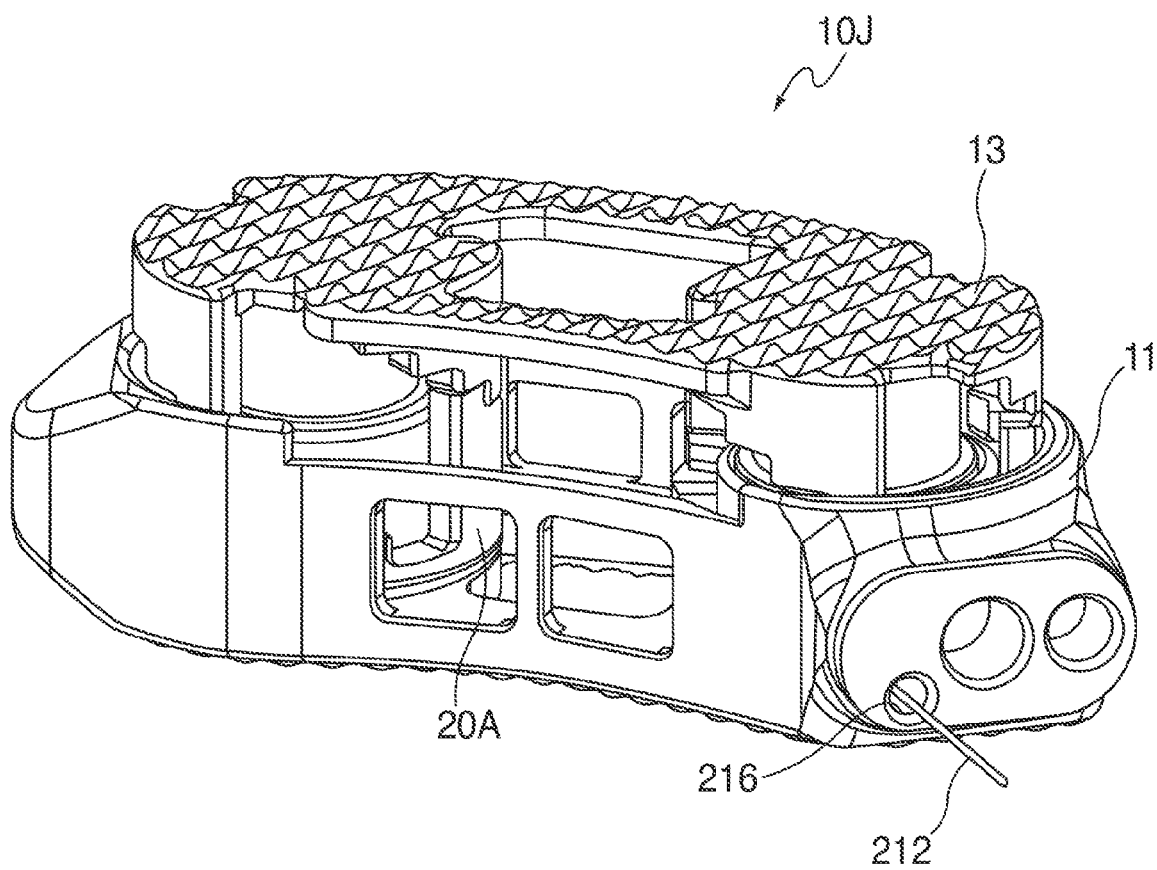

Turning now to FIGS. 46A, B and C an implant 10J with an additional feature, an unlocking tether 212 is shown. Unlocking tether 212 is attached to the following lower lock support 20B in attachment groove 204. Unlocking tether 212 is attached in the opposite direction as the linking element 202 and can be attached in any of the ways described above for attaching the link element 202. The proximal end 214 of the unlocking tether 212 exits the housing 11 of the implant 10J through the unlock port 216. The proximal end 214 can be actuated by an external force or mechanism (not shown). Actuation of the proximal end 214 of the unlocking tether 212 to translate it away from the implant 10J causes rotation of the following lower lock support 20B, which will tension and translate the linking element 202 which will rotate the leading lower lock support 20A. In this manner the unlocking tether 212 can be used to unlock the implant 10J so that it can collapse to a lower or to its original height. In FIG. 46B the implant 10J is collapsed and the unlocking tether 212 is extended a maximum distance out of the unlock port 216. FIG. 46C shows the same implant 10J with the top plate 13 fully expanded above the housing 11 and locked. The unlocking tether 212 has shortened as it was drawn into the implant 10J as the lower lock supports 20 rotated into locking position. Tensioning or pulling on the unlocking tether 212 will unlock the lower lock supports 20 and allow the top plate 13 to collapse back into the housing 11. The ability to unlock and collapse the implant 10J can be highly advantageous to a physician placing the device if there is a need to reposition or replace the device after it has been expanded in-vivo.

Figure 47:
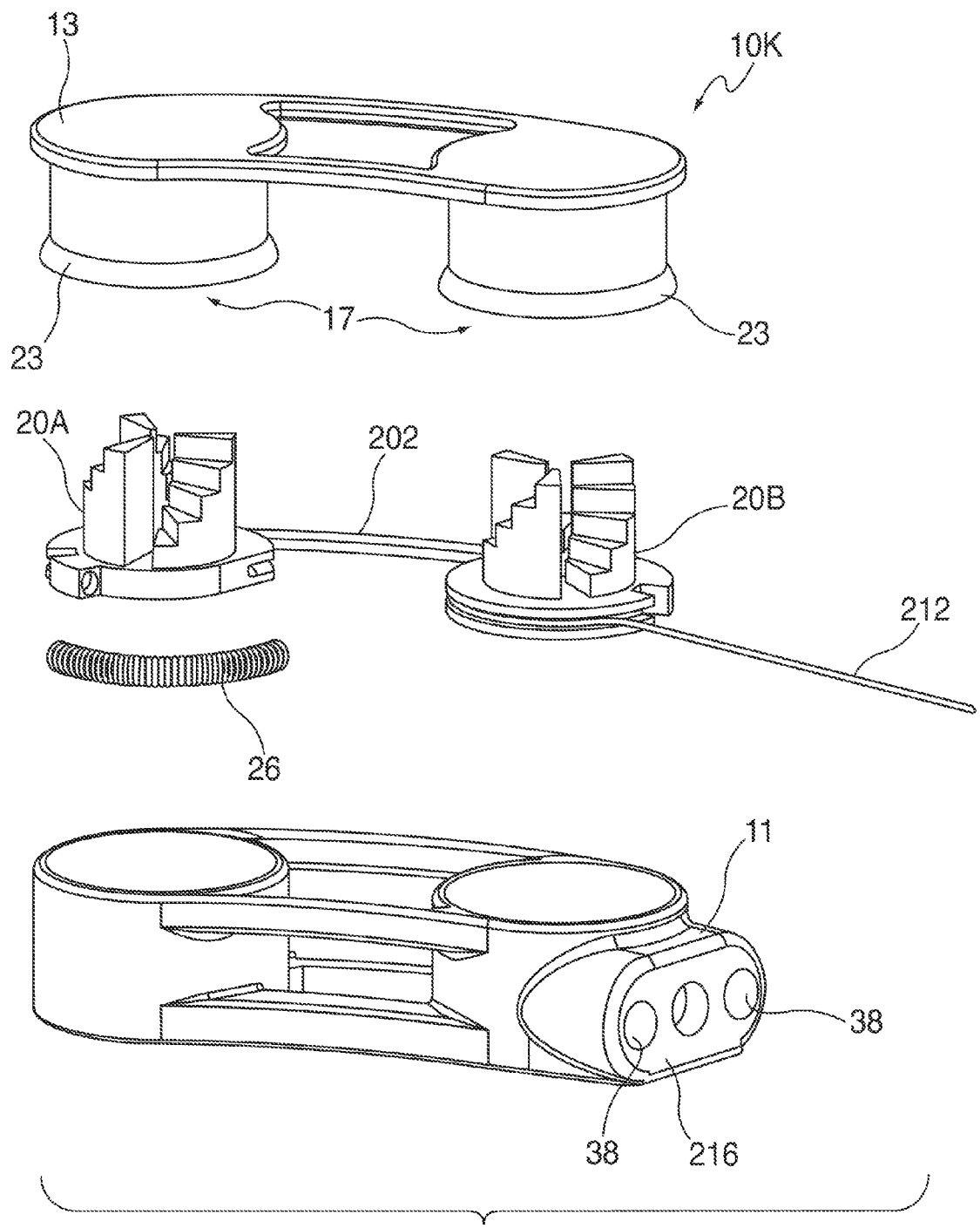
FIG. 47 is an exploded perspective view of another embodiment of the current invention.

Turning now to FIG. 47, another embodiment of an implant 10K is shown with lower lock supports 20 that are located inside the cylinders 16 of the housing 11. In this embodiment the linking element 202 is a solid bar that can transfer compressive as well as tensile loads. The locking actuator 26 rotates the leading lower lock support 20A, which pushes on the linking element 202. The linking element 202 in turn pushes and rotates the following lower lock support 20B. The lower lock supports 20A and 20B engage the upper lock supports 17 that are located inside the pistons 22 (shown in FIG. 14C). The rotation of the following lower lock support 20B pulls the unlocking tether 212 into the housing 11 through the unlocking port 38. The unlocking tether 212 can be tensioned away from the housing 11 to reverse the process and unlock the implant 10K.

Figure 48:
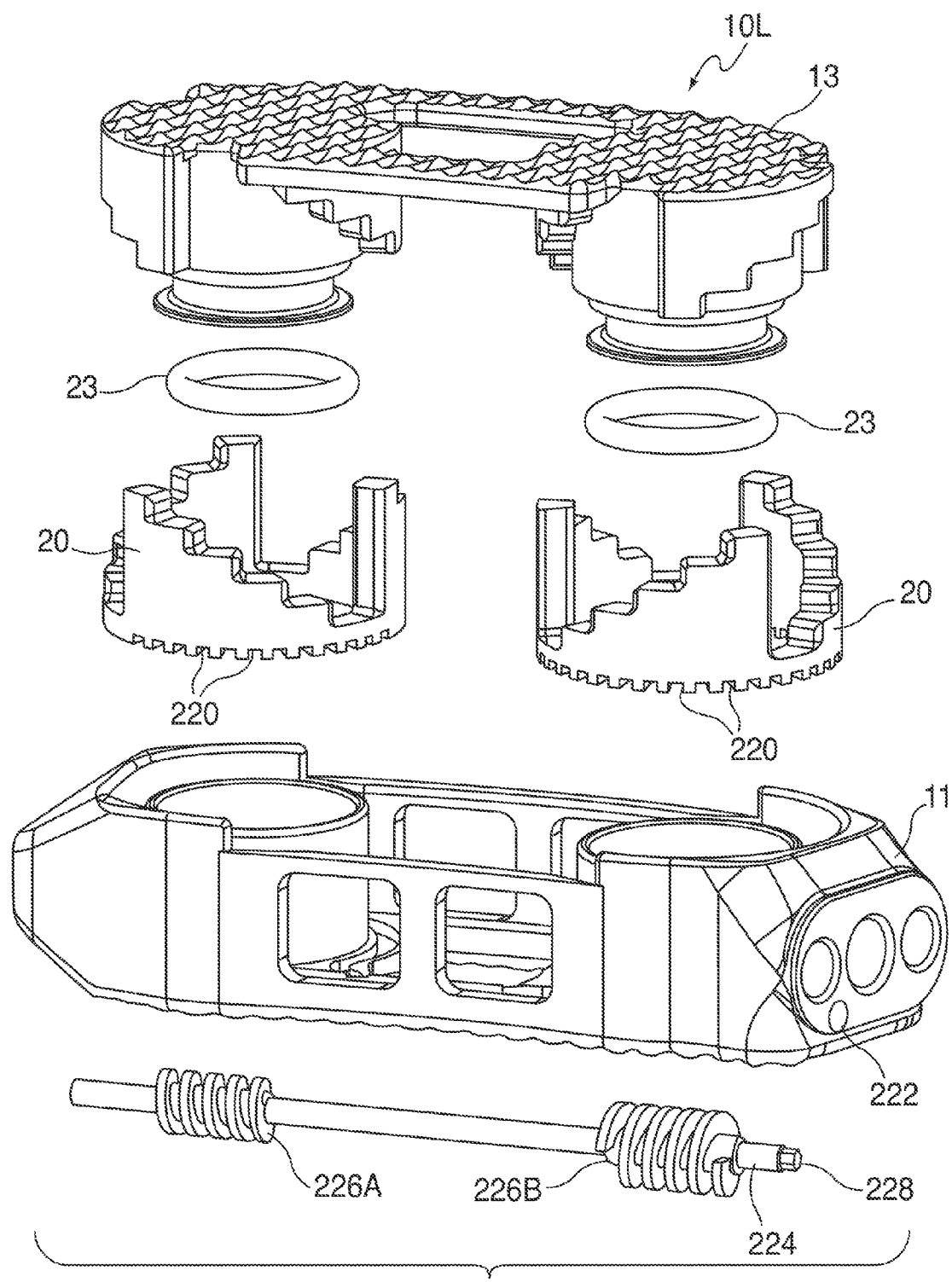
FIG. 48 is an exploded perspective view of another embodiment of the current invention

The use of tension and compression elements as described above are not the only means for coordinating the controlled locking and unlocking of the device. In FIG. 48 an alternative embodiment of the implant 10L is shown wherein thread gears 226A and 226B are used to both lock and unlock the lower lock supports 20 thus forming a combined linking and unlocking element. Threaded gears 226A and 226B are mounted on a shaft 224 that is contained in the base of the housing. The proximal end of shaft 224 has a keyed head 228 that can protrude from or rest in the locking port 222. An external tool (not shown) can interface with the keyed head 228 to rotate it in either direction. Rotating the keyed head 228 will in turn rotate the shaft 224 and the threaded gears 226A and 226B. The threaded gears 226A and 226B transfer the force to the lower lock supports 20 through the geared bottom face 220. In the embodiment shown in FIG. 48 the threaded gear 226A is oriented opposite of the threaded gear 226B. This allows rotation of the shaft 224 to rotate the lower lock supports 20 in opposite directions relative to each other. It is obvious to those schooled in the art that the threaded gears 226A and 226B can be oriented in the same direction if it is desired to rotate the lower lock supports 20 in the same direction. In either case the shaft 224 can be rotated in one direction to rotate the lower lock supports 20 in the locking direction, and the shaft 224 can be rotated in the opposite direction to rotate the lower lock supports 20 in the unlocking direction.

An unlocking tether as described herein can be engaged and tensioned by any number of means including but not limited to gripping the unlocking tether between articulating grips, a collet or split ring clamp, crimping the unlocking tether to a tensioning wire or rod and cutting the unlocking tether to disengage after use, mounting a magnet on the proximal end 214 (FIG. 46A) of the unlocking tether and engaging the magnet with a mating magnet attached to a tensioning wire of rod, adding a female or male thread to the proximal end 214 or the unlocking tether and engaging it with a mating thread on the end of a tensioning rod or wire, or providing a continuous unlocking tether all the way to the point external to the body for tensioning and then cutting the unlocking tether near the implant after use to disengage. It is obvious to those schooled in the art that the unlocking tether can alternatively be pushed or compressed rather than tensioned as long as it is configured to rotate the lower lock supports 20A and B in the unlock direction and deliver sufficient load without buckling when pushed.

Figure 49:
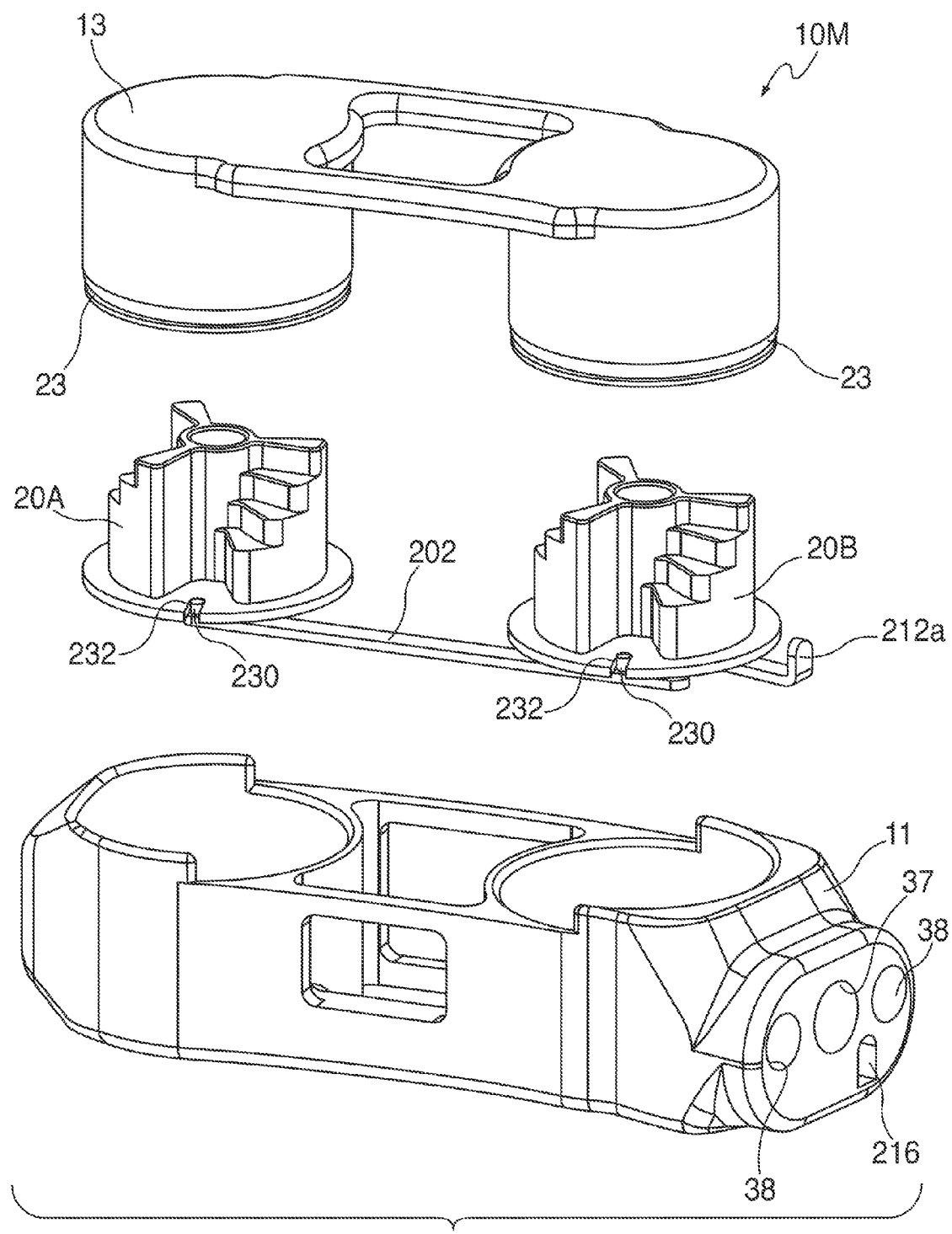
FIG. 49 is an exploded perspective view of another embodiment of the current invention.

FIG. 49 illustrates an alternative embodiment of an implant 10M with a pushable unlocking tether 212a. In this embodiment, unlocking tether 212a engages the proximal lower lock support 20B to rotate it in the unlock direction when the unlocking tether 212a is advanced towards the proximal lower lock support 20B. The link 202 transfers that rotation from the following lower lock support 20B to the leading lower lock support 20A. The link 202 contains engagement pins 230, which extend into receiving slots 232 on the lower lock supports 20A and 20B in order to transfer the lateral movement of the link 202 into rotation of the lower lock supports 20A and 20B. In much the same way, the unlocking tether 212 can contain an engaging pin (not shown) to extend into a receiving slot (not shown) on the following lower lock support 20B to transfer the lateral compressive force applied to the unlocking tether 212a into rotation of the lower lock supports 20B. This is just one method for attaching or engaging the unlocking tether 212 to the lower lock support 20 the numerous methods previously described herein for attaching or engaging the link 202 to the lower lock supports 20 can be used for attaching or engaging the tether 212 as well.

One advantage to pushing the unlocking tether 212a to unlock the implant 10M is that the method for engaging the unlocking tether is simplified. Unlocking tether 212a, which is pushed to unlock the implant 10M can be contained within the implant 10M and a push rod (not shown) can be easily directed into the implant 10M through the unlock port 216 to actuate the unlocking tether 212a and unlock the implant 10M such that it can collapse. This eliminates the need to attach to the unlocking tether 212a which is required when the unlocking tether 212a is tensioned to unlock the implant 10M.

FIGS. 50A-D illustrate an alternate embodiment of the implant 10N embodying features of the invention. Similar to the implant 110 as shown in FIGS. 13A and 13B, the top end plate 113 of the implant 10N articulates relative to the distal piston 122A and proximal piston 122B. The ends of the articulating top plate 113 have spherical projections 2001A and 20001B which are contained within mating pockets 2002A and 2002B in the two pistons 122A and 122b. Split rings 2006A and 2006B are placed over the spherical projections 2001A and 20001B and into the pistons 122A and 122B to vertically constrain the articulating top plate 113 to the pistons. This geometry provides articulation of the top plate 113 along not only the long axis (the axis extending along the line 50C in FIG. 50C), as with the implant 110 shown in FIGS. 13A-B, but also provides articulation in a side-to-side direction, which is an advantage for providing congruence of the implant to the intervertebral space. Thus, the articulating top plate 113 is polyaxially movably coupled to the pistons 122A and 122B, allowing the plate 113 to articulate about at least two axes.

Figure 50A:
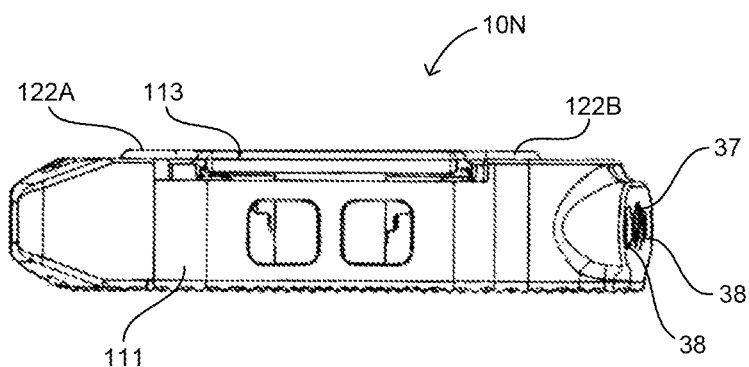
FIG. 50A is a side view of an alternative implant design in a collapsed configuration having an articulating top plate.
Figure 50B:
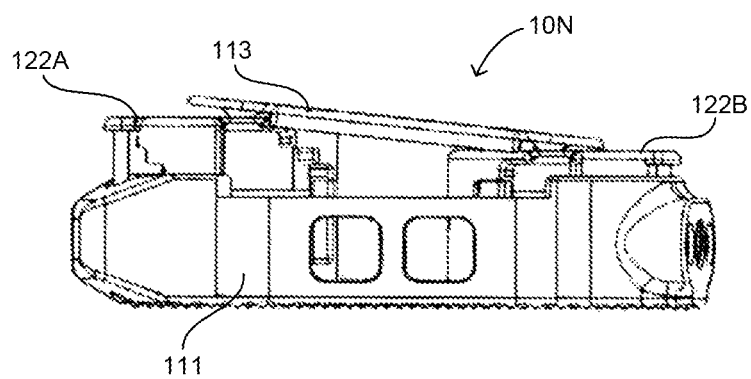
FIG. 50B is a side view of the implant shown in FIG. 50A in an expanded configuration.
Figure 50C:
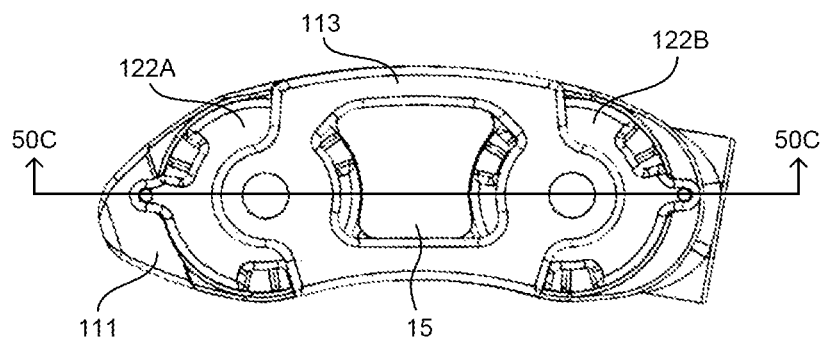
FIG. 50C is a top view of the implant shown in FIG. 50B.
Figure 50D:
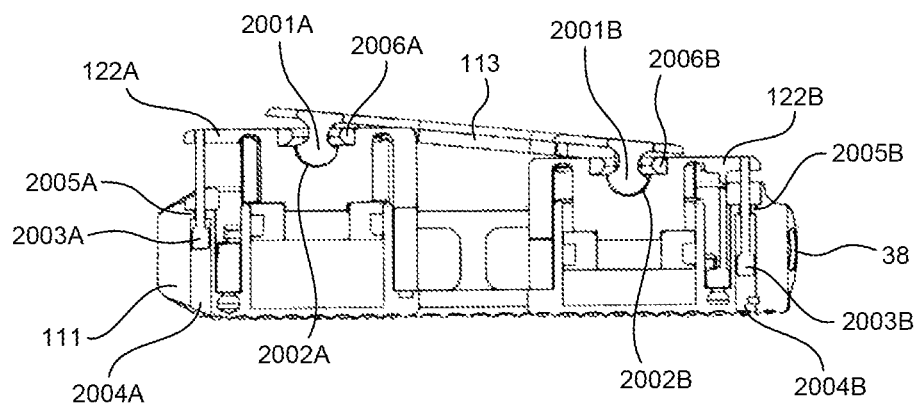
FIG. 50D is a side cross-sectional through line 50D of the implant shown in FIG. 50C.

Also shown in FIG. 50D are vertical constraints 2003A and 2003B which are attached to the distal piston 122A and proximal piston 122B. These two constraints 2003A and 2003B fit inside channels 2004A and 2004B in the housing 111. The top portion of the channels 2004A and 2004B have a narrowed portion 2005A and 2005B that prevent the vertical constraints 2003A and 2003B from advancing out of the housing 111. In this manner these vertical constraints 2003A and 2003B limit the maximum vertical movement of the pistons 122A and 122B relative to the housing 111.

Figure 51A:
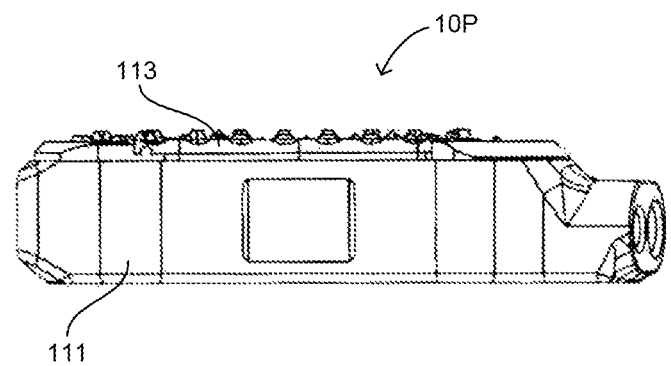
FIG. 51A is a side view of an alternative implant in a collapsed configuration having an articulating top plate.
Figure 51B:
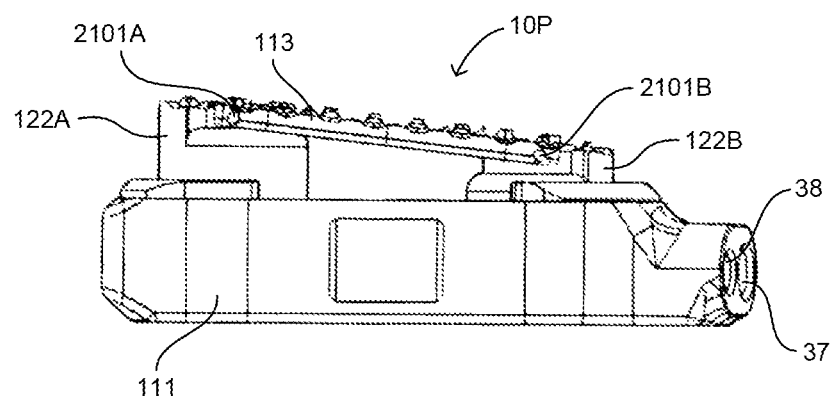
FIG. 51B is a side view of the implant shown in FIG. 51A in an expanded configuration.

FIGS. 51A-B illustrate another alternative embodiment. FIGS. 51A-B illustrate an implant 10P that can have features similar to features in the embodiments illustrated in FIGS. 13A, 14A-C, and 49. The implant 10P has the articulating top plate 113 similar to that shown in FIG. 13A which pivots relative to the distal piston 122A and proximal piston 122B about a distal pivot pin 2101A and a proximal pivot pin 2101B. The implant 10P has a distal piston 122A and a proximal piston 122B. As with the pistons 222a and 222b shown in FIGS. 14A-C, the pistons 122A and 122B can have internal upper lock supports 217. Unlike implant 210, in the illustrated embodiment, the pistons 122A and 122B do not rotate relative to the housing 111 as is the case in the implant 210. Instead, lower lock supports 20A and 20B similar to those shown in FIG. 49 rotate relative to the housing 111 and the two pistons 122A and 122B to lock the height of the expanded implant. In this manner, benefits of several of the previously described embodiments are combined to provide and implant 10P that can lock at different distal and proximal heights.

Figure 52A:
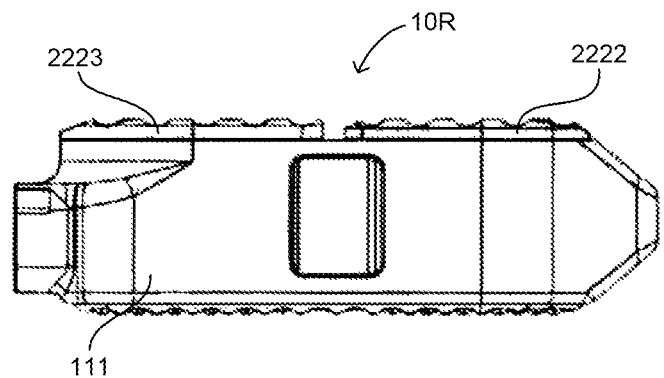
FIG. 52A is a side view of an alternative implant in a collapsed configuration embodying features of the invention which has two separated top plates.
Figure 52B:
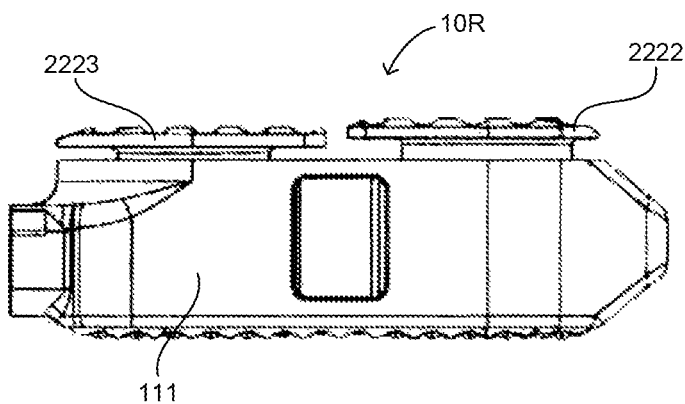
FIG. 52B is a side view of the implant shown in FIG. 52A in a slightly expanded configuration.
Figure 52C:
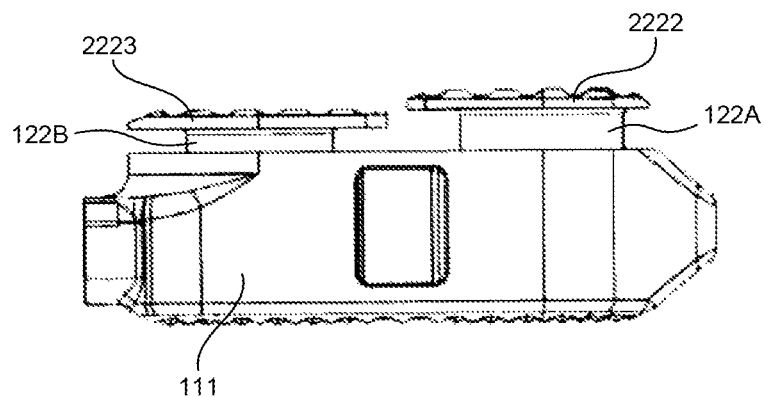
FIG. 52C is a side view of the implant shown in FIG. 52B in a more expanded configuration.
Figure 52D:
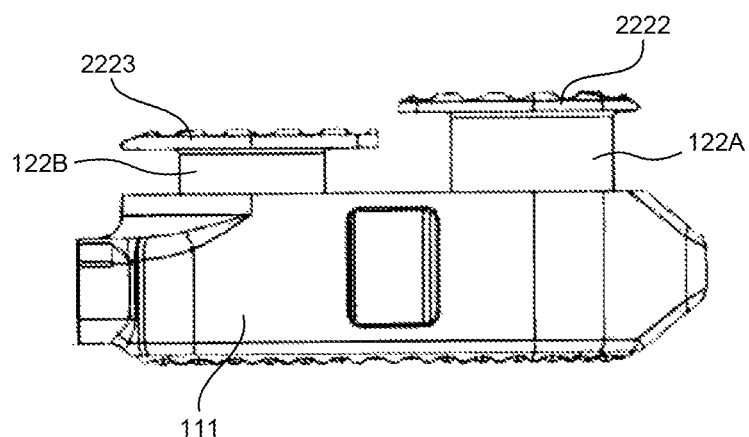
FIG. 52D is a side view of the implant shown in FIG. 52C in a fully expanded configuration.
Figure 52E:
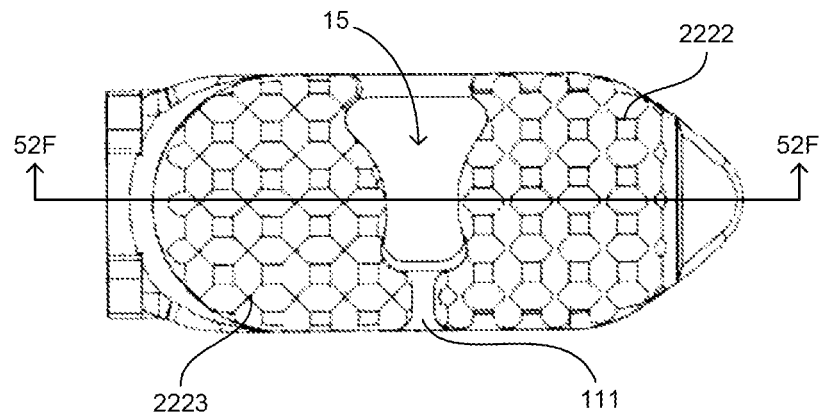
FIG. 52E is a top view of the implant shown in FIG. 52D.

FIGS. 52A-F illustrate an alternative embodiment of the present invention, exemplified by implant 10R. In this embodiment, implant 10R can include a distal piston top plate 2222 that can be completely separate from a proximal piston top plate 2223. As shown in FIGS. 52B-D, the two piston top plates 2222 and 2223 can each expand to different heights relative to the housing 111. Thus, the independently adjustable top plates and their respective pistons provide a simple construct that can achieve variable expansion similar to the articulating top plate 113 in implants 10N and 10P.

In some embodiments, the extendable members, such as pistons 122A and 122B, may be actuated by a common actuator such as a single syringe or other pressurized fluid source but constrained as described herein to rise to independent/different heights. Such constraint may be provided by specific constraint means as described, by a common top plate such as shown in FIG. 50D or a combination thereof.

Figure 52F:
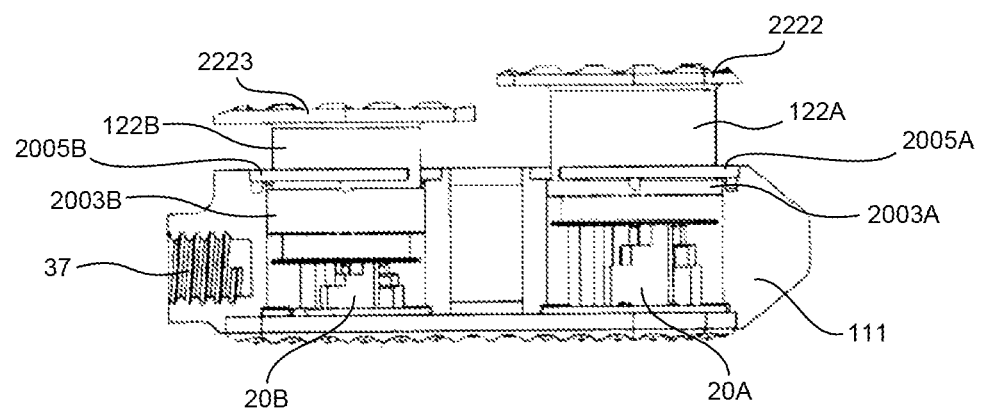
FIG. 52F is a side cross-sectional through line 52F of the housing 111 of the implant shown in FIG. 52E.

As shown in FIG. 52F, the implant 10R can include a proximal lower lock support 20B that can have stepped support surfaces that have shorter increments than the stepped support surfaces on a distal lower lock support 20A. The mating stepped support surfaces on the proximal upper lock support (not shown) in the proximal piston 122B can also have shorter increments than the stepped support surfaces on the upper lock support in the distal piston 122A. This variation in stepped support surface can be designed to produce a specifically desired expanded height difference between the expanded distal piston top plate 2222 and the expanded proximal piston top plate 2223. In addition, the expanded height difference can vary with the amount of expansion. This variation can be valuable, for example, for creating lordotic congruence between the implant 10R and the vertebral bodies as the amount of lordosis required for proper congruence and spinal foraminal opening can increase along with the increase in distance between the vertebral bodies.

The implant 10R can also have vertical constraints 2005A and 2005B which can be attached to the housing 111. In the illustrated embodiment, the vertical constraints 2005A and 2005B can prevent wide portions 2003A and 2003B of the distal piston 122A and proximal piston 122B from advancing out of the housing 111. In this manner, these vertical constraints 2005A and 2005B can limit the maximum vertical movement of the pistons 2222 and 2223 relative to the housing 111.

Figure 53:
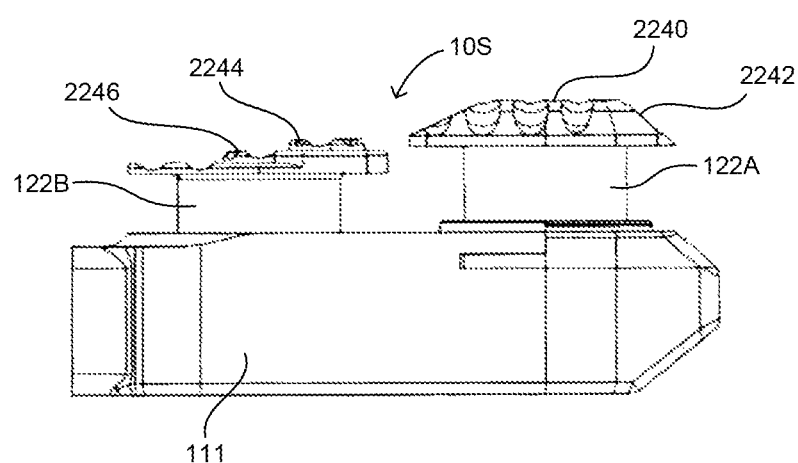
FIG. 53 is a side view of an alternative implant design in a fully expanded configuration having two separated top plates.

FIG. 53 illustrates yet another alternative embodiment. As shown in FIG. 53, an implant 10S can have a distal piston 122A that can have both a horizontal vertebral engagement surface 2240 and an angled vertebral engagement surface 2242, such that the distal piston 122A can have a variation in vertebral engagement surface angles. These variations in vertebral engagement surface angles can be beneficial for providing even better congruence between the implant 10S and the vertebral bodies when a lordotic or variable height expansion is desired. The implant 10S can also have a proximal piston 122B with a higher horizontal vertebral engagement surface 2244 and a lower horizontal vertebral engagement surface 2246, which can also improve congruence between the implant 10S and the vertebral bodies when a lordotic or variable height expansion is desired. As will be recognized by a person of ordinary skill in the art, any combination of these varied vertebral engagement surfaces can be employed on either the distal piston 122A, the proximal piston 122B, the articulating top plate 113 or the posterior surface of the housing 111 to provide optimal vertebral body congruency.

The features of the current invention have been described in terms of an implant comprised of a pair of cylinder/piston/lock/and related features, however it is obvious to those schooled in the art that the described features can be included in an implant with only a single set or more than two sets of these features.

A lateral cage implant, as illustrated for exemplary embodiments of the present invention herein, is particularly advantaged by the use of anchors as described herein because the lateral approach to the spine is a long and narrow approach, which limits the ability of the surgeon to use other instrumentation to extend anchors from the cage (as can be done more readily, for example, with an anterior approach where the access is not as narrow). However, as will be appreciated by persons of ordinary skill in the art, while particular, additional advantages may be presented in connection with the lateral approach and cages designed therefore, anchors according to embodiments of the present invention are advantageous for any approach as they can produce the required extension forces regardless of patient anatomy or other restrictions on the use of alternative extension means by the surgeon.

Elements of the description herein focused on the manner in which the locking elements are configured to lock the implant in extended configurations. Although this locking action resists the forces placed on the implant that would tend to force it back into a collapsed configuration, that is not the only force the locking elements address. Once inserted between vertebral bodies the implant is subject to lateral forces and torsion moments as well as compressive forces. The locking features along with the other elements of the invention are designed to resist all of these forces to provide an implant that provides stable fixation and distraction.

A partial or complete discectomy is usually performed prior to the insertion of the spinal implant having features of the invention between vertebral bodies. The implant is introduced in its unexpanded state to enable it to be inserted posteriorly with minimal trauma to the patient and risk of injury to nerve roots. Once in place the implant can be expanded to provide both medial and lateral spinal correction. The implant has an unexpanded height of about 5 to about 15 mm, typically about 7 mm and is expandable to at least 130% to about 180% of the unexpanded height. Typically the implant is about 9 to about 15 mm wide, typically about 12 mm wide and about 25 to about 55 mm long, typically about 35 mm long to facilitate minimally invasive insertion and thereby minimize trauma to the patient and risk of injury to nerve roots.

Additional details of the implant such as the attachment of hydraulic lines and lines for transmission of a slurry or liquid bone graft material, device and hydraulic fluid delivery accessories and the like can be found in co-pending application Ser. No. 11/535,432 filed on Sep. 26, 2006 and Ser. No. 11/692,800, filed on Mar. 28, 2007, which are incorporated herein by reference.

It will be appreciated that the implant, including its various components should be formed of biocompatible, substantially incompressible material such as PEEK or titanium, and preferably type 6-4 titanium alloy or other suitable materials which will allow for long-term deployment within a patient.

While the invention has been described in connection with what are presently considered to be the most practical and certain preferred embodiments, it is to be understood that the invention is not limited to the disclosed embodiments and alternatives as set forth above, but on the contrary is intended to cover various modifications and equivalent arrangements included within the scope of the following claims.

For example, while implants described herein are expanded by hydraulic fluid, other expansion means may be employed. For example, the screw mechanism described herein may be employed to expand scissor jacks within the implant to engagement adjacent vertebral surfaces. Further, the implant can be provided with load or pressure sensors that register differential pressure and pressure intensity exerted on the engaging surfaces of the SEC by the patient's vertebrae end plates to generate corrective signals, for example by computer control, that are used, e.g. by the surgeon or by a computer-controlled mechanism to realign the patient's spine. The invention may further include a system that makes these adjustments, responsive to sensor signals, in real time and on a continual basis, such that the shapes of the implant changes to realign the patient's spine or mechanism. Preferably, such system is contemplated for use in setting the positions of the pistons during installation of the implant.

While particular forms of the invention have been illustrated and described herein, it will be apparent that various modifications and improvements can be made to the invention. Additional details of the spinal implant devices may be found in the patents and applications referenced herein. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents and all patent applications referred to above are hereby incorporated by reference in their entirety.

What is claimed is:
1. An expandable implant comprising:
  a body having a first surface and a second surface;
  a first member formed within the body, the first member being actuatable to expand along a first axis to extend the first surface away from the second surface;

a second member actuatable to expand in a lateral direction transverse to the first axis, the second member being actuatable independently of the first member.

2. The expandable implant of claim 1, wherein the first member and the second member are adapted to be expanded by fluid.

3. The expandable implant of claim 2, wherein the fluid is hydraulic fluid.

4. The expandable implant of claim 1, further comprising a first central cavity extending through the body.

5. The expandable implant of claim 4, further comprising a second central cavity extending through the body and separated from the first central cavity by a central member.

6. The expandable implant of claim 5, wherein at least one of the first member and the second member are adapted to be expanded by fluid, the central member providing a fluid flow path between a fluid source and at least one of the first member and the second member.

7. The expandable implant of claim 1, wherein the first surface is adapted to engage a first vertebral body and the second surface is adapted to engage a second vertebral body.

8. The expandable implant of claim 1, wherein the second member includes a piston extendable laterally from the body.

9. An expandable spinal implant for placement between first and second vertebral bodies, comprising:
   a first member having a first surface for engaging a first vertebral body;
   a second member having a second surface for engaging a second vertebral body;
   a third surface laterally oriented between the first and second surfaces;
   a first support element actuatable to extend the first member away from the second member along a first axis; and
   a second support element actuatable to push the third surface outwardly transverse to the first axis, the second support element being actuatable independently of the first support element.

10. The spinal implant of claim 9, wherein the first surface for engaging the first vertebral body includes a top end plate and the second surface for engaging the second vertebral body includes a base plate.

11. The spinal implant of claim 9, further comprising a third support element translatable along a third axis parallel to the first axis.

12. The spinal implant of claim 11, wherein at least two of the first support element, the second support element, and the third support element are translatable by a common actuator.

13. The spinal implant of claim 9, further comprising a locking system that mechanically engages or interlocks with the first member and the second member to lock the expandable spinal implant in an expanded configuration.

14. The spinal implant of claim 9, wherein the second support element includes a piston oriented transverse to the first axis.

15. A method of implanting an expandable implant having a body with a first surface and a second surface, a first member, and a second member, the method comprising:
   inserting the expandable implant in a contracted state;
   actuating the first member to expand the implant from the contracted state to an expanded state wherein the first surface is expanded away from the second surface along a first axis; and
   actuating the second member, independently of the actuation of the first member, to expand the implant in a lateral direction transverse to the first axis.

16. The method of claim 15, wherein the first member and the second member are each configured to be extended by fluid, and wherein extending the first member and extending the second member comprises supplying fluid to each of the first member and the second member.

17. The method of claim 15, wherein the expandable implant further comprises a locking system that mechanically engages or interlocks with the first member to lock the expandable implant in the expanded state, and actuating the first member further comprises locking the expandable implant in the expanded state.

18. The method of claim 15, wherein the expandable implant further comprises a first extendable anchor and the method further comprises extending the first extendable anchor independently of the first member.

19. The method of claim 15, wherein the expandable implant further comprises a cavity configured to receive a bone growth material and the method further comprises providing a bone growth material into the cavity.

20. The method of claim 15, wherein the second member includes a piston oriented in the lateral direction.

* * * * *